United States Patent
Liu et al.

(10) Patent No.: US 11,111,313 B2
(45) Date of Patent: Sep. 7, 2021

(54) ANTI-PCSK9 ANTIBODIES

(71) Applicant: WuXi Biologies Ireland Limited, Dublin (IE)

(72) Inventors: Jieying Liu, Shanghai (CN); Jing Li, Lexington, MA (US)

(73) Assignee: WUXI BIOLOGICS IRELAND LIMITED, Dublin (IE)

(*) Notice: Subject to any disclaimer, the term of this patent is extended or adjusted under 35 U.S.C. 154(b) by 0 days.

(21) Appl. No.: 16/334,767

(22) PCT Filed: Sep. 12, 2017

(86) PCT No.: PCT/CN2017/101357
§ 371 (c)(1),
(2) Date: Mar. 20, 2019

(87) PCT Pub. No.: WO2018/054241
PCT Pub. Date: Mar. 29, 2018

(65) Prior Publication Data
US 2019/0233542 A1    Aug. 1, 2019

(30) Foreign Application Priority Data
Sep. 20, 2016  (WO) ............... PCT/CN2016/099491

(51) Int. Cl.
| C07K 16/40 | (2006.01) |
| A61K 39/395 | (2006.01) |
| C12N 9/64 | (2006.01) |
| A61P 3/06 | (2006.01) |
| A61P 3/00 | (2006.01) |
| A61P 37/04 | (2006.01) |
| A61P 9/00 | (2006.01) |
| A61K 39/00 | (2006.01) |
| A61P 31/00 | (2006.01) |

(52) U.S. Cl.
CPC ............ *C07K 16/40* (2013.01); *A61K 39/395* (2013.01); *A61P 3/00* (2018.01); *A61P 3/06* (2018.01); *A61P 9/00* (2018.01); *A61P 37/04* (2018.01); *C12N 9/6454* (2013.01); *A61K 2039/505* (2013.01); *A61P 31/00* (2018.01); *C07K 2317/21* (2013.01); *C07K 2317/24* (2013.01); *C07K 2317/33* (2013.01); *C07K 2317/76* (2013.01); *C07K 2317/92* (2013.01); *C07K 2317/94* (2013.01)

(58) Field of Classification Search
CPC ............... C07K 16/40; C07K 2317/21; C07K 2317/24; C07K 2317/33; C07K 2317/76; C07K 2317/92; C07K 2317/94; A61K 39/395; A61K 2039/505; A61P 3/00; A61P 31/00; A61P 37/04; A61P 9/00; A61P 3/06; C12N 9/6454
See application file for complete search history.

(56) References Cited

U.S. PATENT DOCUMENTS

| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 6,005,079 A | 12/1999 | Casterman et al. |
| 8,889,834 B2 | 11/2014 | Jackson et al. |
| 8,907,157 B2 | 12/2014 | Buelow |
| 2015/0160247 A1 | 6/2015 | Laaksonen |

FOREIGN PATENT DOCUMENTS

| CN | 101932607 A | 12/2010 |
| CN | 102245641 A | 11/2011 |
| CN | 104311666 A | 1/2015 |
| CN | 104861071 A | 8/2015 |
| CN | 105037554 A | 11/2015 |
| CN | 105214087 A | 1/2016 |
| CN | 105348390 A | 2/2016 |
| CN | 105461809 A | 4/2016 |
| CN | 105705521 A | 6/2016 |
| CN | 105801701 A | 7/2016 |
| CN | 105814085 A | 7/2016 |
| EP | 0183070 A2 | 6/1986 |
| EP | 0244234 A2 | 11/1987 |
| EP | 0402226 A1 | 12/1990 |
| EP | 404097 A2 | 12/1990 |
| EP | 2152880 B1 | 8/2011 |
| EP | 2336329 B1 | 10/2012 |

(Continued)

OTHER PUBLICATIONS

Mateu et al. (Mateu MG, et. al. Eur J Immunol. Jun. 1992;22(6):1385-9 (Year: 1992).*
Greenspan NS, Di Cera E. Defining epitopes: It's not as easy as it seems. Nat Biotechnol. Oct. 1999;17(10):936-7 (Year: 1999).*
Vajdos et al. (J Mol Biol. Jul. 5, 2002;320(2):415-28 (Year: 2002).*
Brown et al. (J Immunol. May 1996;156(9):3285-91 (Year: 1996).*
Jiang, L. , "PCSK9 siRNA Repressed Inflammation Factor Expression and Secretion in ox-LDL-induced THP-1 macrophage cells", master's thesis, University of South China(Mar. 2011), pp. 1-55.
Baigent, C. et al., "Efficacy and safety of more intensive lowering of LDL cholesterol: a meta-analysis of data from 170 000 participants in 26 randomised trials". Lancet 2010, vol. 376(9753), p. 1670-1681.

(Continued)

*Primary Examiner* — Brian Gangle
*Assistant Examiner* — Andrea K McCollum
(74) *Attorney, Agent, or Firm* — Jun He Law Offices P.C.; James J. Zhu

(57) ABSTRACT

The present disclosure provides monoclonal antibodies against Proprotein Convertase Subtilisin/Kexin type 9 (PCSK9), which can block the binding of PCSK9 to low-density lipoprotein (LDL) receptor, and therefore lower the level low-density lipoprotein cholesterol (LDL-C). The antibodies of disclosure provide very potent agents for the treatment of multiple Cardiovascular diseases (CVDs).

12 Claims, 21 Drawing Sheets

Specification includes a Sequence Listing.

(56) References Cited

FOREIGN PATENT DOCUMENTS

| WO | 8700195 A1 | 1/1987 | | |
|---|---|---|---|---|
| WO | 9003430 A1 | 4/1990 | | |
| WO | 9311161 A1 | 6/1993 | | |
| WO | 9404678 A1 | 3/1994 | | |
| WO | 9425591 A1 | 11/1994 | | |
| WO | WO-9846645 A2 | * | 10/1998 | ............ A61P 37/04 |
| WO | 2010029513 A2 | 3/2010 | | |
| WO | 2015200438 A1 | 12/2015 | | |

OTHER PUBLICATIONS

Seidah, N. G. et al., "The secretory proprotein convertase neural apoptosis-regulated convertase 1 (NARC-1): Liver regeneration and neuronal differentiation". Proc Natl Acad Sci U.S.A. 2003, vol. 100, No. 3, p. 928-933.

McNutt, M.G. et al., "Catalytic Activity Is Not Required for Secreted PCSK9 to Reduce Low Density Lipoprotein Receptors in HepG2 Cells". The Journal of Biological Chemistry 2007, vol. 282, No. 29, p. 20799-20803.

Abifadel, M. et al., "Mutations in PCSK9 cause autosomal dominant hypercholesterolemia". Nat Genet 2003, vol. 34, No. 2, p. 154-156.

Verbeek, R. et al., "PCSK9 inhibitors: Novel therapeutic agents for the treatment of hypercholesterolemia". European Journal of Pharmacology 763 (2015), p. 38-47.

Lo Surdo, P. et al., "Mechanistic implications for LDL receptor degradation from the PCSK9/LDLR structure at neutral pH". EMBO Rep 2011, vol. 12, No. 12, p. 1300-1305.

Farnier, M., "PCSK9: From discovery to therapeutic applications". Archives of Cardiovascular Disease (2014),107, p. 58-66.

Dias, C.S. et al., "Effects of AMG 145 on Low-Density Lipoprotein Cholesterol Levels". Journal of the American College of Cardiology 2012, 60(19), p. 1888-1898.

Giugliano, R.P. et al., "Efficacy, safety, and tolerability of a monoclonal antibody to proprotein convertase subtilisin/kexin type 9 in combination with a statin in patients with hypercholesterolaemia (LAPLACETIMI57): a randomised, placebo-controlled, dose-ranging, phase 2 study".Lancet, 2012, 380(9858), 2007-2017, p. 1-20.

McKenney, J.M. et al., "Safety and Efficacy of a Monoclonal Antibody to Proprotein Convertase Subtilisin/Kexin Type 9 Serine Protease, SAR236553/REGN727, in Patients With Primary Hypercholesterolemia Receiving Ongoing Stable Atorvastatin Therapy". Journal of the American College of Cardiology 2012, 59(25), p. 2344-2353.

Al-Lazikani, B. et al., "Standard Conformations for the Canonical Structures of Immunoglobulins". J. Mol. Biol.(1997), 273(4), p. 927-948.

Chothia, C. et al., "Domain Association in Immunoglobulin Molecules". J Mol Biol. Dec. 5, 1985; 186(3), p. 651-663.

Chothia, C. et al., "Canonical Structures for the Hypervariable Regions of Immunoglobulins ". J.Mol.Biol.(1987), 196, p. 901-917.

Chothia, C. et al., "Conformations of immunoglobulin hypervariable regions". Nature. (Dec. 21-28, 1989);342(6252), p. 877-883.

Huston, J.S. et al., "Protein engineering of antibody binding sites: Recovery of specific activity in an anti-digoxin single-chain Fv analogue produced in *Escherichia coli*". Proc Natl Acad Sci USA(1988), vol. 85, p. 5879-5883.

Riechmann, L. et al., "Single domain antibodies: comparison of camel VH and camelised human VH domains". Journal of Immunological Methods(1999), 231(1-2),p. 25-38.

Muyldermans, S., "Single domain camel antibodies: current status". Reviews in Molecular Biotechnology(2001) , 74(4), p. 277-302.

Hamers-Casterman, C. et al., "naturally occurring antibodies devoid of light chains". Nature. (1993), vol. 363(6428), p. 446-448.

Nguyen, V.K. et al., "Heavy-chain antibodies in Camelidae; a case of evolutionary innovation". Immunogenetics (2002). 54(1), p. 39-47.

Nguyen, V.K. et al., "Heavy-chain only antibodies derived from dromedary are secreted and displayed by mouse B cells". Immunology(2003). 109(1), p. 93-101.

Koch-Nolte, F. et al., "Single domain antibodies from llama effectively and specifically block T cell ecto-ADP-ribosyltransferase ART2.2 in vivo".The FASEB Journal(2007), 21(13), p. 3490-3498.

Holliger, P. et al., ""Diabodies": Small bivalent and bispecific antibody fragments", Proc Natl Acad Sci USA(1993). 90(14), p. 6444-6448.

Burnett, J.R. et al., "Common and Rare Gene Variants Affecting Plasma LDL Cholesterol", Clin Biochem Rev(2008), 29(1), p. 11-26.

Benjannet, S. et al., "NARC-1/PCSK9 and its natural mutants: zymogen cleavage and effects on the low density lipoprotein (LDL) receptor and LDL cholesterol", The Journal of Biological Chemistry(2004), 279(47), p. 48865-48875.

Fasano, T. et al., "Degradation of LDLR protein mediated by 'gain of function' PCSK9 mutants in normal and ARH cells", Atherosclerosis(2009) . 203(1), p. 166-171.

Altschul, S.F. et al., "Basic Local Alignment Search Tool", J. Mol. Biol.(1990), 215, p. 403-410.

Stephen, F. et al., "Gapped BLAST and PSI-BLAST: a new generation of protein database search programs", Nucleic Acids Research(1997), vol. 25, No. 17, p. 3389-3402.

Higgins, D.G. et al., "Using Clustal for Multiple Sequence Alignments", Methods in Enzymology(1996), vol. 266, p. 383-402.

Larkin, M.A. et al., "Clustal W and Clustal X version 2.0", Bioinformatics (Oxford, England, 2007), vol. 23, No. 21, p. 2947-2948.

Osborn, M. J. et al, "High-Affinity IgG Antibodies Develop Naturally in Ig-Knockout Rats Carrying Germline Human IgH/Igk/Igλ Loci Bearing the rat C H Region", Journal of Immunology (2013), 190, p. 1481-1490.

Ma, B. et al., "Human antibody expression in transgenic rats: Comparison of chimeric IgH loci with human VH, D and JH but bearing different rat C-gene regions", Journal of Immunological Methods(2013), 400-401, p. 78-86.

Geurts, A. et al., "Knockout Rats Produced Using Designed Zinc Finger Nucleases", Science (2009), 325(5939):433, p. 1-3.

Lonberg, N. et al., "Antigen-specific human antibodies from mice comprising four distinct genetic modifications". Nature(1994), vol. 368(6474), p. 856-859.

Mendez, M. J. et al., "Functional transplant of megabase human immunoglobulin loci recapitulates human antibody response in mice", Nature Genetics(1997), vol. 15, p. 146-156.

Ishida, I. et al., "Production of Human Monoclonal and Polyclonal Antibodies in TransChromo Animals", Cloning and Stem Cells (2002), vol. 4, p. 91-102.

Murphy, A. J. et al., "Mice with megabase humanization of their immunoglobulin genes generate antibodies as afficiently as normal mice". Proc Natl Acad Sci USA(2014), vol. 111, No. 14, p. 5153-5158.

Lee, E-C. et al., "Complete humanization of the mouse immunoglobulin loci enables efficient therapeutic antibody discovery", Nature Biotechnology(2014), 32, p. 356-363.

Flisikowska, T.et al., "Efficient Immunoglobulin Gene Disruption and Targeted Replacement in Rabbit Using Zinc Finger Nucleases", PLoS One (2011), vol. 6, Issue 6, e21045, p. 1-10.

Graham, F.L. et al., "Characteristics of a Human Cell Line Transformed by DNA from Human Adenovirus Type 5", J. Gen Virol. (1977), 36, p. 59-72.

Urlaub, G. et al., "Isolation of Chinese hamster cell mutants deficient in dihydrofolate reductase activity", Proc. Natl. Acad. Sci. USA (1980), vol. 77, No. 7, p. 4216-4220.

Mather, J.P. et al., "Establishment and Characterization of Two Distinct Mouse Testicular Epithelial Cell Lines", Biology of Reproduction(1980), 23, p. 243-251.

Mather, J.P. et al., "Culture of Testicular Cells in Hormone-Supplemented Serun-Free Medium", Annals N.Y. Acad. Sci. (1982), 383, p. 44-68.

Ham, R. G. et al., "Media and Growth Requirements", Basic Methods (1979), 58, p. 44-93.

(56) References Cited

OTHER PUBLICATIONS

Barnes, D. et al., "Methods for Growth of Cultured Cells in Serum-Free Medium", Analytical Biochemistry (1980),102, p. 255-270.
Carter, P. et al., "High Level *Escherichia coli* Expression and Production of a Bivalent Humanized Antibody Fragment", Bio/Technology (1992), vol. 10, p. 163-167.
Lindmark, R. et al., "Binding of Immunoglobulins to Protein A and Immunoglobulin levels in Mammalian Sera", Journal of Immunological Methods(1983), 62, p. 1-13.
Guss, B. et al., "Structure of the IgG-binding regions of streptococcal protein G ", The EMBO Journal (1986), vol. 5, No. 7, p. 1567-1575.
International Search Report of PCT Application No. PCT/CN2017/101357 (dated Nov. 30, 2017).
Evan A. Stein, et al. "Effect of a Monoclonal Antibody to PCSK9 on LDL Cholesterol.", New England Journal of Medicine, vol. 366, No. 12, Mar. 22, 2012(Mar. 22, 2012), pp. 1108-1118, XP055049842, ISSN: 0028-4793, DOI: 10.1056/NEJMoa1105803.

* cited by examiner

SEQ ID NO: 101

Figure 1

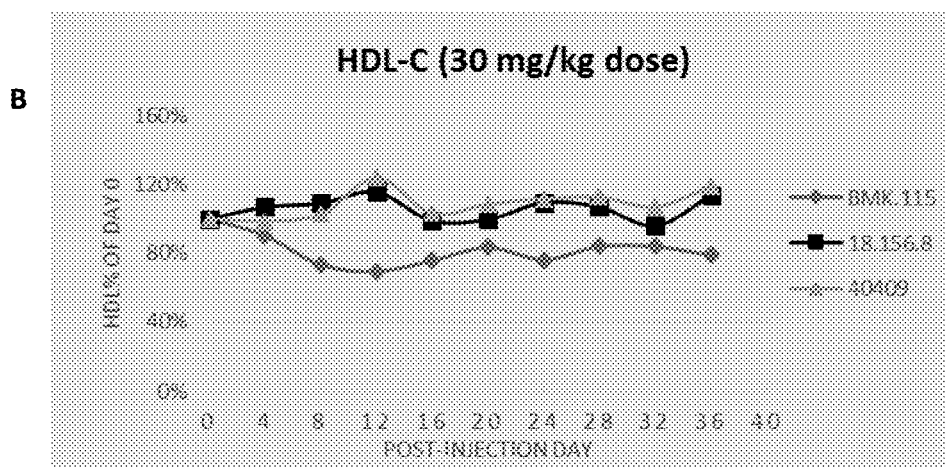
Figure 21B
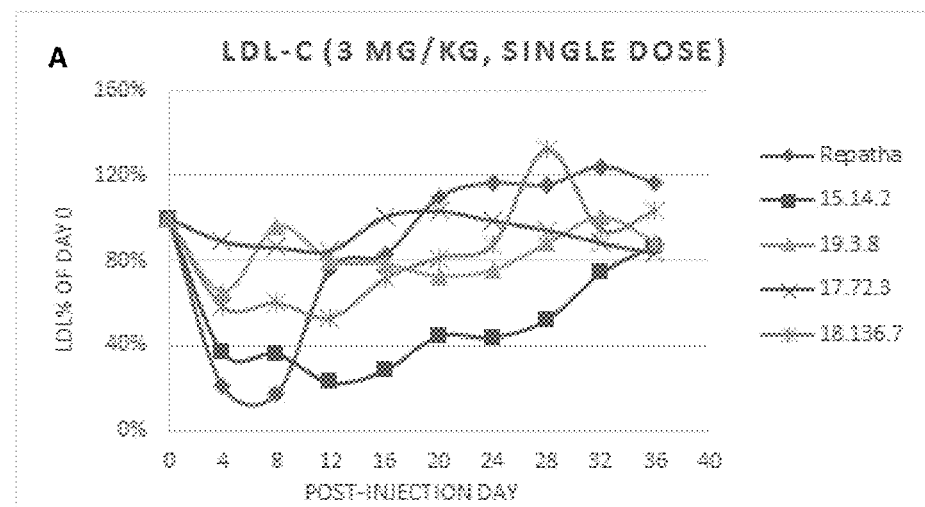
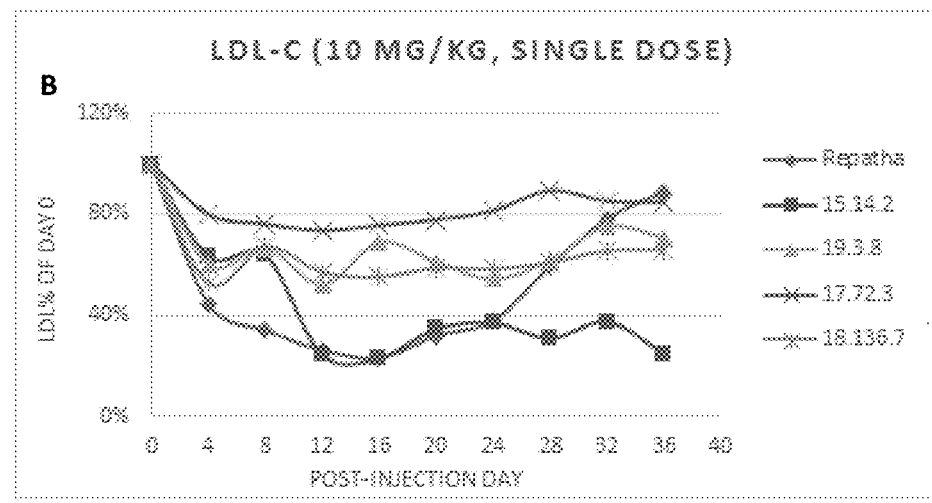
Figure 22

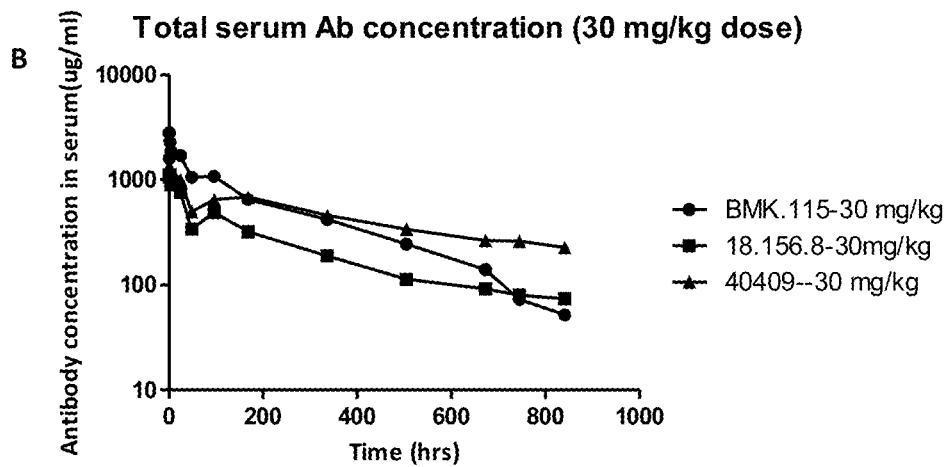
Figure 24B
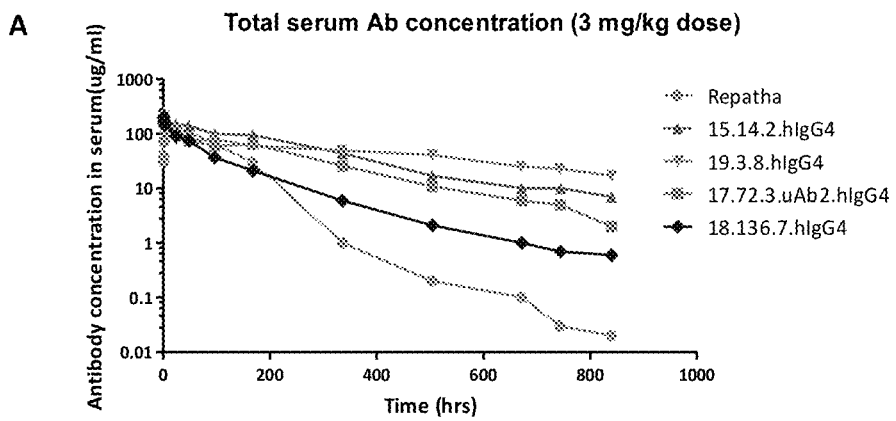
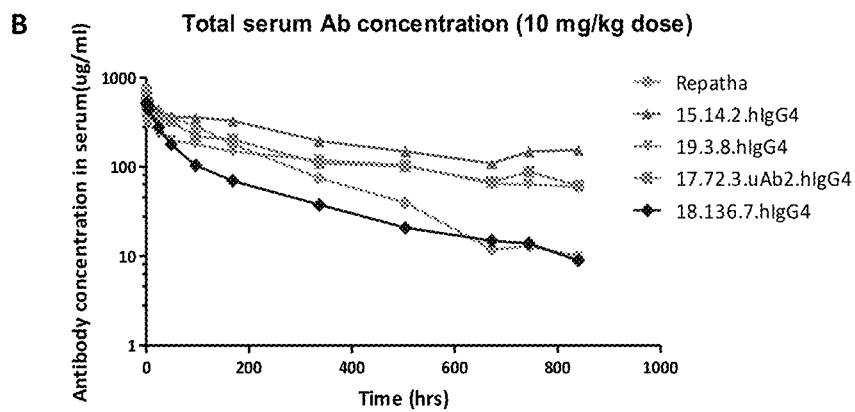
Figure 25

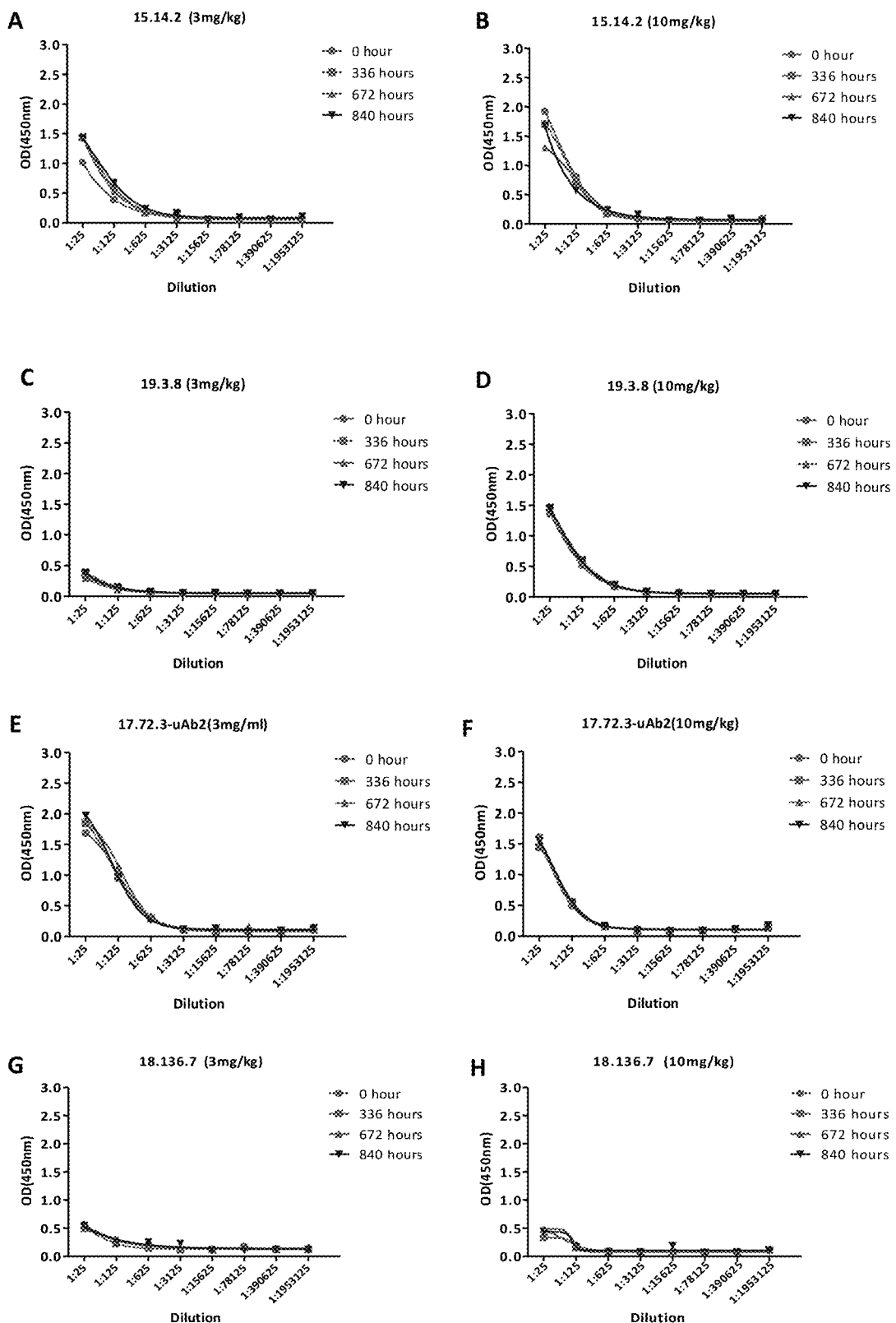
Figure 27A-H

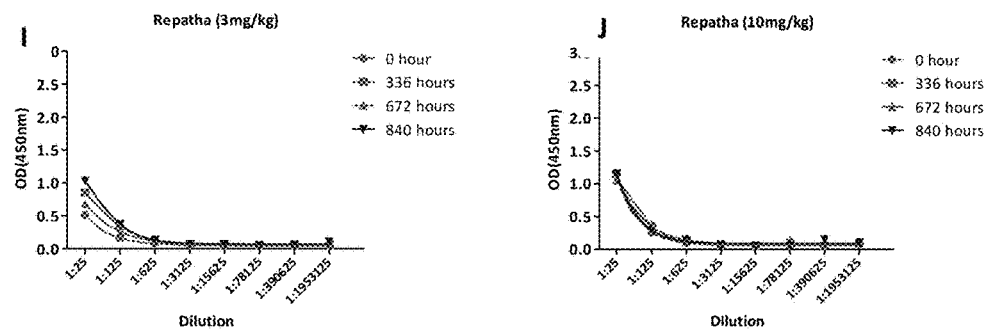
Figure 27I-J
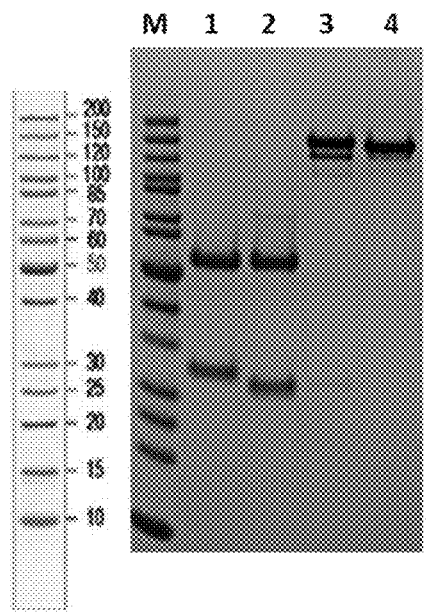
Figure 28A
Figure 28B

SEQUENCE LISTING

```
<160> NUMBER OF SEQ ID NOS: 101

<210> SEQ ID NO 1
<211> LENGTH: 7
<212> TYPE: PRT
<213> ORGANISM: Homo sapiens

<400> SEQUENCE: 1

Ser Asn Ser Ala Ala Trp Asn
1               5
```

<210> SEQ ID NO 2
<211> LENGTH: 21
<212> TYPE: DNA
<213> ORGANISM: Homo sapiens

<400> SEQUENCE: 2
agcaacagtg ctgcttggaa c                                              21

<210> SEQ ID NO 3
<211> LENGTH: 18
<212> TYPE: PRT
<213> ORGANISM: Homo sapiens

<400> SEQUENCE: 3

Arg Thr Tyr Ser Arg Ser Lys Trp Tyr His Asp Tyr Ala Val Ser Val
1               5                   10                  15

Lys Gly

<210> SEQ ID NO 4
<211> LENGTH: 54
<212> TYPE: DNA
<213> ORGANISM: Homo sapiens

<400> SEQUENCE: 4
aggacatact ccaggtccaa gtggtatcat gattatgcag tatctgtgaa aggt          54

<210> SEQ ID NO 5
<211> LENGTH: 21
<212> TYPE: PRT
<213> ORGANISM: Homo sapiens

<400> SEQUENCE: 5

Asp Trp Glu Thr Ser Ile Trp Asn Asp Asp Gly Pro Asn Tyr Tyr Asn
1               5                   10                  15

Tyr Gly Met Asp Val
            20

<210> SEQ ID NO 6
<211> LENGTH: 63
<212> TYPE: DNA
<213> ORGANISM: Homo sapiens

<400> SEQUENCE: 6
gattgggaga cctctatctg gaacgacgac ggtcccaact actacaacta cggtatggac    60
gtc                                                                  63

<210> SEQ ID NO 7
<211> LENGTH: 11
<212> TYPE: PRT
<213> ORGANISM: Homo sapiens

<400> SEQUENCE: 7

Arg Ala Ser Gln Gly Ile Arg Asn Asp Leu Gly
1               5                   10

<210> SEQ ID NO 8
<211> LENGTH: 33
<212> TYPE: DNA
<213> ORGANISM: Homo sapiens

<400> SEQUENCE: 8
cgggcaagtc agggcattag aaatgattta ggc                                 33

<210> SEQ ID NO 9
<211> LENGTH: 7
<212> TYPE: PRT
<213> ORGANISM: Homo sapiens

<400> SEQUENCE: 9

Gly Ala Ser Ser Leu Gln Ser
1               5

<210> SEQ ID NO 10
<211> LENGTH: 21
<212> TYPE: DNA
<213> ORGANISM: Homo sapiens

<400> SEQUENCE: 10
ggtgcatcca gtttgcaaag t                                              21

<210> SEQ ID NO 11
<211> LENGTH: 9
<212> TYPE: PRT
<213> ORGANISM: Homo sapiens

<400> SEQUENCE: 11

Leu Gln His Asn Asn Tyr Pro Trp Thr
1               5

<210> SEQ ID NO 12
<211> LENGTH: 27
<212> TYPE: DNA
<213> ORGANISM: Homo sapiens

<400> SEQUENCE: 12
ctacagcata taattaccc gtggacg                                         27

<210> SEQ ID NO 13
<211> LENGTH: 5
<212> TYPE: PRT
<213> ORGANISM: Homo sapiens

<400> SEQUENCE: 13

Ser Tyr Gly Met His
1               5

<210> SEQ ID NO 14
<211> LENGTH: 15
<212> TYPE: DNA
<213> ORGANISM: Homo sapiens

<400> SEQUENCE: 14
agctatggca tgcac                                                     15

<210> SEQ ID NO 15
<211> LENGTH: 17
<212> TYPE: PRT
<213> ORGANISM: Homo sapiens

<400> SEQUENCE: 15

Val Ile Trp Tyr Asp Gly Thr Asn Lys Tyr Tyr Ala Asp Ser Val Lys
1               5                   10                  15
Gly

<210> SEQ ID NO 16
<211> LENGTH: 51

```
<212> TYPE: DNA
<213> ORGANISM: Homo sapiens

<400> SEQUENCE: 16
gttatatggt atgatggaac taataaatac tatgcagact ccgtgaaggg c        51

<210> SEQ ID NO 17
<211> LENGTH: 5
<212> TYPE: PRT
<213> ORGANISM: Homo sapiens

<400> SEQUENCE: 17

Glu Lys Gly Leu Asp
1               5

<210> SEQ ID NO 18
<211> LENGTH: 15
<212> TYPE: DNA
<213> ORGANISM: Homo sapiens

<400> SEQUENCE: 18
gagaaggggc tggac                                                15

<210> SEQ ID NO 19
<211> LENGTH: 17
<212> TYPE: PRT
<213> ORGANISM: Homo sapiens

<400> SEQUENCE: 19

Lys Ser Ser Gln Ser Val Leu Tyr Ser Ser Thr Asn Lys Asn Tyr Leu
1               5                   10                  15

Val

<210> SEQ ID NO 20
<211> LENGTH: 51
<212> TYPE: DNA
<213> ORGANISM: Homo sapiens

<400> SEQUENCE: 20
aagtccagcc agagtgtttt atacagctcc accaataaga actacttagt t         51

<210> SEQ ID NO 21
<211> LENGTH: 7
<212> TYPE: PRT
<213> ORGANISM: Homo sapiens

<400> SEQUENCE: 21

Trp Ala Ser Thr Arg Glu Ser
1               5

<210> SEQ ID NO 22
<211> LENGTH: 21
<212> TYPE: DNA
<213> ORGANISM: Homo sapiens

<400> SEQUENCE: 22
tgggcatcta cccgggaatc c                                          21

<210> SEQ ID NO 23
<211> LENGTH: 9
<212> TYPE: PRT
<213> ORGANISM: Homo sapiens

<400> SEQUENCE: 23
```

Gln Gln Tyr Tyr Ser Thr Pro Trp Thr
1               5

<210> SEQ ID NO 24
<211> LENGTH: 27
<212> TYPE: DNA
<213> ORGANISM: Homo sapiens

<400> SEQUENCE: 24
cagcaatatt atagtactcc gtggacg                                27

<210> SEQ ID NO 25
<211> LENGTH: 5
<212> TYPE: PRT
<213> ORGANISM: Homo sapiens

<400> SEQUENCE: 25

Arg Phe Ala Met Ser
1               5

<210> SEQ ID NO 26
<211> LENGTH: 15
<212> TYPE: DNA
<213> ORGANISM: Homo sapiens

<400> SEQUENCE: 26
agatttgcca tgagc                                             15

<210> SEQ ID NO 27
<211> LENGTH: 17
<212> TYPE: PRT
<213> ORGANISM: Homo sapiens

<400> SEQUENCE: 27

Ser Ile Ser Asp Asn Ala Gly Arg Thr Tyr Phe Ala Asp Ser Val Lys
1               5                   10                  15

Gly

<210> SEQ ID NO 28
<211> LENGTH: 51
<212> TYPE: DNA
<213> ORGANISM: Homo sapiens

<400> SEQUENCE: 28
agtattagtg acaatgctgg taggacatac ttcgcagact ccgtgaaggg c      51

<210> SEQ ID NO 29
<211> LENGTH: 11
<212> TYPE: PRT
<213> ORGANISM: Homo sapiens

<400> SEQUENCE: 29

Leu Ser Asn Trp Gly Pro Tyr Gly Met Asp Val
1               5                   10

<210> SEQ ID NO 30
<211> LENGTH: 33
<212> TYPE: DNA
<213> ORGANISM: Homo sapiens

<400> SEQUENCE: 30
ctctcaaact ggggtcctta cggtatggac gtc                          33

```
<210> SEQ ID NO 31
<211> LENGTH: 14
<212> TYPE: PRT
<213> ORGANISM: Homo sapiens

<400> SEQUENCE: 31

Thr Gly Thr Ser Ser Asp Val Gly Tyr Tyr Asn Tyr Val Ser
1               5                   10

<210> SEQ ID NO 32
<211> LENGTH: 42
<212> TYPE: DNA
<213> ORGANISM: Homo sapiens

<400> SEQUENCE: 32
actggaacca gcagtgacgt tggttattat aactatgtct cc                    42

<210> SEQ ID NO 33
<211> LENGTH: 7
<212> TYPE: PRT
<213> ORGANISM: Homo sapiens

<400> SEQUENCE: 33

Glu Val Asn Lys Arg Pro Ser
1               5

<210> SEQ ID NO 34
<211> LENGTH: 21
<212> TYPE: DNA
<213> ORGANISM: Homo sapiens

<400> SEQUENCE: 34
gaggtcaata agcggccctc a                                           21

<210> SEQ ID NO 35
<211> LENGTH: 11
<212> TYPE: PRT
<213> ORGANISM: Homo sapiens

<400> SEQUENCE: 35

Ser Ser Tyr Ala Gly Ser Lys Asn Phe Val Val
1               5                   10

<210> SEQ ID NO 36
<211> LENGTH: 33
<212> TYPE: DNA
<213> ORGANISM: Homo sapiens

<400> SEQUENCE: 36
agctcatatg caggcagcaa aaattttgtg gta                              33

<210> SEQ ID NO 37
<211> LENGTH: 6
<212> TYPE: PRT
<213> ORGANISM: Homo sapiens

<400> SEQUENCE: 37

Ser Tyr Asn Trp Trp Ser
1               5

<210> SEQ ID NO 38
<211> LENGTH: 18
<212> TYPE: DNA
<213> ORGANISM: Homo sapiens
```

<400> SEQUENCE: 38
agttataact ggtggagt                                                         18

<210> SEQ ID NO 39
<211> LENGTH: 16
<212> TYPE: PRT
<213> ORGANISM: Homo sapiens

<400> SEQUENCE: 39

Glu Ile His His Ser Gly Thr Thr Asn Tyr Asn Pro Ser Leu Lys Ser
1               5                   10                  15

<210> SEQ ID NO 40
<211> LENGTH: 48
<212> TYPE: DNA
<213> ORGANISM: Homo sapiens

<400> SEQUENCE: 40
gaaatccatc atagtgggac caccaactac aacccgtccc tcaagagt                        48

<210> SEQ ID NO 41
<211> LENGTH: 9
<212> TYPE: PRT
<213> ORGANISM: Homo sapiens

<400> SEQUENCE: 41

Asp Tyr Ser Gly Ser Tyr Phe Asp Tyr
1               5

<210> SEQ ID NO 42
<211> LENGTH: 27
<212> TYPE: DNA
<213> ORGANISM: Homo sapiens

<400> SEQUENCE: 42
gattatagtg ggagctactt tgactac                                               27

<210> SEQ ID NO 43
<211> LENGTH: 11
<212> TYPE: PRT
<213> ORGANISM: Homo sapiens

<400> SEQUENCE: 43

Arg Thr Ser Gln Ser Leu Ser Ser Tyr Val Ala
1               5                   10

<210> SEQ ID NO 44
<211> LENGTH: 33
<212> TYPE: DNA
<213> ORGANISM: Homo sapiens

<400> SEQUENCE: 44
aggaccagtc agagtctaag cagctacgta gcc                                        33

<210> SEQ ID NO 45
<211> LENGTH: 7
<212> TYPE: PRT
<213> ORGANISM: Homo sapiens

<400> SEQUENCE: 45

Asp Ala Ser Lys Arg Ala Thr
1               5

<210> SEQ ID NO 46
<211> LENGTH: 21
<212> TYPE: DNA
<213> ORGANISM: Homo sapiens

<400> SEQUENCE: 46
gatgcatcca aaagggccac t                                              21

<210> SEQ ID NO 47
<211> LENGTH: 9
<212> TYPE: PRT
<213> ORGANISM: Homo sapiens

<400> SEQUENCE: 47

His Gln Arg Gly Asn Trp Met Ser Ser
1               5

<210> SEQ ID NO 48
<211> LENGTH: 27
<212> TYPE: DNA
<213> ORGANISM: Homo sapiens

<400> SEQUENCE: 48
caccagcgtg gcaactggat gtctagt                                        27

<210> SEQ ID NO 49
<211> LENGTH: 17
<212> TYPE: PRT
<213> ORGANISM: Homo sapiens

<400> SEQUENCE: 49

Ile Ile Trp Tyr Asp Gly Ser Asn Lys Tyr Tyr Ala Asp Ser Val Lys
1               5                   10                  15

Gly

<210> SEQ ID NO 50
<211> LENGTH: 51
<212> TYPE: DNA
<213> ORGANISM: Homo sapiens

<400> SEQUENCE: 50
attatatggt atgatggaag taacaaatac tatgcagact ccgtgaaggg c              51

<210> SEQ ID NO 51
<211> LENGTH: 17
<212> TYPE: PRT
<213> ORGANISM: Homo sapiens

<400> SEQUENCE: 51

Lys Ser Ser Gln Ser Val Leu Tyr Ser Ser Asn Asn Lys Asn Tyr Leu
1               5                   10                  15

Val

<210> SEQ ID NO 52
<211> LENGTH: 51
<212> TYPE: DNA
<213> ORGANISM: Homo sapiens

<400> SEQUENCE: 52
aagtccagcc agagtgtttt atacagctcc aacaataaga actacttagt t              51

<210> SEQ ID NO 53

```
<211> LENGTH: 7
<212> TYPE: PRT
<213> ORGANISM: Homo sapiens

<400> SEQUENCE: 53

Trp Thr Ser Thr Arg Glu Ser
1               5

<210> SEQ ID NO 54
<211> LENGTH: 21
<212> TYPE: DNA
<213> ORGANISM: Homo sapiens

<400> SEQUENCE: 54
tggacatcta cccgggaatc c                                             21

<210> SEQ ID NO 55
<211> LENGTH: 5
<212> TYPE: PRT
<213> ORGANISM: Homo sapiens

<400> SEQUENCE: 55

Gly Tyr Tyr Ile Asn
1               5

<210> SEQ ID NO 56
<211> LENGTH: 15
<212> TYPE: DNA
<213> ORGANISM: Homo sapiens

<400> SEQUENCE: 56
ggctactata taaac                                                    15

<210> SEQ ID NO 57
<211> LENGTH: 17
<212> TYPE: PRT
<213> ORGANISM: Homo sapiens

<400> SEQUENCE: 57

Arg Ile Asn Pro Asn Ser Gly Gly Thr Asn Tyr Ala Gln Lys Phe Gln
1               5                   10                  15

Gly

<210> SEQ ID NO 58
<211> LENGTH: 51
<212> TYPE: DNA
<213> ORGANISM: Homo sapiens

<400> SEQUENCE: 58
cggatcaacc ctaacagtgg tggcacaaac tatgcacaga gtttcagggc              51

<210> SEQ ID NO 59
<211> LENGTH: 18
<212> TYPE: PRT
<213> ORGANISM: Homo sapiens

<400> SEQUENCE: 59

Trp Glu Gly Thr Val Thr Thr Trp Asp Phe Tyr Tyr Tyr Gly Met
1               5                   10                  15

Asp Val

<210> SEQ ID NO 60
<211> LENGTH: 54
```

```
<212> TYPE: DNA
<213> ORGANISM: Homo sapiens

<400> SEQUENCE: 60
tgggagggaa cggtgactac gtgggatttc tactattact acggtatgga cgtc        54

<210> SEQ ID NO 61
<211> LENGTH: 14
<212> TYPE: PRT
<213> ORGANISM: Homo sapiens

<400> SEQUENCE: 61

Thr Gly Thr Ser Ser Asp Val Asp Thr Tyr Asn Tyr Val Ser
1               5                   10

<210> SEQ ID NO 62
<211> LENGTH: 42
<212> TYPE: DNA
<213> ORGANISM: Homo sapiens

<400> SEQUENCE: 62
actggaacca gcagtgacgt tgatacttat aactatgtct cc                    42

<210> SEQ ID NO 63
<211> LENGTH: 7
<212> TYPE: PRT
<213> ORGANISM: Homo sapiens

<400> SEQUENCE: 63

Asp Val Ser Asn Arg Pro Ser
1               5

<210> SEQ ID NO 64
<211> LENGTH: 21
<212> TYPE: DNA
<213> ORGANISM: Homo sapiens

<400> SEQUENCE: 64
gatgtcagta atcggccctc a                                            21

<210> SEQ ID NO 65
<211> LENGTH: 11
<212> TYPE: PRT
<213> ORGANISM: Homo sapiens

<400> SEQUENCE: 65

Ser Ser Tyr Thr Ser Ser Ser Thr Leu Val Val
1               5                   10

<210> SEQ ID NO 66
<211> LENGTH: 33
<212> TYPE: DNA
<213> ORGANISM: Homo sapiens

<400> SEQUENCE: 66
agctcatata caagcagcag cactctcgtg gta                               33

<210> SEQ ID NO 67
<211> LENGTH: 18
<212> TYPE: PRT
<213> ORGANISM: Homo sapiens

<400> SEQUENCE: 67

Arg Ile Tyr Ser Arg Ser Lys Trp Tyr His Asp Tyr Ala Val Ser Val
```

```
1               5                   10                  15
Lys Gly

<210> SEQ ID NO 68
<211> LENGTH: 54
<212> TYPE: DNA
<213> ORGANISM: Homo sapiens

<400> SEQUENCE: 68
aggatatact ccaggtccaa gtggtatcat gattatgcag tatctgtgaa aggt          54

<210> SEQ ID NO 69
<211> LENGTH: 21
<212> TYPE: PRT
<213> ORGANISM: Homo sapiens

<400> SEQUENCE: 69

Asp Trp Glu Thr Ile Ile Trp Gly Asp Asp Gly Pro Asn Tyr Tyr Asn
1               5                   10                  15

Tyr Gly Leu Asp Val
            20

<210> SEQ ID NO 70
<211> LENGTH: 63
<212> TYPE: DNA
<213> ORGANISM: Homo sapiens

<400> SEQUENCE: 70
gattgggaga ccattatctg gggcgacgac ggtcccaact actacaacta cggtttggac    60
gtc                                                                 63

<210> SEQ ID NO 71
<211> LENGTH: 9
<212> TYPE: PRT
<213> ORGANISM: Homo sapiens

<400> SEQUENCE: 71

Leu Gln His Asn Asn Tyr Leu Trp Thr
1               5

<210> SEQ ID NO 72
<211> LENGTH: 27
<212> TYPE: DNA
<213> ORGANISM: Homo sapiens

<400> SEQUENCE: 72
ctacagcata ataattacct gtggacg                                       27

<210> SEQ ID NO 73
<211> LENGTH: 133
<212> TYPE: PRT
<213> ORGANISM: Homo sapiens

<400> SEQUENCE: 73

Gln Leu Asn Leu Gln Gln Ser Gly Pro Gly Leu Val Asn Pro Ser Gln
1               5                   10                  15

Thr Leu Ser Leu Thr Cys Ala Ile Ser Gly Gly Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Ser Arg Ser Lys Trp Tyr His Asp Tyr Ala
```

```
                    50                  55                  60
Val Ser Val Lys Gly Arg Ile Thr Ile Asn Pro Asp Thr Ser Lys Asn
 65                  70                  75                  80

Gln Phe Phe Leu Gln Leu Asn Ser Val Thr Pro Glu Asp Thr Ala Val
                 85                  90                  95

Tyr Tyr Cys Ala Arg Asp Trp Glu Thr Ser Ile Trp Asn Asp Asp Gly
            100                 105                 110

Pro Asn Tyr Tyr Asn Tyr Gly Met Asp Val Trp Gly Gln Gly Thr Thr
            115                 120                 125

Val Thr Val Ser Ser
        130

<210> SEQ ID NO 74
<211> LENGTH: 399
<212> TYPE: DNA
<213> ORGANISM: Homo sapiens

<400> SEQUENCE: 74
cagctaaacc tgcagcagtc aggtccagga ctggtgaacc cctcgcagac cctctcactc      60
acctgtgcca tctccggggg cagtgtctct agcaacagtg ctgcttggaa ctggatcagg     120
cagtccccgt cgagaggcct tgagtggctg ggaaggacat actccaggtc aagtggtat      180 catgattatg cagtatctgt gaaaggtcgg ataaccatca acccagacac atccaagaac     240
cagttcttcc tgcagctgaa ctctgtgact cccgaagaca cggctgtgta ttactgtgcg     300
agagattggg agacctctat ctggaacgac gacggtccca actactacaa ctacggtatg     360
gacgtctggg gccaagggac cacggtcacc gtctcctca                            399

<210> SEQ ID NO 75
<211> LENGTH: 107
<212> TYPE: PRT
<213> ORGANISM: Homo sapiens

<400> SEQUENCE: 75

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
             35                 40                  45

Tyr Gly Ala Ser Ser Leu Gln Ser Gly Val Pro Ser Arg Phe Ser Gly
     50                 55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Asn Tyr Pro Trp
                 85                  90                  95

Thr Phe Gly Gln Gly Thr Lys Val Glu Ile Lys
            100                 105

<210> SEQ ID NO 76
<211> LENGTH: 321
<212> TYPE: DNA
<213> ORGANISM: Homo sapiens

<400> SEQUENCE: 76
gacatccaga tgacccagtc tccatcctcc ctgtctgcat ctgtaggaga cagagtcacc      60
atcacttgcc gggcaagtca gggcattaga aatgatttag gctggtatca gcagaaacca     120
```
gggaaagccc ctaagcgcct gatctatggt gcatccagtt tgcaaagtgg ggtcccatca    180
aggttcagcg gcagtggatc tgggacagaa ttcactctca caatcagcag cctgcagcct    240
gaagattttg caacttatta ctgtctacag cataataatt acccgtggac gttcggccaa    300
gggaccaagg tggaaatcaa a    321

<210> SEQ ID NO 77
<211> LENGTH: 114
<212> TYPE: PRT
<213> ORGANISM: Homo sapiens

<400> SEQUENCE: 77

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Met
        35                  40                  45

Ala Val Ile Trp Tyr Asp Gly Thr Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser

<210> SEQ ID NO 78
<211> LENGTH: 342
<212> TYPE: DNA
<213> ORGANISM: Homo sapiens

<400> SEQUENCE: 78
caggtgcagc tggtggagtc tgggggaggc gtggtccagc ctgggaggtc cctgagactc    60
tcctgtgcag cgtctggatt caccttcagt agctatggca tgcactgggt ccgccaggct    120
ccaggcaagg ggctggagtg gatggcagtt atatggtatg atggaactaa taaatactat    180
gcagactccg tgaagggccg attcaccatc tccagagaca attccaagaa cacggtgtat    240
ctgcaaatga acagcctgag agccgaggac acggctgtgt attactgtgc gagagagaag    300
gggctggact ggggccaggg aaccctggtc accgtctcct ca    342

<210> SEQ ID NO 79
<211> LENGTH: 113
<212> TYPE: PRT
<213> ORGANISM: Homo sapiens

<400> SEQUENCE: 79

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Thr Asn Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys

<210> SEQ ID NO 80
<211> LENGTH: 339
<212> TYPE: DNA
<213> ORGANISM: Homo sapiens

<400> SEQUENCE: 80
gacatcgtga tgacccagtc tccagactcc ctggctgtgt ctctgggcga gagggccacc    60
atcaactgca gtccagcca gagtgtttta tacagctcca ccaataagaa ctacttagtt    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
ccgtggacgt tcggccaagg gaccaaggtg gaaatcaaa                           339

<210> SEQ ID NO 81
<211> LENGTH: 120
<212> TYPE: PRT
<213> ORGANISM: Homo sapiens

<400> SEQUENCE: 81

Glu Val Gln Met Leu Glu Ser Gly Gly Gly Leu Val Gln Pro Gly Gly
1               5                   10                  15

Ser Leu Arg Leu Ser Cys Ala Val Ser Gly Phe Thr Phe Ser Arg Phe
            20                  25                  30

Ala Met Ser Trp Val Arg Gln Ala Pro Gly Lys Gly Leu Asp Trp Val
        35                  40                  45

Ser Ser Ile Ser Asp Asn Ala Gly Arg Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Lys Leu Ser Asn Trp Gly Pro Tyr Gly Met Asp Val Trp Gly Gln
            100                 105                 110

Gly Thr Thr Val Thr Val Ser Ser
        115                 120

<210> SEQ ID NO 82
<211> LENGTH: 360
<212> TYPE: DNA
<213> ORGANISM: Homo sapiens

<400> SEQUENCE: 82
gaagtgcaga tgttggagtc tgggggaggc ttggtacagc ctggggggtc cctgagactc    60
tcctgtgcag tctctggatt cacctttagc agatttgcca tgagctgggt ccgccaggct    120
ccagggaagg ggctggactg ggtctcaagt attagtgaca atgctggtag acatacttc     180 gcagactccg tgaagggccg gttcaccatc tccagagaca attccaagaa cacgctgtat   240

```
ctgcaaatga acagcctgag agccgacgac acggccgtat attactgtgc gaaactctca    300
aactggggtc cttacggtat ggacgtctgg ggccaaggga ccacggtcac cgtctcctcg    360
```

<210> SEQ ID NO 83
<211> LENGTH: 111
<212> TYPE: PRT
<213> ORGANISM: Homo sapiens

<400> SEQUENCE: 83

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Tyr Tyr
            20                  25                  30

Asn Tyr Val Ser Trp Tyr Gln Gln His Pro Gly Glu Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Ser Thr Ala Ser Leu Thr Val Ser Gly Leu
65                  70                  75                  80

Gln Ala Val Asp Glu Ala Asp Tyr Tyr Cys Ser Ser Tyr Ala Gly Ser
                85                  90                  95

Lys Asn Phe Val Val Phe Gly Gly Gly Thr Lys Leu Thr Val Leu
            100                 105                 110
```

<210> SEQ ID NO 84
<211> LENGTH: 333
<212> TYPE: DNA
<213> ORGANISM: Homo sapiens

<400> SEQUENCE: 84

```
cagtctgccc tgactcagcc tccctccgcg tccgggtctc ctggacagtc agtcaccatc     60
tcctgcactg gaaccagcag tgacgttggt tattataact atgtctcctg gtaccaacag    120
cacccaggcg aagcccccaa actcatgatt tatgaggtca ataagcggcc ctcaggggtt    180
cctgatcgct tctctggctc caagtctggc agcacggcct ccctgaccgt ctctgggctc    240
caggctgtgg atgaggctga ttattactgc agctcatatg caggcagcaa aaatttgtg    300 gtattcggcg gagggaccaa gctgaccgtc cta                                  333
```

<210> SEQ ID NO 85
<211> LENGTH: 119
<212> TYPE: PRT
<213> ORGANISM: Homo sapiens

<400> SEQUENCE: 85

```
Ser Gln Val Gln Leu Gln Glu Ser Gly Pro Gly Leu Val Lys Pro Ser
1               5                   10                  15

Gly Thr Leu Ser Leu Thr Cys Ala Val Ser Gly Gly Ser Ile Arg Ser
            20                  25                  30

Tyr Asn Trp Trp Ser Trp Val Arg Gln Pro Pro Gly Glu Gly Leu Glu
        35                  40                  45

Trp Ile Gly Glu Ile His His Ser Gly Thr Thr Asn Tyr Asn Pro Ser
    50                  55                  60

Leu Lys Ser Arg Val Thr Ile Ser Val Asp Lys Ser Lys Asn Gln Phe
65                  70                  75                  80

Ser Leu Lys Leu Ser Ser Val Thr Ala Ala Asp Thr Ala Val Tyr Tyr
                85                  90                  95
```

Cys Ala Arg Asp Tyr Ser Gly Ser Tyr Phe Asp Tyr Trp Gly Gln Gly
            100                 105                 110

Thr Leu Val Thr Val Ser Ser
        115

<210> SEQ ID NO 86
<211> LENGTH: 357
<212> TYPE: DNA
<213> ORGANISM: Homo sapiens

<400> SEQUENCE: 86
tctcaggtgc agctgcagga gtcgggccca ggactggtga agccttcggg gaccctgtcc      60
ctcacctgcg ctgtctctgg tggctccatc aggagttata actggtggag ttgggtccgc     120
cagcccccag ggaggggct ggagtggatt ggggaaatcc atcatagtgg gaccaccaac      180
tacaacccgt ccctcaagag tcgagtcacc atatcggtag acaagtccaa gaaccagttc     240
tccctgaagc tgagctctgt gaccgccgcg gacacggccg tgtattactg tgcgagagat     300
tatagtggga gctactttga ctactgggc cagggaaccc tggtcaccgt ctcctca        357

<210> SEQ ID NO 87
<211> LENGTH: 107
<212> TYPE: PRT
<213> ORGANISM: Homo sapiens

<400> SEQUENCE: 87

Glu Val Val Leu Thr Gln Ser Pro Ala Thr Leu Ser Leu Ser Pro Gly
1               5                   10                  15

Glu Arg Ala Thr Leu Ser Cys Arg Thr Ser Gln Ser Leu Ser Ser Tyr
            20                  25                  30

Val Ala Trp Ser Gln Gln Lys Pro Gly Gln Ala Pro Arg Leu Leu Ile
        35                  40                  45

Tyr Asp Ala Ser Lys Arg Ala Thr Gly Val Pro Ala Arg Phe Ser Gly
    50                  55                  60

Ser Gly Ser Gly Thr Asp Phe Thr Leu Thr Ile Ser Asn Leu Glu Pro
65                  70                  75                  80

Glu Asp Phe Ala Val Tyr Tyr Cys His Gln Arg Gly Asn Trp Met Ser
                85                  90                  95

Ser Phe Gly Gln Gly Thr Lys Leu Glu Ile Lys
            100                 105

<210> SEQ ID NO 88
<211> LENGTH: 321
<212> TYPE: DNA
<213> ORGANISM: Homo sapiens

<400> SEQUENCE: 88
gaggttgtgt tgacacagtc tcccgccacc ctgtctttgt ctccagggga aagagccacc      60
ctctcctgca ggaccagtca gagtctaagc agctacgtag cctggtccca gcagaagcct     120
ggccaggctc ccaggctcct catctatgat gcatccaaaa gggccactgg cgtcccagcc     180
aggttcagtg gcagtgggtc tgggacagac ttcactctca ccatcagcaa cctagagcct     240
gaagattttg cagtttatta ctgtcaccag cgtggcaact ggatgtctag ttttggccag     300
gggaccaagc tggagatcaa a                                               321

<210> SEQ ID NO 89
<211> LENGTH: 114

```
<212> TYPE: PRT
<213> ORGANISM: Homo sapiens

<400> SEQUENCE: 89

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Glu Lys Gly Leu Asp Trp Gly Gln Gly Thr Leu Val Thr Val
            100                 105                 110

Ser Ser

<210> SEQ ID NO 90
<211> LENGTH: 342
<212> TYPE: DNA
<213> ORGANISM: Homo sapiens

<400> SEQUENCE: 90
caggtgcagc tggtggagtc tgggggaggc gtggtccagc ctggggaggtc cctgagactc      60 tcctgtgcag cgtctgggtt caccttcagt agctatggca tgcactgggt ccgccaggct     120
ccaggcaagg ggctggagtg ggtggcaatt atatggtatg atggaagtaa caaatactat     180
gcagactccg tgaagggccg attcaccatc tccagagaca attccaagaa cacgctgtat     240
ctgcaaatga acagcctgag agccgaggac acggctgtgt attactgtgt gagagagaag     300
gggctggact ggggccaggg aaccctggtc accgtctcct ca                        342

<210> SEQ ID NO 91
<211> LENGTH: 113
<212> TYPE: PRT
<213> ORGANISM: Homo sapiens

<400> SEQUENCE: 91

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys
```

<210> SEQ ID NO 92
<211> LENGTH: 339
<212> TYPE: DNA
<213> ORGANISM: Homo sapiens

<400> SEQUENCE: 92

| gacatcgtga tgacccagtc tccagactcc ctggctgtgt ctctgggcga gagggccacc | 60 |
| atcaactgca gtccagcca gagtgtttta tacagctcca acaataagaa ctacttagtt | 120 |
| tggtaccagc agaaaccagg acagcctcct aagctgctca tttactggac atctacccgg | 180 |
| gaatccgggg tccctgaccg attcagtggc agcgggtctg ggacagattt cactctcacc | 240 |
| atcagcagcc tgcaggctga agatgtggca gtttattact gtcagcaata ttatagtact | 300 |
| ccgtggacgt tcggccaagg gaccaaggtg gaaatcaaa | 339 |

<210> SEQ ID NO 93
<211> LENGTH: 127
<212> TYPE: PRT
<213> ORGANISM: Homo sapiens

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile Asn Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Phe Cys
                85                  90                  95

Ala Ser Trp Glu Gly Thr Val Thr Thr Trp Asp Phe Tyr Tyr Tyr Tyr
            100                 105                 110

Gly Met Asp Val Trp Gly Gln Gly Thr Thr Val Thr Val Ser Ser
        115                 120                 125

<210> SEQ ID NO 94
<211> LENGTH: 381
<212> TYPE: DNA
<213> ORGANISM: Homo sapiens

<400> SEQUENCE: 94

| caggtgcagt tggtgcagtc tggggctgag gtgaagaagc ctggggcctc agtgaaggtc | 60 |
| tcctgcaagg cttccggata caccttcacc ggctactata taaactgggt gcgacaggcc | 120 |
| cctggacaag gcttgagtg gatgggacgg atcaacccta acagtggtgg cacaaactat | 180 |
| gcacagaagt tcagggcag ggtcaccatg accaggaca cgtccatcaa cacagcctac | 240 |
| atggagctga gcaggctgag atctgacgac acggccgtgt atttctgtgc gagttgggag | 300 |
| ggaacggtga ctacgtggga tttctactat tactacggta tggacgtctg gggccaaggg | 360 |
| accacggtca ccgtctcctc a | 381 |

<210> SEQ ID NO 95
<211> LENGTH: 111
<212> TYPE: PRT
<213> ORGANISM: Homo sapiens

<400> SEQUENCE: 95

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Asp Thr Tyr
            20                  25                  30

Asn Tyr Val Ser Trp Tyr Gln His Pro Gly Lys Ala Pro Lys Leu
        35                  40                  45

Ile Ile Phe Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Ser
                85                  90                  95

Ser Thr Leu Val Val Phe Gly Gly Gly Thr Lys Leu Thr Val Leu
            100                 105                 110

<210> SEQ ID NO 96
<211> LENGTH: 333
<212> TYPE: DNA
<213> ORGANISM: Homo sapiens

<400> SEQUENCE: 96
cagtctgccc tgactcagcc tgcctccgtg tctggatctc ctggacagtc gatcaccatc      60
tcctgcactg gaaccagcag tgacgttgat acttataact atgtctcctg gtaccaacat     120
cacccaggca agcccccaa gctcataatt tttgatgtca gtaatcggcc ctcagggggtt     180 tctaatcgct tctctggctc caaatctggc aacacggcct ccctgaccat ctctgggctc     240
caggctgagg acgaggctga ttattactgc agctcatata caagcagcag cactctcgtg     300
gtattcggcg gagggaccaa gctgaccgtc cta                                   333

<210> SEQ ID NO 97
<211> LENGTH: 133
<212> TYPE: PRT
<213> ORGANISM: Homo sapiens

<400> SEQUENCE: 97

Gln Leu Asn Leu Gln Gln Ser Gly Pro Gly Leu Val Asn Pro Ser Gln
1               5                   10                  15

Thr Leu Ser Leu Thr Cys Ala Ile Ser Gly Gly Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Ser Arg Ser Lys Trp Tyr His Asp Tyr Ala
    50                  55                  60

Val Ser Val Lys Gly Arg Ile Thr Ile Asn Pro Asp Thr Ser Lys Asn
65              70                  75                  80

Gln Phe Phe Leu Gln Leu Asn Ser Val Thr Pro Glu Asp Thr Ala Val
                85                  90                  95

Tyr Tyr Cys Ala Arg Asp Trp Glu Thr Ile Ile Trp Gly Asp Asp Gly
            100                 105                 110

Pro Asn Tyr Tyr Asn Tyr Gly Leu Asp Val Trp Gly Gln Gly Thr Thr
        115                 120                 125

Val Thr Val Ser Ser
    130

<210> SEQ ID NO 98
<211> LENGTH: 399
<212> TYPE: DNA
<213> ORGANISM: Homo sapiens

<400> SEQUENCE: 98

| | | |
|---|---|---|
| cagctaaacc tgcagcagtc aggtccagga ctggtgaacc cctcgcagac cctctcactc | 60 |
| acctgtgcca tctccggggg cagtgtctct agcaacagtg ctgcttggaa ctggatcagg | 120 |
| cagtccccgt cgagaggcct tgagtggctg gaaggatat actccaggtc caagtggtat | 180 |
| catgattatg cagtatctgt gaaaggtcgg ataaccatca cccagacac atccaagaac | 240 |
| cagttcttcc tgcagctgaa ctctgtgact cccgaagaca cggctgtgta ttactgtgca | 300 |
| agagattggg agaccattat ctggggcgac gacggtccca actactacaa ctacggtttg | 360 |
| gacgtctggg gccaagggac cacggtcacc gtctcctca | 399 |

<210> SEQ ID NO 99
<211> LENGTH: 107
<212> TYPE: PRT
<213> ORGANISM: Homo sapiens

<400> SEQUENCE: 99

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Lys Pro Gly Lys Ala Pro Lys Arg Leu Ile
        35                  40                  45
Tyr Gly Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Asn Tyr Leu Trp
                85                  90                  95
Thr Phe Gly Gln Gly Thr Lys Val Glu Ile Lys
            100                 105

<210> SEQ ID NO 100
<211> LENGTH: 321
<212> TYPE: DNA
<213> ORGANISM: Homo sapiens

<400> SEQUENCE: 100

| | | |
|---|---|---|
| gacatccaga tgacccagtc tccatcctcc ctgtctgcat ctgtaggaga cagagtcacc | 60 |
| atcacttgcc gggcaagtca gggcattaga aatgatttag ctggtatca gcagaaacca | 120 |
| gggaaagccc ctaagcgcct gatctatggt gcatccagtt tgcaaagtgg ggtcccatca | 180 |
| aggttcagcg gcagtggatc tgggacagaa ttcactctca caatcagcag cctgcagcct | 240 |
| gaagattttg caacttatta ctgtctacag cataataatt acctgtggac gttcggccaa | 300 |
| gggaccaagg tggaaatcaa a | 321 |

<210> SEQ ID NO 101
<211> LENGTH: 35
<212> TYPE: PRT
<213> ORGANISM: Homo sapiens

<400> SEQUENCE: 101

-continued

```
Cys Ala Arg Asp Trp Glu Thr Ser Ile Trp Asn Asp Asp Gly Pro Asn
1               5                   10                  15

Tyr Tyr Asn Tyr Gly Met Asp Val Trp Gly Gln Gly Thr Thr Val Thr
            20              25                  30

Val Ser Ser
        35
```

ANTI-PCSK9 ANTIBODIES

CROSS REFERENCE TO RELATED APPLICATIONS

The present application claims the priority of PCT application No. PCT/CN2016/099491 entitled "Novel anti-PCSK9 antibodies", filed on Sep. 20, 2016, the entirety of which is hereby incorporated by reference.

SEQUENCE LISTING

A copy of the Sequence Listing is submitted with the specification electronically via EFS-Web as an ASCII formatted sequence listing with a file name of "053674-8009US01-SL-20210104 ST25", a creation date of Jan. 4, 2021, and a size of 34,940 bytes. The sequence listing contained in this ASCII formatted document is part of the specification and is herein incorporated by reference in its entirety.

FIELD OF THE INVENTION

The present disclosure generally relates to novel anti-PCSK9 antibodies.

BACKGROUND

Cardiovascular diseases (CVD) remains the number one cause of death globally (World Health Organization (WHO), 2011. World Health Organization). Various studies have shown that lowering the low-density lipoprotein cholesterol (LDL-C) reduces the risk of CVD. There is a significantly medical need for CVD despite the treatment with statins, the current first choice of lipid lowering agents. A significant portion of patients is either unable to tolerate satisfactory doses or fail to achieve lipid control on statin therapy (Baigent, C. et al., Lancet 2000, 376(9753), 1670-1681).

Proprotein Convertase Subtilisin/Kexin type 9 (PCSK9) was originally discovered as neural apoptosis regulated convertase-1. It is primarily synthesized in the small intestine and liver (Seidah N G et al., Proc Natl Acad Sci USA 2003; 100:928-33). Mature PCSK9 is secreted from the liver cells after intracellular autocatalytic cleavage of its prodomain (McNutt, M. C. et al., J. Biol. Chem. 2007, 20(282), 20799-20803). The important role of PCSK9 in regulating cholesterol metabolism was firstly found by the recognition of two gain-of function mutations in PCSK9 in two French families with autosomal dominant hypercholesterolemia (Abifadel M et al., Nat Genet 2003; 34:154-6). PCSK9 regulates cholesterol metabolism mainly by binding to the low-density lipoprotein receptor (LDLR) for degradation in liver. In the absence of PCSK9, the hepatic LDLR is recycled back to the cell membrane after delivering LDL-C to the lysozyme for degradation. Binding of PCSK9 and LDLR prevents the normal recycling of LDLR and instead enhances the LDLR degradation (Verbeek, R., et al., Eur J Pharmacol 2015; Lo Surdo Petal., EMBO Rep 2011; 12:1300-5).

Several therapeutic approaches to inhibit PCSK9 are in development, including direct inhibition of PCSK9 binding to LDLR by antibody or peptides; inhibition of PCSK9 synthesis by gene silencing agents and inhibition of PCSK9 intracellular production by small molecules (MICHEL FARNIER, ARCHIVES OF CARDIOVASCULAR DISEASE, 2014, 107, 58-66). The recently approved monoclonal antibodies Alirocumab and Evolocumab have shown promising efficacy of LDL-C reduction in phase II and phase III clinical studies. Current evidence shows up to 70% reduction in LDL-C levels independent of background Statin therapy (Dias, C. S et al., J. Am. Coll. Cardiol. 2012, 60(19), 1888-1898; Giugliano, R. P et al., Lancet, 2012, 380(9858), 2007-2017; McKenney, J. M et al., J. Am. Coll. Cardiol. 2012, 59(25), 2344-2353).

BRIEF SUMMARY OF THE INVENTION

The present disclosure provides novel monoclonal anti-PCSK9 antibodies (in particular fully human antibodies), polynucleotides encoding the same, and methods of using the same.

In one aspect, the present disclosure provides isolated monoclonal antibodies or antigen binding fragments thereof, comprising a heavy chain CDR sequences selected from the group consisting of: SEQ ID NOs: 1, 3, 5, 13, 15, 17, 25, 27, 29, 37, 39, 41, 49, 55, 57, 59, 67 and 69.

In certain embodiments, the antibodies or antigen binding fragments thereof comprises a light chain CDR sequences selected from the group consisting of: SEQ ID NOs: 7, 9, 11, 19, 21, 23, 31, 33, 35, 43, 45, 47, 51, 53, 61, 63, 65 and 71.

In certain embodiments, the antibodies or antigen binding fragments thereof comprises a heavy chain variable region selected from the group consisting of:
 a) a heavy chain variable region comprising SEQ ID NO: 1, SEQ ID NO: 3, and/or SEQ ID NO: 5;
 b) a heavy chain variable region comprising SEQ ID NO: 13, SEQ ID NO: 15, and/or SEQ ID NO: 17;
 c) a heavy chain variable region comprising SEQ ID NO: 25, SEQ ID NO: 27, and/or SEQ ID NO: 29;
 d) a heavy chain variable region comprising SEQ ID NO: 37, SEQ ID NO: 39, and/or SEQ ID NO: 41;
 e) a heavy chain variable region comprising SEQ ID NO: 13, SEQ ID NO: 49, and/or SEQ ID NO: 17;
 f) a heavy chain variable region comprising SEQ ID NO: 55, SEQ ID NO: 57, and/or SEQ ID NO: 59; and
 g) a heavy chain variable region comprising SEQ ID NO: 1, SEQ ID NO: 67, and/or SEQ ID NO: 69.

In certain embodiments, the antibodies or antigen binding fragments thereof comprises a light chain variable region selected from the group consisting of:
 a) a light chain variable region comprising SEQ ID NO: 7, SEQ ID NO: 9, and/or SEQ ID NO: 11;
 b) a light chain variable region comprising SEQ ID NO: 19, SEQ ID NO: 21, and/or SEQ ID NO: 23;
 c) a light chain variable region comprising SEQ ID NO: 31, SEQ ID NO: 33, and/or SEQ ID NO: 35;
 d) a light chain variable region comprising SEQ ID NO: 43, SEQ ID NO: 45, and/or SEQ ID NO: 47;
 e) a light chain variable region comprising SEQ ID NO: 51, SEQ ID NO: 53, and/or SEQ ID NO: 23;
 f) a light chain variable region comprising SEQ ID NO: 61, SEQ ID NO: 63, and/or SEQ ID NO: 65; and
 g) a light chain variable region comprising SEQ ID NO: 7, SEQ ID NO: 9, and/or SEQ ID NO: 71.

In certain embodiments, the antibodies or antigen binding fragments thereof comprises:
 a) a heavy chain variable region comprising SEQ ID NO: 1, SEQ ID NO: 3, and/or SEQ ID NO: 5; and a light chain variable region comprising SEQ ID NO: 7, SEQ ID NO: 9, and/or SEQ ID NO: 11;
 b) a heavy chain variable region comprising SEQ ID NO: 13, SEQ ID NO: 15, and/or SEQ ID NO: 17; and a light chain variable region comprising SEQ ID NO: 19, SEQ ID NO: 21, and/or SEQ ID NO: 23;

c) a heavy chain variable region comprising SEQ ID NO: 25, SEQ ID NO: 27, and/or SEQ ID NO: 29; and a light chain variable region comprising SEQ ID NO: 31, SEQ ID NO: 33, and/or SEQ ID NO: 35;

d) a heavy chain variable region comprising SEQ ID NO: 37, SEQ ID NO: 39, and/or SEQ ID NO: 41; and a light chain variable region comprising SEQ ID NO: 43, SEQ ID NO: 45, and/or SEQ ID NO: 47;

e) a heavy chain variable region comprising SEQ ID NO: 13, SEQ ID NO: 49, and/or SEQ ID NO: 17; and a light chain variable region comprising SEQ ID NO: 51, SEQ ID NO: 53, and/or SEQ ID NO: 23;

f) a heavy chain variable region comprising SEQ ID NO: 55, SEQ ID NO: 57, and/or SEQ ID NO: 59; and a light chain variable region comprising SEQ ID NO: 61, SEQ ID NO: 63, and/or SEQ ID NO: 65; or g) a heavy chain variable region comprising SEQ ID NO: 1, SEQ ID NO: 67, and/or SEQ ID NO: 69; and a light chain variable region comprising SEQ ID NO: 7, SEQ ID NO: 9, and/or SEQ ID NO: 71.

In certain embodiments, the antibodies or antigen binding fragments thereof comprises a heavy chain variable region selected from the group consisting of: SEQ ID NO: 73, SEQ ID NO: 77, SEQ ID NO: 81, SEQ ID NO: 85, SEQ ID NO: 89, SEQ ID NO: 93, and SEQ ID NO: 97 and the homologue sequences of at least 80% (e.g. at least 85%, 88%, 90%, 91%, 92%, 93%, 94%, 95%, 96%, 97%, 98% or 99%) sequence identity thereof.

In certain embodiments, the antibodies or antigen binding fragments thereof comprises a light chain variable region selected from the group consisting of: SEQ ID NO: 75, SEQ ID NO: 79, SEQ ID NO: 83, SEQ ID NO: 87, SEQ ID NO: 91, SEQ ID NO: 95, and SEQ ID NO: 99 and the homologue sequences of at least 80% (e.g. at least 85%, 88%, 90%, 91%, 92%, 93%, 94%, 95%, 96%, 97%, 98% or 99%) sequence identity thereof.

In certain embodiments, the antibodies or antigen binding fragments thereof comprises:

a) a heavy chain variable region comprising SEQ ID NO: 73 and a light chain variable region comprising SEQ ID NO: 75;

b) a heavy chain variable region comprising SEQ ID NO: 77 and a light chain variable region comprising SEQ ID NO: 79;

c) a heavy chain variable region comprising SEQ ID NO: 81 and a light chain variable region comprising SEQ ID NO: 83;

d) a heavy chain variable region comprising SEQ ID NO: 85 and a light chain variable region comprising SEQ ID NO: 87;

e) a heavy chain variable region comprising SEQ ID NO: 89 and a light chain variable region comprising SEQ ID NO: 91;

f) a heavy chain variable region comprising SEQ ID NO: 93 and a light chain variable region comprising SEQ ID NO: 95;

g) a heavy chain variable region comprising SEQ ID NO: 97 and a light chain variable region comprising SEQ ID NO: 99; or h) a heavy chain variable region and a light chain variable region of at least 80% (e.g. at least 85%, 88%, 90%, 91%, 92%, 93%, 94%, 95%, 96%, 97%, 98% or 99%) sequence identity to a), b), c), d), d), f), or g).

In certain embodiments, the antibodies or antigen binding fragments thereof is capable of specifically binding to human PCSK9 at a KD value no more than $10^{-7}$ M, no more than $10^{-8}$ M, no more than $10^{-9}$ M, or no more than $10^{-10}$ M, no more than $10^{-11}$ M, no more than $10^{-12}$ M, as measured by surface plasmon resonance (SPR) binding assay.

In certain embodiments, the antibodies or antigen binding fragments thereof is capable of specifically binding to human PCSK9 at a KD value no more than $10^{-7}$ M, no more than $10^{-8}$ M, no more than $10^{-9}$ M, no more than $10^{-10}$ M, no more than $10^{-11}$ M, no more than $10^{-12}$ M, as measured by ELISA assay.

In certain embodiments, the antibodies or antigen binding fragments thereof binds to monkey PCSK9 at a KD value no more than $10^{-7}$ M, no more than $10^{-8}$ M, no more than $10^{-9}$ M, no more than $10^{-10}$ M, no more than $10^{-11}$ M, no more than $10^{-12}$ M.

In certain embodiments, the antibodies or antigen binding fragments thereof is capable of inhibiting binding of human PCSK9 to its ligand at an IC50 of no more than 2.1 nM (e.g. no more than 3 nM, 2.5 nM, 1.8 nM, 1.7 nM, 1.6 nM, 1.5 nM, 1.4 nM, 1.3 nM, 1.2 nM, or 1 nM). In certain embodiments, the antibodies or antigen binding fragments thereof is capable of binding to human PCSK9 at an EC50 of no more than 0.15 nM (e.g. no more than 0.14, 0.13, 0.12, 0.11, 0.1, 0.09, 0.08, 0.07, 0.06, 0.05, 0.04, 0.03 or 0.02 nM).

In certain embodiments, the antibodies or antigen binding fragments thereof is capable of restoring cellular LDL uptake at an IC50 of no more than 115 nM, no more than 106 nM, no more than 80 nM, no more than 77 nM, no more than 66 nM or no more than 40 nM (e.g. no more than 120 nM, 110 nM, 100 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 11 nM, 10 nM, 9 nM, 8 nM, 7 nM, 6 nM, 5 nM, 4 nM, 3 nM, 2 nM, or 1 nM).

In certain embodiments, the antibodies or antigen binding fragments thereof is stable in serum for at least 1 day, at least 3 days, at least 4 days, at least 5 days, at least one week, at least two weeks, or at least one month.

In certain embodiments, the antibodies or antigen binding fragments thereof does not mediate ADCC or CDC or both.

In certain embodiments, the antibodies or antigen binding fragments thereof is a fully human monoclonal antibody. In certain embodiments, the fully human monoclonal antibody is produced by a host cell or a transgenic animal.

In certain embodiments, the antibodies or antigen binding fragments thereof is capable of reducing LDL-cholesterol up to 10%, 15%, 20%, 25%, 30%, 35%, 40%, 45%, 50%, 55%, 60%, 65%, 70%, 75%, 77%, 80%, 84%, 85%, 90%, 95% or more in an animal. In certain embodiments, the antibodies or antigen binding fragments thereof is capable of maintaining the level of HDL-cholesterol.

In certain embodiments, the antibodies or antigen binding fragments thereof has a serum half-life of at least 165 hours, at least 250 hours, at least 360 hours, at least 390 hours, or at least 450 hours (e.g. at least 50, at least 60, at least 70, at least 80, at least 90, at least 100, at least 150, at least 180, at least 200, at least 300, at least 350, at least 400, or at least 500 hours).

In one aspect, the present disclosure provides an antibody or an antigen binding fragment thereof, which competes for the same epitope with the antibody or the antigen binding fragment thereof provided herein.

In certain embodiments, the antibodies or antigen binding fragments thereof is a camelized single domain antibody, a diabody, a scFv, an scFv dimer, a BsFv, a dsFv, a (dsFv)2, a dsFv-dsFv', an Fv fragment, a Fab, a Fab', a F(ab')2, a ds diabody, a nanobody, a domain antibody, or a bivalent domain antibody.

In certain embodiments, the antibodies or antigen binding fragments thereof further comprises an immunoglobulin constant region.

In certain embodiments, the antibodies or antigen binding fragments thereof further comprises a conjugate. In certain embodiments, the conjugate can be a detectable label, a pharmacokinetic modifying moiety, or a purification moiety.

In one aspect, the present disclosure further provides an isolated polynucleotide encoding the antibody or an antigen binding fragment thereof provided herein. The present disclosure further provides a vector comprising said isolated polynucleotide. The present disclosure further provides a host cell comprising said vector. In certain embodiments, the polynucleotides provided herein are operably associated with a promoter such as a SV40 promoter in a vector. In certain embodiments, host cells comprising the vectors provided herein are Chinese hamster ovary cell, or 293 cell.

In one aspect, the present disclosure further provides a method of expressing the antibody or antigen-binding fragment thereof provided herein, comprising culturing said host cell under the condition at which said polynucleotide is expressed.

In one aspect, the present disclosure further provides a kit comprising the antibody or antigen-binding fragment thereof of provided herein.

In one aspect, the present disclosure further provides a method of treating a disease or condition mediated by PCSK9 in an individual, comprising: administering a therapeutically effective amount of antibody or antigen-binding fragment thereof of provided herein to the individual. In certain embodiments, the individual has been identified as upregulated level of serum LDL cholesterol, total cholesterol and/or non-HDL cholesterol or downregulated level of LDL receptor in a test biological sample from the individual. In certain embodiments, upon administration of said antibody or antigen-binding fragment thereof, the level of LDL-C and/or total cholesterol is reduced.

In one aspect, the present disclosure further provides a pharmaceutical composition comprising the antibody or antigen-binding fragment thereof of provided herein and one or more pharmaceutically acceptable carriers. In certain of these embodiments, the pharmaceutical carriers may be, for example, diluents, antioxidants, adjuvants, excipients, or non-toxic auxiliary substances.

In one aspect, the present disclosure further provides a method of treating a condition in a subject that would benefit from upregulation of immune response, comprising administering a therapeutically effective amount of the antibody or antigen-binding fragment thereof of provided herein to the subject. In certain embodiments, the subject has upregulated level of serum LDL cholesterol, total cholesterol and/or non-HDL cholesterol or downregulated level of LDL receptor.

In one aspect, the present disclosure further provides use of the antibody or antigen-binding fragment thereof provided herein in the manufacture of a medicament for treating a condition that would benefit from upregulation of immune response. In certain embodiments, the condition is cardiovascular diseases, inflammatory diseases, and infectious diseases. In certain embodiments, the infectious disease is sepsis.

BRIEF DESCRIPTION OF FIGURES

FIG. 1 presents the selected mutations in the CDR3 of the heavy chains of 11.4. 11.4 HCDR3 (i.e. SEQ ID NO: 5) is located between (i.e. from position 4-24 of SEQ ID NO: 101) the framework region. Amino acid "S" at location 5 of 11.4 HCDR3 can be mutated to R, T, M, I, K, Q, L or V, amino acid "N" at location 8 of 11.4 HCDR3 can be mutated to G or S, amino acid "P" at location 12 of 11.4 HCDR3 can be mutated to R and amino acid "M" at location 19 of 11.4 HCDR3 can be mutated to F or L, which creates a library of mutation in the CDR3 of the heavy chains of 11.4.

FIG. 20A shows the result of a single dose of 10 mg/kg injection, and FIG. 20B shows the result of a single dose of 30 mg/kg injection.

FIG. 21 shows High Density Lipoprotein cholesterol (HDL-C) change percentage of antibody 18, 156.8, 40409 and BMK.115 treated cynomolgus monkeys. FIG. 21B shows the result of a single dose of 30 mg/kg injection.

FIG. 22 shows LDL-C change percentage of antibody 15.14.2, 19.3.8, 17.72.3, 18.136.7 and REPATHA™ treated cynomolgus monkeys. FIG. 22A shows the result of a single dose of 3 mg/kg injection, and FIG. 22B shows the result of a single dose of 10 mg/kg injection.

FIG. 23A shows the result of a single dose of 3 mg/kg injection, and FIG. 23B shows the result of a single dose of 10 mg/kg injection.

FIG. 24 shows antibody concentration of 18.156.8, 40409 or BMK.115 of predose and postdose in cynomolgus monkey serum, as measured by ELISA. FIG. 24B shows the result of a single dose of 30 mg/kg injection.

FIG. 25 shows antibody concentration of 15.14.2(hIgG4), 19.3.8(hIgG4), 17.72.3(hIgG4), 18.136.7(hIgG4) or REPATHA™ of predose and postdose in cynomolgus monkey serum, as measured by ELISA. FIG. 25A shows the result of a single dose of 3 mg/kg injection, and FIG. 25B shows the result of a single dose of 10 mg/kg injection.

FIGS. 26A, 26C and 26E show the result of a single dose of 10 mg/kg injection, and FIGS. 26B, 26D and 26F show the result of a single dose of 30 mg/kg injection.

FIG. 27 shows ADA against 15.14.2, 19.3.8, 17.72.3, 18.136.7 or REPATHA™ in cynomolgus monkey serum samples of predose and postdose. FIGS. 27A, 27C, 27E, 27G and 27I show the result of a single dose of 3 mg/kg injection, and FIGS. 27B, 27D, 27F, 27H and 27J show the result of a single dose of 10 mg/kg injection.

FIGS. 28A, 28B and 28C show the result of generation of reference antibodies 12H11.1 and 24B9.1. FIG. 28A presents results of SDS-PAGE of 12H11.1.uIgG4K and 24B9.1.uIgG4L. M: Protein Marker; Lane1: 24B9.1.uIgG4L, reduced; Lane2: 12H11.1.uIgG4K, reduced; Lane3: 24B9.1.uIgG4L, non-reduced; Lane4: 12H11.1.uIgG4K, non-reduced. FIGS. 28B and 28C reveal the HPLC-SEC detection of 24B9.1.uIgG4L and 12H11.1.uIgG4K.

DETAILED DESCRIPTION OF THE INVENTION

Figure 2:
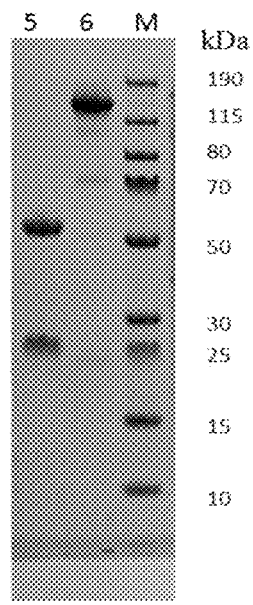
FIG. 2 shows the staining of fully human antibody 18.156.8 (hIgG4) in SDS-PAGE gel. M: Protein Marker; Lane5: 18.156.8 (hIgG4), Reduced; Lane6: 18.156.8 (hIgG4), Non-reduced.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multispecific antibody, or bispecific (bivalent) antibody that binds to a specific antigen. A native intact antibody comprises two heavy chains and two light chains. Each heavy chain consists of a variable region and a first, second, and third constant region, while each light chain consists of a variable region and a constant region. Mammalian heavy chains are classified as $\alpha$, $\delta$, $\epsilon$, $\gamma$, and $\mu$, and mammalian light chains are classified as $\lambda$, or $\kappa$. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variables region in both chains generally contain three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Kabat, Chothia, or Al-Lazikani (Al-Lazikani, B., Chothia, C., Lesk, A. M., J. Mol. Biol., 273(4), 927 (1997); Chothia, C. et al., J Mol Biol. Dec. 5; 186(3):651-63 (1985); Chothia, C. and Lesk, A. M., J.Mol.Biol., 196,901 (1987); Chothia, C. et al., Nature. Dec. 21-28; 342(6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of $\alpha$, $\delta$, $\epsilon$, $\gamma$, and $\mu$ heavy chains, respectively. Several of the major antibody classes are divided into subclasses such as IgG1 ($\gamma$1 heavy chain), IgG2 ($\gamma$2 heavy chain), IgG3 ($\gamma$3 heavy chain), IgG4 ($\gamma$4 heavy chain), IgA1 ($\alpha$1 heavy chain), or IgA2 ($\alpha$2 heavy chain).

The term "antigen-binding fragment" as used herein refers to an antibody fragment formed from a portion of an antibody comprising one or more CDRs, or any other antibody fragment that binds to an antigen but does not comprise an intact native antibody structure. Examples of antigen-binding fragment include, without limitation, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, and a bivalent domain antibody. An antigen-binding fragment is capable of binding to the same antigen to which the parent antibody binds. In certain embodiments, an antigen-binding fragment may comprise one or more CDRs from a particular human antibody grafted to a framework region from one or more different human antibodies.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'.

"Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as ADCC, and CDC, but does not function in antigen binding.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Huston J S et al. Proc Natl Acad Sci USA, 85:5879(1988)). "Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann L. and Muyldermans S., J Immunol Methods. Dec. 10; 231(1-2):25-38 (1999); Muyldermans S., J Biotechnol. Jun.; 74(4):277-302 (2001); WO94/04678; WO94/25591; U.S. Pat. No. 6,005, 079). Heavy chain antibodies were originally derived from Camelidae (camels, dromedaries, and llamas). Although devoid of light chains, camelized antibodies have an authentic antigen-binding repertoire (Hamers-Casterman C. et al., Nature. Jun. 3; 363(6428):446-8 (1993); Nguyen V K. et al. "Heavy-chain antibodies in Camelidae; a case of evolutionary innovation," Immunogenetics. Apr.; 54(1):39-47 (2002); Nguyen V K. et al. Immunology. May; 109(1):93-101 (2003)). The variable domain of a heavy chain antibody (VHH domain) represents the smallest known antigen-binding unit generated by adaptive immune responses (Koch-Nolte F. et al., FASEB J. Nov.; 21(13):3490-8. Epub 2007 Jun. 15 (2007)).

A "nanobody" refers to an antibody fragment that consists of a VHH domain from a heavy chain antibody and two constant domains, CH2 and CH3.

"Diabodies" include small antibody fragments with two antigen-binding sites, wherein the fragments comprise a $V_H$ domain connected to a $V_L$ domain in the same polypeptide chain ($V_H$-$V_L$ or $V_L$-$V_H$) (see, e.g., Holliger P. et al., Proc Natl Acad Sci USA. Jul. 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same of different antigens (or epitopes).

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

In certain embodiments, a "(dsFv)$_2$" comprises three peptide chains: two $V_H$ moieties linked by a peptide linker and bound by disulfide bridges to two $V_L$ moieties.

In certain embodiments, a "bispecific ds diabody" comprises $V_{H1}$-$V_{L2}$ (linked by a peptide linker) bound to $V_{L1}$-$V_{H2}$ (also linked by a peptide linker) via a disulfide bridge between $V_{H1}$ and $V_{L1}$.

In certain embodiments, a "bispecific dsFv" or dsFv-dsFv'" comprises three peptide chains: a $V_{H1}$-$V_{H2}$ moiety wherein the heavy chains are linked by a peptide linker (e.g., a long flexible linker) and bound to $V_{L1}$ and $V_{L2}$ moieties, respectively, via disulfide bridges, wherein each disulfide paired heavy and light chain has a different antigen specificity.

In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or eptipoes) or different antigens (or eptipoes). In other embodiments, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

The term "fully human" as used herein, with reference to antibody or antigen-binding fragment, means that the antibody or the antigen-binding fragment has or consists of amino acid sequence(s) corresponding to that of an antibody produced by a human or a human immune cell, or derived from a non-human source such as a transgenic non-human animal that utilizes human antibody repertoires or other human antibody-encoding sequences. In certain embodiments, a fully human antibody does not comprise amino acid residues (in particular antigen-binding residues) derived from a non-human antibody.

The term "humanized" as used herein, with reference to antibody or antigen-binding fragment, means that the antibody or the antigen-binding fragment comprises CDRs derived from non-human animals, FR regions derived from human, and when applicable, the constant regions derived from human. A humanized antibody or antigen-binding fragment is useful as human therapeutics in certain embodiments because it has reduced immunogenicity in human. In some embodiments, the non-human animal is a mammal, for example, a mouse, a rat, a rabbit, a goat, a sheep, a guinea pig, or a hamster. In some embodiments, the humanized antibody or antigen-binding fragment is composed of substantially all human sequences except for the CDR sequences which are non-human. In some embodiments, the FR regions derived from human may comprise the same amino acid sequence as the human antibody from which it is derived, or it may comprise some amino acid changes, for example, no more than 10, 9, 8, 7, 6, 5, 4, 3, 2, or 1 changes of amino acid. In some embodiments, such change in amino acid could be present in heavy chain FR regions only, in light chain FR regions only, or in both chains. In some preferable embodiments, the humanized antibodies comprise human FR1-3 and human JH and Jκ.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human species, such as from mouse.

"PCSK9" as used herein refers to Proprotein Convertase Subtilisin/Kexin type 9, a naturally-occurring human proprotein convertase belonging to the proteinase K subfamily of the secretory subtilase family. PCSK9 is synthesized as a soluble zymogen that undergoes autocatalytic intramolecular processing in the endoplasmic reticulum, and is thought to function as a proprotein convertase. PCSK9 has critical role in regulating blood cholesterol levels. Gain of function mutations of PCSK9 (such as S127R, F216L, and D374Y) may associate with a form of autosomal dominant familial hypercholesterolemia, in which PCSK9 mutants enhance the level of LDL receptor. See, e.g., Burnett and Hooper, Clin Biochem Rev (2008) 29(1): 11-26, Benjannet et al. J. Biol. Chem., (2004) 279(47):48865-48875 and Fasano T et al., Atherosclerosis. (2009) 203(1):166-71. Representative amino acid sequence of human PCSK9 is disclosed under the GENBANK' accession number: NP 777596.2, and the representative mRNA nucleic acid sequence encoding the human PCSK9 is shown under the GENBANK' accession number: FJ525880.1. In certain embodiments, the term PCSK9 encompasses PCSK9 molecules of post-translational modifications of the PCSK9 amino acid sequence, such as glycosylated, PEGylated PCSK9 sequences, PCSK9 sequences with its signal sequence being cleaved, or PCSK9 sequence with its pro domain being cleaved from the catalytic domain but not separated from the catalytic domain.

"LDL-C" as used herein refers to low-density lipoprotein cholesterol and "HDL-C" refers to high-density lipoprotein cholesterol. LDL and HDL are within the five major groups of lipoprotein: chylomicrons, very low-density lipoprotein (VLDL), intermediate-density lipoprotein (IDL), low-density lipoprotein and high-density lipoprotein (HDL) (in the order from the largest particles to most dense (smallest particles). LDL ("bad" cholesterol containing particle) can transport lipid/sterol molecules, such as cholesterol (i.e. LDL-C) into artery walls, attract macrophages thus triggering atherosclerosis. In contrast, HDL ("good" cholesterol containing particle) can remove lipid molecules, such as cholesterol (i.e. HDL-C) from macrophages in the wall of arteries. Thus, high level of LDL-C has been a major risk of cardiovascular diseases (CVDs), such as peripheral artery disease, coronary artery diseases (CAD, such as angina and myocardial infarction (commonly known as a heart attack), hyperlipidemia, hypercholesterolemia, or hypertriglyceridemia), atherosclerosis, stroke, hypertensive heart disease, rheumatic heart disease, cardiomyopathy, heart arrhythmia, congenital heart disease, valvular heart disease, carditis, aortic aneurysms, peripheral artery disease, obesity, cholestatic liver disease, nephrotic syndrome, hypothyroidism and venous thrombosis, or a combination thereof.

"LDL-R" or "LDL receptor" is a mosaic cell-surface protein of 839 amino acids (after removal of 21-amino acid signal peptide) that mediates the endocytosis of LDL-C and removes LDL-C from the blood. Representative amino acid sequence of human LDL-R is disclosed under the GEN-BANK™ accession number: P01130.1, and the representative mRNA nucleic acid sequence encoding the human LDL-R is shown under the GENBANK™ accession number: NM_000527.4. When PCSK9 binds to the LDL receptor, the receptor is broken down and cannot remove LDL-C from the blood. In contrary, when PCSK9 is blocked, more LDL receptors will be present on the surface of the liver and will remove more LDL cholesterol from the blood. "Anti-PCSK9 antibody" as used herein refers to an antibody that is capable of specific binding to PCSK9 (e.g. human or monkey PCSK9) with an affinity which is sufficient to provide for diagnostic and/or therapeutic use.

The term "specific binding" or "specifically binds" as used herein refers to a non-random binding reaction between two molecules, such as for example between an antibody and an antigen. In certain embodiments, the antibodies or antigen-binding fragments provided herein specifically bind human and/or PCSK9 with a binding affinity ($K_D$) of $\leq 10^{-6}$ M (e.g., $\leq 5\times 10^{-7}$ M, $\leq 2\times 10^{-7}$ M, $\leq 10^{-7}$ M, $\leq 5\times 10^{-8}$ M, $\leq 2\times 10^{-8}$ M, $\leq 10^{-8}$ M, $\leq 5\times 10^{-9}$ M, $\leq 2\times 10^{-9}$ M, $\leq 10^{-9}$ M, $10^{-10}$ M). $K_D$ as used herein refers to the ratio of the dissociation rate to the association rate ($k_{off}/k_{on}$), may be determined using surface surface plasmon resonance methods for example using instrument such as BIACORE™.

The ability to "block binding" or "compete for the same epitope" as used herein refers to the ability of an antibody or antigen-binding fragment to inhibit the binding interaction between two molecules (e.g. human PCSK9 and an anti-PCSK9 antibody) to any detectable degree. In certain embodiments, an antibody or antigen-binding fragment that blocks binding between two molecules inhibits the binding interaction between the two molecules by at least 50%. In certain embodiments, this inhibition may be greater than 60%, greater than 70%, greater than 80%, or greater than 90%.

The term "epitope" as used herein refers to the specific group of atoms or amino acids on an antigen to which an antibody binds. Two antibodies may bind the same epitope within an antigen if they exhibit competitive binding for the antigen. For example, if an antibody or antigen-binding fragment as disclosed herein blocks binding of the exemplary antibodies such as 11.4, 18.156.8, 15.14.2, 17.72.3, 18.136.7, 19.3.8, 40409 to human PCSK9, then the antibody or antigen-binding fragment may be considered to bind the same epitope as those exemplary antibodies.

The various symbols used in the antibody names as provided herein are of different representation: "hIgG4" refers to an antibody with human constant region of IgG4 isotype; "uAb" refers to a human antibody and uAb 1, uAb2 and the like refer to different versions of the human antibody; "K" or "L" refers to an antibody using the kappa or lambda light chain.

"11.4" as used herein refers to a fully human monoclonal antibody having a heavy chain variable region of SEQ ID NO: 73, and a light chain variable region of SEQ ID NO: 75. Antibody "11.4.1" is a subclone of 11.4.

"18.156.8" as used herein refers to a fully human monoclonal antibody having a heavy chain variable region of SEQ ID NO: 77, and a light chain variable region of SEQ ID NO: 79. "18.156.8 (hIgG4)" as used herein refers to the antibody of 18.156.8 with a human constant region of IgG4 isotype.

"15.14.2" as used herein refers to a fully human monoclonal antibody having a heavy chain variable region of SEQ ID NO: 81, and a light chain variable region of SEQ ID NO: 83. "15.14.2-uAb-IgG4L" as used herein refers to the fully human monoclonal antibody of 15.14.2 with a human constant region of IgG4 isotype.

"17.72.3" as used herein refers to a fully human monoclonal antibody having a heavy chain variable region of SEQ ID NO: 85, and a light chain variable region of SEQ ID NO: 87. "17.72.3-uAb1-IgG4K" and "17.72.3-uAb2-IgG4K" as used herein refer to different versions of the fully human monoclonal of 17.72.3 with a human constant region of IgG4 isotype.

"18.136.7" as used herein refers to a fully human monoclonal antibody having a heavy chain variable region of SEQ ID NO: 89, and a light chain variable region of SEQ ID NO: 91. "18.136.7-IgG4K" as used herein refers to the fully human monoclonal of 18.136.7 with a human constant region of IgG4 isotype.

"19.3.8" as used herein refers to a fully human monoclonal antibody having a heavy chain variable region of SEQ ID NO: 93, and a light chain variable region of SEQ ID NO: 95. "19.3.8-uAb1-IgG4L" as used herein refers to the fully human monoclonal of 19.3.8 with a human constant region of IgG4 isotype.

"40409" as used herein refers to an engineered antibody based on 11.4 that comprises a heavy chain variable region of SEQ ID NO: 97, and a light chain variable region of SEQ ID NO: 99. 40409 has improved affinity as compared with its parent antibody 11.4. "40409 (hIgG4)" and "40409 (hIgG2)" as used herein refers to the fully human monoclonal of 40409 with a human constant region of IgG4 isotype and IgG2 isotype, respectively.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN™, BLASTP™ (available on the web site of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. In certain embodiments, the antibodies and antigen-binding fragments have a purity of at least 90%, 93%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

The phrase "host cell" as used herein refers to a cell into which an exogenous polynucleotide and/or a vector has been introduced.

A "disease or condition mediated by PCSK9" as used herein refers to a disease or condition caused by or characterized by a change in PCSK9, e.g. a change in expression level, in activity, and/or the presence of a variant or mutation of PCSK9. Examples of a disease or condition mediated by PCSK9 includes, but not limited to, a lipid disorder, hyperlipoproteinemia, hyperlipidemia; dyslipidemia; hypercholesterolemia, a heart attack, a stroke, coronary heart disease, atherosclerosis, peripheral vascular disease, claudication, type II diabetes, high blood pressure, a cardiovascular disease or condition, an inflammatory or autoimmune disease or condition. Methods of identification/diagnosis of above diseases or conditions are known in the art. With regard to the use of the antibodies or antigen-binding fragments disclosed herein to treat CVD (such as acute myocardial infarction (AMI), acute coronary syndrome (ACS), stroke, and CV death), a "therapeutically effective amount" as used herein refers to the dosage or concentration of the antibody or antigen-binding fragment capable of lowering lipid (such as cholesterol) in the plasma or serum, ameliorating any symptom or marker associated with CVD condition, preventing or delaying the development of a CVD condition, or some combination thereof.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-PCSK9 Antibody

In certain embodiments, the present disclosure provides exemplary fully human monoclonal antibodies 11.4, 18.156.8, 15.14.2, 17.72.3, 18.136.7, 19.3.8, 40409, whose CDR sequences are shown in the below Table 1, and heavy or light chain variable region sequences are also shown below.

TABLE 1

|  | CDR1 | CDR2 | CDR3 |
|---|---|---|---|
| 11.4-VH | SEQ ID NO: 1<br>SNSAAWN<br>SEQ ID NO: 2<br>AGC AAC AGT GCT<br>GCT TGG AAC | SEQ ID NO: 3<br>RTYSRSKWYHDYAVSVKG<br>SEQ ID NO: 4<br>AGG ACA TAC TCC<br>AGG TCC AAG TGG<br>TAT CAT GAT TAT<br>GCA GTA TCT GTG<br>AAA GGT | SEQ ID NO: 5<br>DWETSIWNDDGPNYYNYGMDV<br>SEQ ID NO: 6<br>GAT TGG GAG ACC<br>TCT ATC TGG AAC<br>GAC GAC GGT CCC<br>AAC TAC TAC AAC<br>TAC GGT ATG GAC<br>GTC |
| 11.4-VL | SEQ ID NO: 7<br>RASQGIRNDLG<br>SEQ ID NO: 8<br>CGG GCA AGT CAG<br>GGC ATT AGA AAT<br>GAT TTA GGC | SEQ ID NO: 9<br>GASSLQS<br>SEQ ID NO: 10<br>GGT GCA TCC AGT<br>TTG CAA AGT | SEQ ID NO: 11<br>LQHNNYPWT<br>SEQ ID NO: 12<br>CTA CAG CAT AAT<br>AAT TAC CCG TGG<br>ACG |
| 18.156.8-VH | SEQ ID NO: 13<br>SYGMH<br>SEQ ID NO: 14<br>AGC TAT GGC ATG<br>CAC | SEQ ID NO: 15<br>VIWYDGTNKYYADSVKG<br>SEQ ID NO: 16<br>GTT ATA TGG TAT<br>GAT GGA ACT AAT<br>AAA TAC TAT GCA<br>GAC TCC GTG AAG<br>GGC | SEQ ID NO: 17<br>EKGLD<br>SEQ ID NO: 18<br>GAG AAG GGG CTG<br>GAC |
| 18.156.8-VL | SEQ ID NO: 19<br>KSSQSVLYSSTNKNYLV<br>SEQ ID NO: 20<br>AAG TCC AGC CAG<br>AGT GTT TTA TAC<br>AGC TCC ACC AAT<br>AAG AAC TAC TTA<br>GTT | SEQ ID NO: 21<br>WASTRES<br>SEQ ID NO: 22<br>TGG GCA TCT ACC<br>CGG GAA TCC | SEQ ID NO: 23<br>QQYYSTPWT<br>SEQ ID NO: 24<br>CAG CAA TAT TAT<br>AGT ACT CCG TGG<br>ACG |
| 15.14.2-VH | SEQ ID NO: 25<br>RFAMS<br>SEQ ID NO: 26<br>AGA TTT GCC ATG<br>AGC | SEQ ID NO: 27<br>SISDNAGRTYFADSVKG<br>SEQ ID NO: 28<br>AGT ATT AGT GAC<br>AAT GCT GGT AGG<br>ACA TAC TTC GCA<br>GAC TCC GTG AAG<br>GGC | SEQ ID NO: 29<br>LSNWGPYGMDV<br>SEQ ID NO: 30<br>CTC TCA AAC TGG<br>GGT CCT TAC GGT<br>ATG GAC GTC |
| 15.14.2-VL | SEQ ID NO: 31<br>TGTSSDVGYYNYVS<br>SEQ ID NO: 32<br>ACT GGA ACC AGC<br>AGT GAC GTT GGT<br>TAT TAT AAC TAT<br>GTC TCC | SEQ ID NO: 33<br>EVNKRPS<br>SEQ ID NO: 34<br>GAG GTC AAT AAG<br>CGG CCC TCA | SEQ ID NO: 35<br>SSYAGSKNFVV<br>SEQ ID NO: 36<br>AGC TCA TAT GCA<br>GGC AGC AAA AAT<br>TTT GTG GTA |
| 17.72.3-VH | SEQ ID NO: 37<br>SYNWWS<br>SEQ ID NO: 38<br>AGT TAT AAC TGG<br>TGG AGT | SEQ ID NO: 39<br>EIHHSGTTNYNPSLKS<br>SEQ ID NO: 40<br>GAA ATC CAT CAT<br>AGT GGG ACC ACC<br>AAC TAC AAC CCG<br>TCC CTC AAG AGT | SEQ ID NO: 41<br>DYSGSYFDY<br>SEQ ID NO: 42<br>GAT TAT AGT GGG<br>AGC TAC TTT GAC<br>TAC |
|  | SEQ ID NO: 43 | SEQ ID NO: 45 | SEQ ID NO: 47 |

TABLE 1-continued

| | CDR1 | CDR2 | CDR3 |
|---|---|---|---|
| 17.72.3-VL | RTSQSLSSYVA<br>SEQ ID NO: 44<br>AGG ACC AGT CAG<br>AGT CTA AGC AGC<br>TAC GTA GCC | DASKRAT<br>SEQ ID NO: 46<br>GAT GCA TCC AAA<br>AGG GCC ACT | HQRGNWMSS<br>SEQ ID NO: 48<br>CAC CAG CGT GGC<br>AAC TGG ATG TCT<br>AGT |
| 18.136.7-VH | SEQ ID NO: 13<br>SYGMH<br>SEQ ID NO: 14<br>AGC TAT GGC ATG<br>CAC | SEQ ID NO: 49<br>IIWYDGSNKYYADSVKG<br>SEQ ID NO: 50<br>ATT ATA TGG TAT<br>GAT GGA AGT AAC<br>GAC TCC GTG AAG<br>GGC | SEQ ID NO: 17<br>EKGLD<br>SEQ ID NO: 18<br>GAG AAG GGG CTG<br>GAC |
| 18.136.7-VL | SEQ ID NO: 51<br>KSSQSVLYSSNNKNYLV<br>SEQ ID NO: 52<br>AAG TCC AGC CAG<br>AGT GTT TTA TAC<br>AGC TCC AAC AAT<br>AAG AAC TAC TTA<br>GTT | SEQ ID NO: 53<br>WTSTRES<br>SEQ ID NO: 54<br>TGG ACA TCT ACC<br>CGG GAA TCC | SEQ ID NO: 23<br>QQYYSTPWT<br>SEQ ID NO: 24<br>CAG CAA TAT TAT<br>AGT ACT CCG TGG<br>ACG |
| 19.3.8-VH | SEQ ID NO: 55<br>GYYIN<br>SEQ ID NO: 56<br>GGC TAC TAT ATA<br>AAC | SEQ ID NO: 57<br>RINPNSGGTNYAQKFQG<br>SEQ ID NO: 58<br>CGG ATC AAC CCT<br>AAC AGT GGT GGC<br>ACA AAC TAT GCA<br>CAG AAG TTT CAG<br>GGC | SEQ ID NO: 59<br>WEGTVTTWDFYYYYGMDV<br>SEQ ID NO: 60<br>TGG GAG GGA ACG<br>GTG ACT ACG TGG<br>GAT TTC TAC TAT<br>TAC TAC GGT ATG<br>GAC GTC |
| 19.3.8-VL | SEQ ID NO: 61<br>TGTSSDVDTYNYVS<br>SEQ ID NO: 62<br>ACT GGA ACC AGC<br>AGT GAC GTT GAT<br>ACT TAT AAC TAT<br>GTC TCC | SEQ ID NO: 63<br>DVSNRPS<br>SEQ ID NO: 64<br>GAT GTC AGT AAT<br>CGG CCC TCA | SEQ ID NO: 65<br>SSYTSSSTLVV<br>SEQ ID NO: 66<br>AGC TCA TAT ACA<br>AGC AGC AGC ACT<br>CTC GTG GTA |
| 40409-VH | SEQ ID NO: 1<br>SNSAAWN<br>SEQ ID NO: 2<br>AGC AAC AGT GCT<br>GCT TGG AAC | SEQ ID NO: 67<br>RIYSRSKWYHDYAV<br>SVKG<br>SEQ ID NO: 68<br>AGG ATA TAC TCC<br>AGG TCC AAG TGG<br>TAT CAT GAT TAT<br>GCA GTA TCT GTG<br>AAA GGT | SEQ ID NO: 69<br>DWETIIWGDDGPNY<br>YNYGLDV<br>SEQ ID NO: 70<br>GAT TGG GAG ACC<br>ATT ATC TGG GGC<br>GAC GAC GGT CCC<br>AAC TAC TAC AAC<br>TAC GGT TTG GAC<br>GTC |
| 40409-VL | SEQ ID NO: 7<br>RASQGIRNDLG<br>SEQ ID NO: 8<br>CGG GCA AGT CAG<br>GGC ATT AGA AAT<br>GAT TTA GGC | SEQ ID NO: 9<br>GASSLQS<br>SEQ ID NO: 10<br>GGT GCA TCC AGT<br>TTG CAA AGT | SEQ ID NO: 71<br>LQHNNYLWT<br>SEQ ID NO: 72<br>CTA CAGCAT AAT<br>AAT TAC CTG TGG<br>ACG |

Amino acid sequence (SEQ ID NO: 73):

QLNLQQSGPGLVNPSQTLSTCAISGGSVSSNSAAWNWIRQSPSRGLEWLGRIYSRS

KWYHDYAVSVKGRITINPDTSKNQFFLQLNSVTPEDTAVYYCARDWETIIWNDDGP

NYYNYGMDVWGQGTTVTSS

Nucleic acid sequence (SEQ ID NO: 74)

CAGCTAAACCTGCAGCAGTCAGGTCCAGGACTGGTGAACCCCTCGCAGACCCTCT

CACTCACCTGTGCCATCTCCGGGGGCAGTGTCTCTAGCAACAGTGCTGCTTGGAA

CTGGATCAGGCAGTCCCCGTCGAGAGGCCTTGAGTGGCTGGGAAGGACATACTC

CAGGTCCAAGTGGTATCATGATTATGCAGTATCTGTGAAAGGTCGGATAACCATC

TABLE 1-continued

| | CDR1 | CDR2 | CDR3 |
|---|---|---|---|

11.4-VL:
Amino acid sequence (SEQ ID NO: 75):

DIQMTQSPSSLSASVGDRVTITCRASQGIRNDLGWYQQKPGKAPKRLIYGASSLQSG

VPSRFSGSGSGTEFTLTISSLQPEDFATYYCQHNNYPWTFGQGTKVEIK

Nucleic acid sequence (SEQ ID NO: 76)

GACATCCAGATGACCCAGTCTCCATCCTCCCTGTCTGCATCTGTAGGAGACAGAG

TCACCATCACTTGCCGGGCAAGTCAGGGCATTAGAAATGATTTAGGCTGGTATCA

GCAGAAACCAGGGAAAGCCCCTAAGCGCCTGATCTATGGTGCATCCAGTTTGCA

AAGTGGGGTCCCATCAAGGTTCAGCGGCAGTGGATCTGGGACAGAATTCACTCT

CACAATCAGCAGCCTGCAGCCTGAAGATTTTGCAACTTATTACTGTCTACAGCAT

AATAATTACCCGTGGACGTTCGGCCAAGGGACCAAGGTGGAAATCAAA 18.156.8-VH
Amino acid sequence (SEQ ID NO: 77):

AGACTCTCCTGTGCAGCGTCTGGATTCACCTTCAGTAGCTATGGCATGCACTGGG

TCCGCCAGGCTCCAGGCAAGGGGCTGGAGTGGATGGCAGTTATATGGTATGATG

GAACTAATAAATACTATGCAGACTCCGTGAAGGGCCGATTCACCATCTCCAGAG

VTVSS
Nucleic acid sequence (SEQ ID NO: 78)

CAGGTGCAGCTGGTGGAGTCTGGGGGAGGCGTGGTCCAGCCTGGGAGGTCCCTG

AGACTCTCCTGTGCAGCGTCTGGATTCACCTTCAGTAGCTATGGCATGCACTGGG

TCCGCCAGGCTCCAGGCAAGGGGCTGGAGTGGATGGCAGTTATATGGTATGATG

GAACTAATAAATACTATGCAGACTCCGTGAAGGGCCGATTCACCATCTCCAGAG

CGGCTGTGTATTACTGTGCGAGAGAGAAGGGGCTGGACTGGGGCCAGGGAACCC 18.156.8-VL
Amino acid sequence (SEQ ID NO: 79):

DIVMTQSPDSLAVSLGERATINCKSSQSVLYSSTNKNYLVWYQQKPGQPPKLLIYWA

STRESGVPDRFSGSGSGTDFTLTISSLQAEDVAVYYCQQYYSTPWTFGQGTKVEIK

Nucleic acid sequence (SEQ ID NO: 80)

GACATCGTGATGACCCAGTCTCCAGACTCCCTGGCTGTGTCTCTGGGCGAGAGGG

CCACCATCAACTGCAAGTCCAGCCAGAGTGTTTTATACAGCTCCACCAATAAGAA

CTACTTAGTTTGGTACCAGCAGAAACCAGGACAGCCTCCTAAGCTGCTCATTTAC

TGGGCATCTACCCGGGAATCCGGGGTCCCTGACCGATTCAGTGGCAGCGGGTCTG

GGACAGATTTCACTCTCACCATCAGCAGCCTGCAGGCTGAAGATGTGGCAGTTTA

TTACTGTCAGCAATATTATAGTACTCCGTGGACGTTCGGCCAAGGGACCAAGGTG

GAAATCAAA

TABLE 1-continued

| CDR1 | CDR2 | CDR3 |
|------|------|------|

15.14.2-VH
Amino acid sequence (SEQ ID NO: 81):

EVQMLESGGGLVQPGGSLRLSCAVSGFTFSRFAMSWVRQAPGKGLDWVSSISDNAG

RTYFADSVKGRFTISRDNSKNTLYLQMNSLRADDTAVYYCAKLSNWGPYGMDVWG

QGTTVTVSS

QGTTVTVSS
Nucleic acid sequence (SEQ ID NO: 82)

GAAGTGCAGATGTTGGAGTCTGGGGGAGGCTTGGTACAGCCTGGGGGGTCCCTG

AGACTCTCCTGTGCAGTCTCTGGATTCACCTTTAGCAGATTTGCCATGAGCTGGG

TCCGCCAGGCTCCAGGGAAGGGGCTGGACTGGGTCTCAAGTATTAGTGACAATG

CTGGTAGGACATACTTCGCAGACTCCGTGAAGGGCCGGTTCACCATCTCCAGAGA

CAATTCCAAGAACACGCTGTATCTGCAAATGAACAGCCTGAGAGCCGACGACAC

GGCCGTATATTACTGTGCGAAACTCTCAAACTGGGGTCCTTACGGTATGGACGTC

TGGGGCCAAGGGACCACGGTCACCGTCTCCTCG 15.14.2-VL
Amino acid sequence (SEQ ID NO: 83):

QSALTQPPSASGSPGQSVTISCTGTSSDVGYYNYVSWYQQHPGEAPKLMIYEVNKRP

SGVPDRFSGSKSGSTASLTVSGLQAVDEADYYCSSYAGSKNFVVFGGGTKLTVL

Nucleic acid sequence (SEQ ID NO: 84)

CAGTCTGCCCTGACTCAGCCTCCCTCCGCGTCCGGGTCTCCTGGACAGTCAGTCA

CCATCTCCTGCACTGGAACCAGCAGTGACGTTGGTTATTATAACTATGTCTCCTG

GTACCAACAGCACCCAGGCGAAGCCCCCAAACTCATGATTTATGAGGTCAATAA

GCGGCCCTCAGGGGTTCCTGATCGCTTCTCTGGCTCCAAGTCTGGCAGCACGGCC

TCCCTGACCGTCTCTGGGCTCCAGGCTGTGGATGAGGCTGATTATTACTGCAGCT

CATATGCAGGCAGCAAAAATTTTGTTGGTATTCGGCGGAGGGACCAAGCTGACCG 17.72.3-VH
Amino acid sequence (SEQ ID NO: 85):

SQVQLQESGPGLVKPSGTLSLTCAVSGGSIRSYNWWSWVRQPPGEGLEWIGEIHHSG

TTNYNPSLKSRVTISVDKSKNQFSLKLSSVTAADTAVYYCARDYSGSYFDYWGQGT

LVTVSS

LVTVSS
Nucleic acid sequence (SEQ ID NO: 86)

TCTCAGGTGCAGCTGCAGGAGTCGGGCCCAGGACTGGTGAAGCCTTCGGGGACC

CTGTCCCTCACCTGCGCTGTCTCTGGTGGCTCCATCAGGAGTTATAACTGGTGGA

GTTGGGTCCGCCAGCCCCCAGGGGAGGGGCTGGAGTGGATTGGGGAAATCCATC

ATAGTGGGACCACCAACTACAACCCGTCCCTCAAGAGTCGAGTCACCATATCGGT

AGACAAGTCCAAGAACCAGTTCTCCCTGAAGCTGAGCTCTGTGACCGCCGCGGA

| | CDR1 | CDR2 | CDR3 |
|---|---|---|---|

CACGGCCGTGTATTACTGTGCGAGA<u>GATTATGTGGGAGCTACTTTGACTAC</u>TGG

GGCCAGGGAACCCTGGTCACCGTCTCCTCA 17.72.3-VL
Amino acid sequence (SEQ ID NO: 87):

EVVLTQSPATLSLSPGERATLSC<u>RTSQSLSSYVA</u>WSQQKPGQAPRLLIY<u>DASKRAT</u>GV

PARFSGSGSGTDFTLTISNLEPEDAVYYC<u>HQRGNWMSS</u>FGQGTKLEIK

Nucleic acid sequence (SEQ ID NO: 88)

GAGGTTGTGTTGACACAGTCTCCCGCCACCCTGTCTTTGTCTCCAGGGGAAAGAG

CCACCCTCTCCTGC<u>AGGACCAGTCAGAGTCTAAGCAGCTACGTAGCC</u>TGGTCCCA

GCAGAAGCCTGGCCAGGCTCCCAGGCTCCTCATCTAT<u>GATGCATCCAAAAGGGC</u>

<u>CACT</u>GGCGTCCCAGCCAGGTTCAGTGGCAGTGGGTCTGGGACAGACTTCACTCTC

ACCATCAGCAACCTAGAGCCTGAAGATTTTGCAGTTTATTACTGT<u>CACCAGCGTG</u>

<u>GCAACTGGATGTCTAGT</u>TTTGGCCAGGGGACCAAGCTGGAGATCAAA 18.136.7-VH
Amino acid sequence (SEQ ID NO: 89):

QVQLVESGGGVVQPGRSLRLSCAASGFTFS<u>SYGMH</u>WVRQAPGKGLEWVA<u>IIWYDG</u>

<u>SNKYYADSVK</u>GRFTISRDNSKNTLYLQMNSLRAEDTAVYYCVR<u>EKGLDW</u>GQGTLV

TVSS

Nucleic acid sequence (SEQ ID NO: 90)

CAGGTGCAGCTGGTGGAGTCTGGGGGAGGCGTGGTCCAGCCTGGGAGGTCCCTG

AGACTCTCCTGTGCAGCGTCTGGGTTCACCTTCAGT<u>AGCTATGGCATGCAC</u>TGGG

TCCGCCAGGCTCCAGGCAAGGGGCTGGAGTGGGTGGCA<u>ATTATATGGTATGATG</u>

<u>GAAGTAACAAATACTATGCAGACTCCGTGAAGGGC</u>CGATTCACCATCTCCAGAG

ACAATTCCAAGAACACGCTGTATCTGCAAATGAACAGCCTGAGAGCCGAGGACA

CGGCTGTGTATTACTGTGTGAGAGA<u>GAAGGGGCTGGAC</u>TGGGGCCAGGGAACCC

TGGTCACCGTCTCCTCA 18.136.7-VL
Amino acid sequence (SEQ ID NO: 91):

DIVMTQSPDSLAVSLGERATINC<u>KSSQSVLYSSNNKNYLV</u>WYQQKPGQPPKLLIY<u>WT</u>

<u>STRES</u>GVPDRFSGSGSGTDFTLTISSLQAEDVAVYYC<u>QQYYSTPWT</u>FGQGTKVEIK

Nucleic acid sequence (SEQ ID NO: 92)

GACATCGTGATGACCCAGTCTCCAGACTCCCTGGCTGTGTCTCTGGGCGAGAGGG

CCACCATCAACTGC<u>AAGTCCAGCCAGAGTGTTTTATACAGCTCCAACAATAAGAA</u>

<u>CTACTTAGTT</u>TGGTACCAGCAGAAACCAGGACAGCCTCCTAAGCTGCTCATTTAC

<u>TGGACATCTACCCGGGAATCC</u>GGGGTCCCTGACCGATTCAGTGGCAGCGGGTCTG

GGACAGATTTCACTCTCACCATCAGCAGCCTGCAGGCTGAAGATGTGGCAGTTTA

TABLE 1-continued

| | CDR1 | CDR2 | CDR3 |
|---|---|---|---|

TTACTGTCAGCAATATTATAGTACTCCGTGGACGTTCGGCCAAGGGACCAAGGTG

GAAATCAAA 19.3.8-VH
Amino acid sequence (SEQ ID NO: 93):

QVQLVQSGAEVKKPGASVKVSCKASGYTFTGYYINWVRQAPGQGLEWMGRINPNS

GGTNYAQKFQGRVTMTRDTSINTAYMELSRLRSDDTAVYFCASWEGTVTTWDFYY

YYGMDVWGQGTTVTVSS

Nucleic acid sequence (SEQ ID NO: 94)

CAGGTGCAGTTGGTGCAGTCTGGGGCTGAGGTGAAGAAGCCTGGGGCCTCAGTG

AAGGTCTCCTGCAAGGCTTCCGGATACACCTTCACCGGCTACTATATAAACTGGG

TGCGACAGGCCCCTGGACAAGGGCTTGAGTGGATGGGACGGATCAACCCTAACA

GTGGTGGCACAAACTATGCACAGAAGTTTCAGGGCAGGGTCACCATGACCAGGG

ACACGTCCATCAACACAGCCTACATGGAGCTGAGCAGGCTGAGATCTGACGACA

CGGCCGTGTATTTCTGTGCGAGTTGGGAGGGAACGGTGACTACGTGGGATTTCTA

CTATTACTACGGTATGGACGTCTGGGGCCAAGGGACCACGGTCACCGTCTCCTCA 19.3.8-VL
Amino acid sequence (SEQ ID NO: 95):

QSALTQPASVSGSPGQSITISCTGTSSDVDTYNYVSWYQHHPGKAPKLIIFDVSNRPSG

VSNRFSGSKSGNTASLTISGLQAEDEADYYCSSYTSSSTLVVFGGGTKLTVL

Nucleic acid sequence (SEQ ID NO: 96)

CAGTCTGCCCTGACTCAGCCTGCCTCCGTGTCTGGATCTCCTGGACAGTCGATCA

CCATCTCCTGCACTGGAACCAGCAGTGACGTTGATACTTATAACTATGTCTCCTG

GTACCAACATCACCCAGGCAAAGCCCCCAAGCTCATAATTTTTGATGTCAGTAAT

CGGCCCTCAGGGGTTTCTAATCGCTTCTCTGGCTCCAAATCTGGCAACACGGCCT

CCCTGACCATCTCTGGGCTCCAGGCTGAGGACGAGGCTGATTATTACTGCAGCTC

ATATACAAGCAGCAGCACTCTCGTGGTATTCGGCGGAGGGACCAAGCTGACGT

CCTA

40409-VH
Amino acid sequence (SEQ ID NO: 97):

QLNLQQSGPGLVNPSQTLSLTCAISGGSVSSNSAAWNWIRQSPSRGLEWLGRIYSRSK

WYHDYAVSVKGRITINPDTSKNQFFLQLNSVTPEDTAVYYCARDWETIIWGDDGPN

YNYGLDVWGQGTTVTVSS

Nucleic acid sequence (SEQ ID NO: 98)

CAGCTAAACCTGCAGCAGTCAGGTCCAGGACTGGTGAACCCCTCGCAGACCCTCT

CACTCACCTGTGCCATCTCCGGGGGCAGTGTCTCTAGCAACAGTGCTGCTTGGAA

TABLE 1-continued

| CDR1 | CDR2 | CDR3 |
|------|------|------|

CTGGATCAGGCAGTCCCCGTCGAGAGGCCTTGAGTGGCTGGGAAGGATATACTC

CAGGTCCAAGTGGTATCATGATTATGCAGTATCTGTGAAAGGTCGGATAACCATC

AACCCAGACACATCCAAGAACCAGTTCTTCCTGCAGCTGAACTCTGTGACTCCCG

AAGCACACGGCTGTGTATTACTGTGCAAGAGATTGGGAGACCATTATCTGGGGCG

ACGACGGTCCCAACTACTACAACTACGGTTTGGACGTCTGGGGCCAAGGGACCA

CGGTCACCGTCTCCTCA

40409-VL
Amino acid sequence (SEQ ID NO: 99):

DIQMTQSPSSLSASVGDRVTITCRASQGIRNDLGWYQQKPGKAPLRLIYGASSLQSG

VPSRFSGSGSGTEFTLTISSLQPEDFATYYCLQHNNYLWTFGQGTKVEIK

Nucleic acid sequence (SEQ ID NO: 100)

GACATCCAGATGACCCAGTCTCCATCCTCCCTGTCTGCATCTGTAGGAGACAGAG

TCACCATCACTTGCCGGGCAAGTCAGGGCATTAGAAATGATTTAGGCTGGTATCA

GCAGAAACCAGGGAAAGCCCCTAAGCGCCTGATCTATGGTGCATCCAGTTTGCA

AAGTGGGGTCCCATCAAGGTTCAGCGGCAGTGGATCTGGGACAGAATTCACTCT

CACAATCAGCAGCCTGCAGCCTGAAGATTTTGCAACTTATTACTGTCTACAGCAT

AATAATTACCTGTGGACGTTCGGCCAAGGGACCAAGGTGGAAATGAAA

In certain embodiments, one or more CDR sequences provided herein can be modified or changed such that the resulting antibody is improved over the parent antibody in one or more properties (such as improved antigen-binding, improved glycosylation pattern, reduced risk of glycosylation on a CDR residue, reduced deamination on a CDR residue, increased pharmacokinetic half-life, pH sensitivity, and compatibility to conjugation), and is otherwise comparable to the parent antibody (i.e. antibody having otherwise the same set of CDR sequences except for the above-mentioned modification or change), or at least substantially retains the antigen-binding property of the parent antibody.

A skilled artisan will understand that the CDR sequences provided in Table 1 can be modified to contain one or more substitutions of amino acids, so as to provide for an improved biological activity such as improved binding affinity to human PCSK9. For example, a library of antibody variants (such as Fab or scFv variants) can be generated and expressed with phage display technology, and then screened for the binding affinity to human PCSK9. For another example, computer software can be used to virtually simulate the binding of the antibodies to human PCSK9, and identify the amino acid residues on the antibodies which form the binding interface. Such residues may be either avoided in the substitution so as to prevent reduction in binding affinity, or targeted for substitution to provide for a stronger binding. In certain embodiments, at least one (or all) of the substitution(s) in the CDR sequences is conservative substitution.

In certain embodiments, the antibodies and the antigen-binding fragments thereof comprise one or more CDR sequences having at least 80% (e.g. at least 85%, 88%, 90%, 91%, 92%, 93%, 94%, 95%, 96%, 97%, 98%, 99%) sequence identity to that (or those) listed in Table 1, and in the meantime retain the binding affinity to human PCSK9 at a level similar to or even higher than its parental antibody having substantially the same sequence except that the corresponding CDR sequence is in 100% sequence identity to that (or those) listed in Table 1.

In certain embodiments, the anti-PCSK9 antibodies and the antigen-binding fragments thereof are fully human. Theses fully human antibodies retain the binding affinity to human PCSK9, preferably at a level similar to one of the exemplary antibodies: 11.4, 18.156.8, 15.14.2, 17.72.3, 18.136.7, 19.3.8, 40409.

Also contemplated herein are antibodies and the antigen-binding fragments that compete for the same epitope with the anti-PCSK9 antibodies and the antigen-binding fragments thereof provided herein. In certain embodiments, the antibodies block binding of 11.4, 18.156.8, 15.14.2, 17.72.3, 18.136.7, 19.3.8, 40409 to human or monkey PCSK9, for example, at an $IC_{50}$ value (i.e. 50% inhibition concentration) of below $10^{-6}$ M, below $10^{-7}$ M, below $10^{-7.5}$ M, below $10^{-8}$ M, below $10^{-8.5}$ M, below $10^{-9}$ M, or below $10^{-10}$ M, below $10^{-11}$ M or below $10^{-12}$M. The $IC_{50}$ values are determined based on a competition assay such as ELISA assays and radioligand competition binding assays.

In some embodiments, the anti-PCSK9 antibodies and the antigen-binding fragments thereof provided herein are capable of specifically binding to human PCSK9 and/or monkey with a binding affinity (Kd) of no more than $10^{-8}$ M, no more than $10^{-9}$ M or no more than $10^{-10}$ M (e.g., $\leq 2.5\times10^{-8}$ M, $\leq 2\times10^{-8}$ M, $\leq 7.5\times10^{-9}$ M, $\leq 3.5\times10^{-9}$ M, $\leq 7\times10^{-10}$ M, $\leq 6\times10^{-10}$ M, $\leq 5\times10^{-10}$ M, $\leq 2.5\times10^{-10}$ M, ≤2×10$^{-10}$ M, ≤1.5×10$^{-10}$ M, ≤7.5×10$^{-11}$ M, ≤6.5×10$^{-11}$ M, or ≤5.5×10$^{-11}$ M) as measured by surface plasmon resonance binding assay or ELISA. The binding affinity can be represented by K$_D$ value, which is calculated as the ratio of dissociation rate to association rate (k$_{off}$/k$_{on}$) when the binding between the antigen and the antigen-binding molecule reaches equilibrium. The antigen-binding affinity (e.g. K$_D$) can be appropriately determined using suitable methods known in the art, including, for example, surface plasmon resonance binding assay using instruments such as BIA-CORE™ (see, for example, Murphy, M. et al, Current protocols in protein science, Chapter 19, unit 19.14, 2006).

In certain embodiments, the antibodies and the fragments thereof provided herein binds to human PCSK9 with an EC$_{50}$ (i.e. 50% binding concentration) of 0.01 nM-0.2 nM (e.g. 0.02 nM-0.2 nM, 0.02 nM-0.15 nM, 0.02 nM-0.05 nM, 0.01 nM-0.05 nM, or 0.02 nM-0.3 nM). Binding of the antibodies to human PCSK9 can be measured by methods known in the art, for example, sandwich assay such as ELISA, Western Blot, other binding assay. In an illustrative example, the test antibody (i.e. first antibody) is allowed to bind to immobilized human PCSK9, after washing away the unbound antibody, a labeled secondary antibody is introduced which can bind to and thus allow detection of the bound first antibody. The detection can be conducted with a microplate reader when immobilized PCSK9 is used.

In certain embodiments, the antibodies and the fragments thereof provided herein inhibit the binding of human PCSK9 to human LDL receptor at an IC$_{50}$ of 0.5 nM-3 nM (e.g. 0.5 nM-2.5 nM, 1 nM-2.5 nM, 1 nM-2 nM, or 1 nM-1.5 nM), as measured in a competition assay.

In certain embodiments, the antibodies and antigen-binding fragments thereof bind to monkey PCSK9 with a binding affinity similar to that of human PCSK9. For example, binding of the exemplary antibodies 11.4, 18.156.8, 15.14.2, 17.72.3, 18.136.7, 19.3.8, 40409 to monkey PCSK9 is at a similar affinity or EC$_{50}$ value to that of human PCSK9.

In some embodiments, the anti-PCSK9 antibodies and the antigen-binding fragments thereof further comprise an immunoglobulin constant region. In some embodiments, an immunoglobulin constant region comprises a heavy chain and/or a light chain constant region. The heavy chain constant region comprises CH1, CH1-CH2, or CH1-CH3 regions. In some embodiments, the constant region may further comprise one or more modifications to confer desirable properties. For example, the constant region may be modified to reduce or deplete one or more effector functions, to improve FcRn receptor binding, or to introduce one or more cysteine residues. In some embodiments, the anti-PCSK9 antibodies and the antigen-binding fragments thereof have a constant region of IgG4 isotype, which has reduced or depleted effector function. Various assays are known to evaluate ADCC or CDC activities, for example, Fc receptor binding assay, C1q binding assay, and cell lysis assay, and can be readily selected by people in the art.

In certain embodiments, the antibodies and antigen-binding fragments thereof can be used as the base of antibody-drug conjugates, bispecific or multivalent antibodies.

The anti-PCSK9 antibodies or antigen-binding fragments thereof provided herein can be a monoclonal antibody, polyclonal antibody, fully human antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals. A bispecific or bivalent antibody is an artificial antibody having fragments of two different monoclonal antibodies and can bind two different antigens. An antibody or antigen-binding fragment thereof that is "bivalent" comprises two antigen-binding sites. The two antigen binding sites may both bind to the same antigen, or they may each bind to a different antigen, in which case the antibody or antigen-binding fragment is characterized as "bispecific."

In some embodiments, the anti-PCSK9 antibodies or antigen-binding fragments thereof provided herein are fully human antibodies. In certain embodiments, the fully human antibodies are prepared using recombinant methods. For example, transgenic animal such as a mouse can be made to carry transgenes or transchromosomes of human immunoglobulin genes, and therefore capable of producing fully human antibodies after immunization with proper antigen such as human PCSK9. Fully human antibodies can be isolated from such transgenic animal, or alternatively, can be made by hybridoma technology by fusing the spleen cells of the transgenic animal with an immortal cell line to generate hybridoma cells secreting the fully human antibodies. Exemplary transgenic animals include, without limitation, OMNIRAT®, whose endogenous expression of rat immunoglobulin genes are inactivated and at the same time engineered to contain functional recombinant human immunoglobulin loci; OmniMouse, whose endogenous expression of mouse immunoglobulin genes are inactivated and at the same time engineered to contain recombinant human immunoglobulin loci having J-locus deletion and a C-kappa mutation; OmniFlic, which is a transgenic rat whose endogenous expression of rat immunoglobulin genes are inactivated and at the same time engineered to contain recombinant human immunoglobulin loci having a single common, rearranged VkJk light chain and functional heavy chain. Detailed information can be further found at: Osborn M. et al, Journal of Immunology, 2013, 190: 1481-90; Ma B. et al, Journal of Immunological Methods 400-401 (2013) 78-86; Geurts A. et al, Science, 2009, 325:433; U.S. Pat. No. 8,907,157; EP patent 2152880B1; EP patent 2336329B1, all of which are incorporated herein by reference to its entirety. Other suitable transgenic animals can also be used, for example, HuMab mice (see, for details, Lonberg, N. et al. Nature 368(6474): 856 859 (1994)), Xeno-Mouse (Mendez et al. Nat Genet., 1997, 15:146-156), TransChromo Mouse (Ishida et al. Cloning Stem Cells, 2002, 4:91-102) and VelocImmune Mouse (Murphy et al. Proc Natl Acad Sci USA, 2014, 111:5153-5158), Kymouse (Lee et al. Nat Biotechnol, 2014, 32:356-363), and transgenic rabbit (Flisikowska et al. PLoS One, 2011, 6:e21045).

In some embodiments, the anti-PCSK9 antibodies and the antigen-binding fragments thereof is a camelized single domain antibody, a diabody, a scFv, an scFv dimer, a BsFv, a dsFv, a (dsFv)2, a dsFv-dsFv', an Fv fragment, a Fab, a Fab', a F(ab')2, a ds diabody, a nanobody, a domain antibody, or a bivalent domain antibody.

In some embodiments, the anti-PCSK9 antibodies and the antigen-binding fragments thereof further comprise a conjugate. It is contemplated that a variety of conjugates may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). These conjugates may be linked to the antibodies or antigen-binding fragments by covalent binding, affinity binding, intercalation, coordinate binding, complexation, association, blending, or addition, among other methods. In certain embodiments, the antibodies and antigen-binding fragments disclosed herein may be engineered to contain specific sites outside the epitope binding portion that may be utilized for binding to one or more conjugates. For example, such a site may include one or more reactive amino acid residues, such as for example cysteine or histidine residues, to facilitate covalent linkage to a conjugate. In certain embodiments, the antibodies may be linked to a conjugate indirectly, or through another conjugate. For example, the antibody or antigen-binding fragments may be conjugated to biotin, then indirectly conjugated to a second conjugate that is conjugated to avidin. The conjugate can be a detectable label, a pharmacokinetic modifying moiety, a purification moiety, or a cytotoxic moiety. Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P, other lanthanides, luminescent labels), chromophoric moiety, digoxigenin, biotin/avidin, a DNA molecule or gold for detection. In certain embodiments, the conjugate can be a pharmacokinetic modifying moiety such as PEG which helps increase half-life of the antibody. Other suitable polymers include, such as, carboxymethylcellulose, dextran, polyvinyl alcohol, polyvinyl pyrrolidone, copolymers of ethylene glycol/propylene glycol, and the like. In certain embodiments, the conjugate can be a purification moiety such as a magnetic bead. A "cytotoxic moiety" can be any agent that is detrimental to cells or that can damage or kill cells. Examples of cytotoxic moiety include, without limitation, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Polynucleotides and Recombinant Methods

The present disclosure provides isolated polynucleotides that encode the anti-PC SK9 antibodies and the antigen-binding fragments thereof. In certain embodiments, the isolated polynucleotides comprise one or more nucleotide sequences as shown in Table 1, which encodes the CDR sequences provided in Table 1.

In some embodiments, the isolated polynucleotides encodes a heavy chain variable region and comprise a sequence selected from the group consisting of: SEQ ID NO: 26, SEQ ID NO: 30, SEQ ID NO: 34, and a homologous sequence thereof having at least 80% (e.g. at least 85%, 88%, 90%, 91%, 92%, 93%, 94%, 95%, 96%, 97%, 98%, 99%) sequence identity. In some embodiments, the isolated polynucleotides encodes a light chain variable region and comprise a sequence selected from the group consisting of: SEQ ID NO: 28, SEQ ID NO: 32, SEQ ID NO: 36, and a homologous sequence thereof having at least 80% (e.g. at least 85%, 88%, 90%, 91%, 92%, 93%, 94%, 95%, 96%, 97%, 98%, 99%) sequence identity. In certain embodiments, the percentage identity is due to genetic code degeneracy, while the encoded protein sequence remains unchanged.

The isolated polynucleotide that encodes the anti-PCSK9 antibodies and the antigen-binding fragments thereof (e.g. including the sequences in Table 1) can be inserted into a vector for further cloning (amplification of the DNA) or for expression, using recombinant techniques known in the art. In another embodiment, the antibody may be produced by homologous recombination known in the art. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

In some embodiments, the vector system includes mammalian, bacterial, yeast systems, etc., and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS420, pLexA, pACT2.2 etc., and other laboratorial and commercially available vectors. Suitable vectors may include, plasmid, or viral vectors (e.g., replication defective retroviruses, adenoviruses and adeno-associated viruses).

Vectors comprising the polynucleotide sequence encoding the antibody or antigen-binding fragment can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*.

In addition to prokaryotes, eukaryotic microbes such as filamentous fungi or yeast are suitable cloning or expression hosts for anti-PCSK9 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2). In some preferable embodiments, the host cell is 293F cell.

Host cells are transformed with the above-described expression or cloning vectors for anti-PCSK9 antibody production and cultured in conventional nutrient media modified as appropriate for inducing promoters, selecting transformants, or amplifying the genes encoding the desired sequences.

The host cells used to produce the antibodies or antigen-binding fragments provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human.gamma.1, .gamma.2, or .gamma.4 heavy chains (Lindmark et al., J. Immunol. Meth. 62:1-13 (1983)). Protein G is recommended for all mouse isotypes and for human.gamma.3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX.TM. resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SD S-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Kits

The present disclosure provides kits comprising the anti-PCSK9 antibodies or the antigen-binding fragments thereof. In some embodiments, the kits are useful for detecting the presence or level of PCSK9 in a biological sample. The biological sample can comprise serum. In some embodiments, the kit comprises an anti-PCSK9 antibody or the antigen-binding fragment thereof which is conjugated with a detectable label. In certain other embodiments, the kit comprises an unlabeled anti-PCSK9 antibody or antigen-binding fragment, and further comprises a secondary labeled antibody which is capable of binding to the unlabeled anti-PCSK9 antibody. The kit may further comprise an instruction of use, and a package that separates each of the components in the kit.

In some embodiments, the kits are useful for treating, preventing, or delaying diseases or conditions mediated by PCSK9. In certain embodiments, the anti-PCSK9 antibody or the antigen-binding fragment thereof are associated with a substrate or a device useful in a sandwich assay such as ELISA, or in an immunographic assay. Useful substrate or device can be, for example, microtiter plate and test strip.

In certain embodiments, the kit further comprises one or more agents known to be beneficial for reducing cholesterol. Exemplary agents include statin, an HMG-CoA reductase inhibitor other than a statin, niacin (nicotinic acid), a cholesterol absorption inhibitor, a cholesteryl ester transfer protein (CETP), a bile acid sequestrant, a fibrate, a phytosterol; or a modulator of lipid/lipid concentration ratios selected from a small molecule, peptidomimetic, an antisense RNA, a small interfering RNA (siRNA), and a natural or modified lipid. In certain embodiments, a cholesterol absorption inhibitor is ezetimibe or SCH-48461; a CETP is evacetrapib, anacetrapib or dalcetrapib; a bile acid sequestrant is preferably colesevelam, cholestyramine or colestipol; a fibrate is preferably fenofibrate, gemfibrozil, clofibrate, or bezafibrate; or the combination thereof.

Pharmaceutical Composition and Method of Treatment

The present disclosure further provides pharmaceutical compositions comprising the anti-PCSK9 antibodies or the antigen-binding fragments thereof and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispensing agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylceluose, hydroxypropyl methylcellulose, or polyvinylpyrrolidone, emulsifying agents such as Polysorbate 80 (TWEEN™-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-PCSK9 antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Therapeutic methods are also provided, comprising: administering a therapeutically effective amount of the antibody or antigen-binding fragment as provided herein to a subject in need thereof, thereby treating or preventing a condition or a disorder associated with related to PCSK9. In another aspect, methods are provided to treat a condition in a subject that would benefit from upregulation of immune response, comprising administering a therapeutically effective amount of the antibody or antigen-binding fragment as provided herein to a subject in need thereof.

The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of CVD development. Dosages may be proportionally reduced or increased by one of ordinary skill in the art (e.g., physician or veterinarian) as indicated by these and other circumstances or requirements.

In certain embodiments, an antibody or antigen-binding fragment as provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 3 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the antibody or antigen-binding fragment is administered at a dosage of about 50 mg/kg or less, and in certain of these embodiments the dosage is 10 mg/kg or less, 5 mg/kg or less, 3 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

Methods of Use

The present disclosure further provides methods of using the anti-PCSK9 antibodies or the antigen-binding fragments thereof.

In some embodiments, the present disclosure provides methods of treating a condition or a disorder associated with or mediated by PCSK9 in an individual, comprising administering a therapeutically effective amount of the anti-PCSK9 antibody or antigen-binding fragment thereof. In certain embodiments, the individual has been identified as having a disorder or condition likely to respond to a PCSK9 inhibitor. In certain embodiments, the individual is at risk of having or developing a disease or condition mediated by PCSK9 that exhibits one or more symptoms of said disease or condition, such as being overweight, having elevated cholesterol level, having genetic mutation in the genes encoding LDL-R or APOB, or having family history of such a disease or condition. In certain embodiments, the individual is resistant to or intolerable to another cholesterol lowering agents in a therapy, for example, statin, such that the level of cholesterol cannot be effectively lowered to an acceptable level in such therapy. In certain embodiments, the diseases or conditions mediated by PCSK9 include infectious disease such as severe cellulitis, gastroenteritis, sepsis, pneumonia, skin and soft tissue infections, pyelonephritis, viral infection, for example, viral infection of hepatitis B, hepatitis C, herpes virus, Epstein-Barr virus, HIV, cytomegalovirus, herpes simplex virus type I, herpes simplex virus type 2, human papilloma virus, adenovirus, Kaposi West sarcoma associated herpes virus epidemics, thin ring virus (Torquetenovirus), JC virus or BK virus, or include inflammatory diseases, such as Alzheimer's, ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus erythematous (SLE), nephritis, Parkinson's disease and ulcerative colitis.

The presence or level of LDL-C on an interested biological sample can be indicative of whether the individual from whom the biological sample is derived could likely respond to a PCSK9 inhibitor. Various methods can be used to determine the presence or level of LDL-C in a test biological sample from the individual. Milligrams (mg) per deciliter (dL) of blood of cholesterol levels are measured in the USA, while millimoles (mmol) per liter (L) of blood are used in Canada and many European countries.

In certain embodiments, presence or upregulated level of the LDL-C, total cholesterol or non-HDL-C in the test biological sample indicates likelihood of responsiveness. The term "upregulated" as used herein, refers to an overall increase of no less than 10%, 15%, 20%, 25%, 30%, 35%, 40%, 45%, 50%, 55%, 60%, 65%, 70%, 75%, 80% or greater, in the cholesterol level in the test sample as detected using the antibodies or antigen-binding fragments provided herein, as compared to the cholesterol level in a reference sample as detected using the same antibody. The reference sample can be a control sample obtained from a healthy or non-diseased individual, or a healthy or non-diseased sample obtained from the same individual from whom the test sample is obtained.

The antibodies or antigen-binding fragments disclosed herein may be administered alone or in combination with one or more additional therapeutic means or agents. For example, the antibodies or antigen-binding fragments disclosed herein may be administered in combination with statin, an HMG-CoA reductase inhibitor other than a statin, niacin (nicotinic acid), a cholesterol absorption inhibitor, a cholesteryl ester transfer protein (CETP), a bile acid sequestrant, a fibrate, a phytosterol; or a modulator of lipid/lipid concentration ratios selected from a small molecule, peptidomimetic, an antisense RNA, a small interfering RNA (siRNA), and a natural or modified lipid. In certain embodiments, a cholesterol absorption inhibitor is ezetimibe or SCH-48461; a CETP is evacetrapib, anacetrapib or dalcetrapib; a bile acid sequestrant is preferably colesevelam, cholestyramine or colestipol; a fibrate is preferably fenofibrate, gemfibrozil, clofibrate, or bezafibrate.

In certain of these embodiments, an antibody or antigen-binding fragment as disclosed herein that is administered in combination with one or more above additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLE 1: ANTIBODY AND OTHER PROTEINS GENERATION 1.1 Human and Murine PCSK9

Human and murine PCSK9 genes were inserted into expression vector pcDNA™ 3.3 with a 6-His tag or murine Fc (mFc) fused at the C-terminus. The plasmids were then transfected to HEK293 cells using PlasFect (Bioline USA, BIO-46026). The His-tag proteins were purified from harvested supernatant using a Ni-column (Qiagen Inc). The mFc-fused proteins were purified using Protein A column (MABSELECT SURE™, GE).

1.2 Human LDL-R

The gene of LDL receptor extracellular domain was inserted into vector pcDNA™ 3.3 with a C-terminal 6-His tag. The plasmid was transfected to HEK293 cells using PlasFect (Bioline USA, BIO-46026). LDL-R protein was firstly purified from harvested supernatant using a Ni column (Qiagen Inc), followed by purification using ion-exchange column.

1.3 Reference Antibody

Reference antibody BMK.115 was generated based on the sequence of 21B12 in the U.S. Pat. No. 8,889,834B2. The plasmids containing VH and VL gene were co-transfected into HEK293 cells. Antibody was purified form harvested supernatant using Protein A column (MabSelect SuRe™, GE).

EXAMPLE 2: ANTIBODY GENERATION 2.1 Immunization

OMNIRAT® (OMT) which contains human immunoglobulin variable domain genes were used to generate antibodies with fully human VH and VL. OMNIRAT® were injected with human PCSK9 protein via foot pads approximately every 3 days. First titer test was performed after 6 times injection. Afterwards, the rats were injected every other week.

2.2 Serum Titer Detection

Enzyme linked immunosorbent assay (ELISA) was used to measure titers of antibody in rat serum. ELISA plates (Nunc) were coated with human PCSK9 at 1 µg/ml overnight at 4° C., and then blocked with blocking buffer (1XPBS/2% BSA) for 1 h at room temperature. Rat serum was 1:3 titrated starting at 1:100 dilution in blocking buffer and incubated for 1 h at room temperature. The plates were then washed and subsequently incubated with secondary antibody goat anti rat IgG1 HRP (Bethyl) and goat anti rat IgG2b HRP (Bethyl) for 45 min. After washing, TMB substrate was added and the interaction was stopped by 2M HCl. The absorbance at 450 nm was read using a microplate reader (Molecular Device).

2.3 Immunization and Hybridoma Generation

Lymph nodes and spleen were collected from immunized mice under sterile condition, and lymphocytes were prepared using FICOLL-PAQUE™ PLUS gradient centrifugation. The isolated cells were then fused with myeloma cell P3 at a ratio of 1:1 using electrofusion device (BTX™ ECM2001). Cells were transferred to ½ HA media after fusion. $5\times10^5$ cells were seeded per 96-well plate.

Titers of the antigen-specific antibody in serum were determined by ELISA assay. The rats with serum titer of 312500 or higher were selected for hybridoma fusion.

2.4 Hybridoma Screening

Binding assay by ELISA: Plates (Nunc) were coated with Streptavidin at 1 µg/ml overnight at 4° C. After blocking and washing, 250 ng/ml PCSK9-biotin was added and incubated for 1 h. Then hybridoma supernatants were transferred to the plates and incubate at room temperature for 1 h. The plates were then washed and subsequently incubated with secondary antibody goat anti rat IgG1 HRP (Bethyl) and goat anti rat IgG2b HRP (Bethyl) for 45 min. After washing, TMB substrate was added and the interaction was stopped by 2M HCl. The absorbance at 450 nm was read using a microplate reader (Molecular Device).

Blocking assay by ELISA: Plates (Nunc) were coated with LDL-R overnight at 4° C. Hybridoma supernatants were mixed with 250 ng/ml PCSK9-mFc-biotin and incubated at 4° C. overnight. After blocking and washing, the mixture were added to the plates and incubated for 1 h. The plates were then washed and subsequently incubated with streptavidin-HRP. After washing, TMB substrate was added and the interaction was stopped by 2M HCl. The absorbance at 450 nm was read using a microplate reader (Molecular Device).

Hybridoma supernatant was used for primary screen. The primary binding screen identified a total of 13000 antigen-specific hybridomas from 4 fusions. The antigen specific hybridomas were then screened by ELISA blocking assay. The blocking assay resulted in 104 hybridomas which can block the binding of human PCSK9 to human LDL-R. The selected antibodies with both binding and blocking activities were purified from hybridoma supernatant. In the meanwhile, the selected hybridoma lines were subcloned by limiting dilution. Hybridoma subclones were verified by binding and blocking ELISA assay, and their isotypes were also detected.

Cellular LDL uptake assay was performed using purified antibodies. Binding and blocking activities were also further evaluated using ELISA. The selection of final lead clones was based on binding affinity, blocking IC50 of PCSK9 binding to LDL-R, and restoration activity of cellular LDL-uptake.

2.5 Subcloning

Hybridoma cells of each selected lines were plated in 96-well plates at densities of 0.5, 1 and 5 cell/well. The single clones were picked and tested in binding ELISA. Three subclones of each hybridoma line were selected and frozen.

2.6 Isotype

Antibody Isotype was identified by ELISA (see Table 2). Plates (Nunc) were coated with goat anti rat IgG1, IgG2a, IgG2b, IgG2c and IgM antibodies (Bethyl) at 1 µg/ml overnight at 4° C. After blocking and washing, the hybridoma supernatants were transferred to the coated plates and incubate at room temperature for 1 h. The plates were then incubated with secondary antibody goat anti-human kappa HRP or goat anti human lambda HRP (Southern Biotech) for 45 min. After washing, TMB substrate was added and the interaction was stopped by 2M HCl. The absorbance at 450 nm was read using a microplate reader (Molecular Device).

TABLE 2

Antibody Isotype

| Ab | Isotype |
|---|---|
| 18.156.8 | IgG1/kappa |
| 11.4.1 | IgG1/kappa |
| 15.14.2 | IgG2b/Lambda |
| 17.72.3 | IgG1/kappa |
| 19.3.8 | IgG1/Lambda |
| 18.136.7 | IgG1/kappa |

2.7 Antibody Purification

Harvested hybridoma supernatants were loaded to Protein A column (MabSelect SuRe™, GE) after adjusting pH to 7.0. Antibodies were eluted by Glycine followed with immediately neutralization using 1 M Tris. Antibody concentration was tested by NANODROP™ (Thermal-Fisher). The purity of proteins was evaluated by SDS-PAGE (Invitrogen, NUPAGE™ 4%-12% Bis-Tris Gel) and HPLC-SEC (Agilent).

EXAMPLE 3: GENERATION OF FULLY HUMAN ANTIBODY 3.1 Hybridoma Sequencing

Extract RNA from hyridoma cell using TRIZOL' reagent (Invitrogen-15596018). cDNA was amplifiedy using 5'-RACE kit (Takara-28001488), followed by PCR amplification using 3'-degenerated primers and 3'-adaptor primers (EX TAQ™: Takara-RR001B). PCR fragments was inserted into pMD18-T vector (Takara-D101C) and sent for sequencing (Shanghai Biosune). Variable region sequences (amino acid sequences and nucleic acid sequences) of selected antibodies 11.4, 18.156.8, 15.14.2, 17.72.3, 18.136.7, 19.3.8 and 40409 are shown as SEQ ID NOs: 73-100.

3.2 Generation of Recombinant Fully Human Antibody

The V-region DNA of each antibody (human-rat chimeric antibody) was cloned into a pcDNA™3.3 vector containing human constant region gene. HEK293 cell was transfected with plasmids that encode antibody heavy and light chains. Supernatant from transfected cells was harvested by removing cells and filtration. Antibodies were purified by Protein A column (Mab Select SuRe™, GE) and buffer exchanged into PBS. Antibody concentration was detected by NANODROP™. Purity was evaluated by SDS-PAGE (Invitrogen, NUPAGE™4%-12% Bis-Tris Gel) and HPLC-SEC (Agilent).

3.3 Affinity Maturation

A saturated mutagenesis of 11.4 heavy chain (HC)-CDR3 library was generated and screened by binding ELISA assay, and single mutations that increased PCSK9 binding compared to the parental clone were selected. A combinatorial library of selected mutations was then generated. The clones with certain mutation combinations were selected based on ELISA binding and SPR $k_{off}$ ranking results.

Two random mutant libraries were generated using 11.4 as a template. The libraries were selected by 2 rounds of panning and screening. Mutations that improve the binding affinity were selected and combined with mutations selected with the saturated library.

Figure 1:
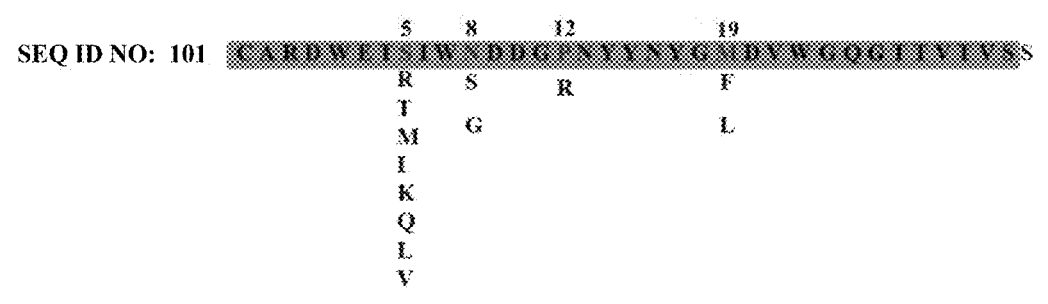

A saturated mutagenesis library of 11.4 HC-CDR3 was generated and screened by binding ELISA assay, and single mutations that increased PCSK9 binding compared to the parental clone were selected (FIG. 1). A combinatorial library of selected mutations was then generated. The clones with certain mutation combinations were selected based on ELISA binding and SPR $k_{off}$ ranking results. Combination of 3 mutations in one CDR yielded 10-fold affinity improvement in IgG-converted clones B4G2 and C1B4 (Table 3).

TABLE 3

Binding affinity of affinity matured antibodies

| Antibody | ka (1/Ms) | kd (1/s) | KD (M) |
|---|---|---|---|
| A1D11 | 5.53E+05 | 3.73E−04 | 6.73E−10 |
| B1F6 | 1.25E+06 | 2.41E−04 | 1.93E−10 |
| B4G2 | 1.23E+06 | 1.66E−04 | 1.35E−10 |
| B5C1 | 5.96E+05 | 3.87E−04 | 6.49E−10 |
| C1B4 | 1.56E+06 | 2.01E−04 | 1.29E−10 |
| 11.4.4 | 1.31E+06 | 1.31E−03 | 1.00E−09 |
| BMK.115 | 1.48E+05 | 1.86E−05 | 1.25E−10 |

Two random mutant libraries were also generated using 11.4 as a template. Libraries selection by 2 rounds of panning yielded 5 clones with the affinity-improving mutations. 3 combinations of these mutations were selected and introduced to B4G2 to yield clones 40408, 40409 and 40410. The additional mutation resulted 2-fold further affinity improvement. The final affinity matured lead Abs have 2-fold higher affinity compared to BMK.115 (Table 4).

TABLE 4

Binding affinity of affinity matured antibodies

| Antibody | ka (1/Ms) | kd (1/s) | KD (M) |
|---|---|---|---|
| 40408 | 1.38E+06 | 9.90E−05 | 7.17E−11 |
| 40409 | 1.73E+06 | 9.05E−05 | 5.23E−11 |

TABLE 4-continued

Binding affinity of affinity matured antibodies

| Antibody | ka (1/Ms) | kd (1/s) | KD (M) |
|---|---|---|---|
| 40410 | 1.48E+06 | 9.50E−05 | 6.41E−11 |
| B4G2 | 1.14E+06 | 1.89E−04 | 1.65E−10 |

3.4 Production of Fully Human Antibodies from Transient Transfected Cell Line 3.4.1 18.156.8 (hIgG4)

Figure 3:
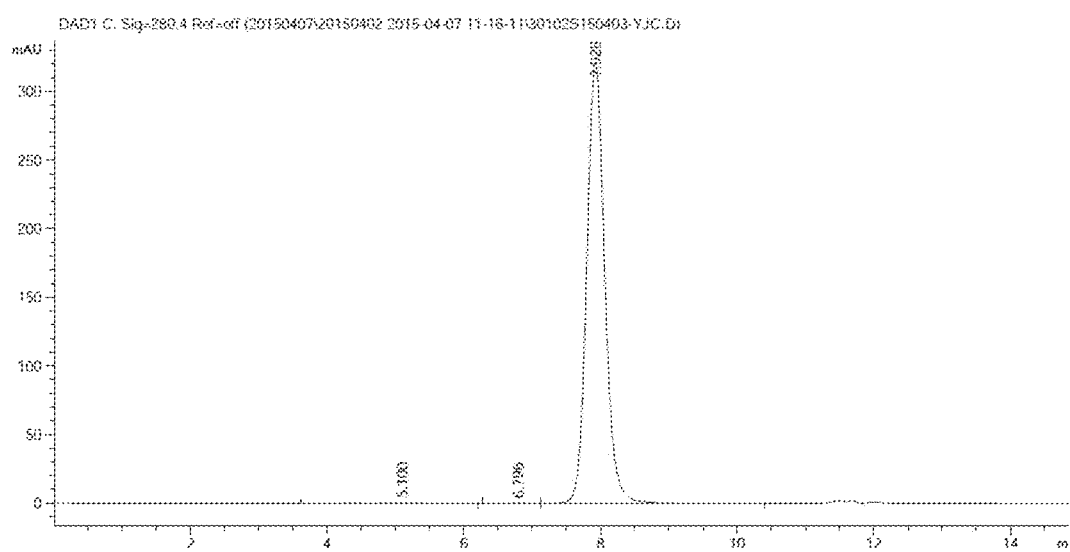
FIG. 3 shows 99.6% purity of the fully human 18.156.8 (hIgG4) as measured by HPLC-SEC.

Fully human antibody 18.156.8 (hIgG4) migrates with the apparent molecular mass of 25 kDa and 55 kDa in SDS-PAGE under reducing conditions corresponding to light chain and heavy chain (see FIG. 2). The main band under non-reducing condition is the whole IgG with M.W. of ~150 KD. The purity is 99.6% as determined by HPLC-SEC (FIG. 3). Endotoxin is <0.5 EU/mg.

3.4.2 40409 (hIgG4)

Figure 4:
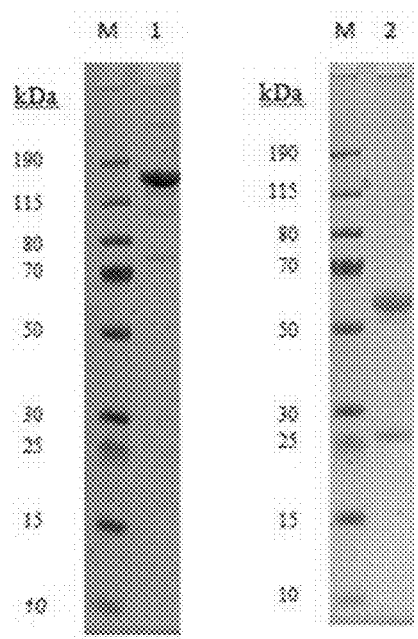
FIG. 4 shows the staining of fully human antibody 40409 (hIgG4) in SDS-PAGE gel. M: Protein Marker; Lane1: 40409 (hIgG4), Reduced; Lane2: 40409 (hIgG4), Non-reduced.
Figure 5:
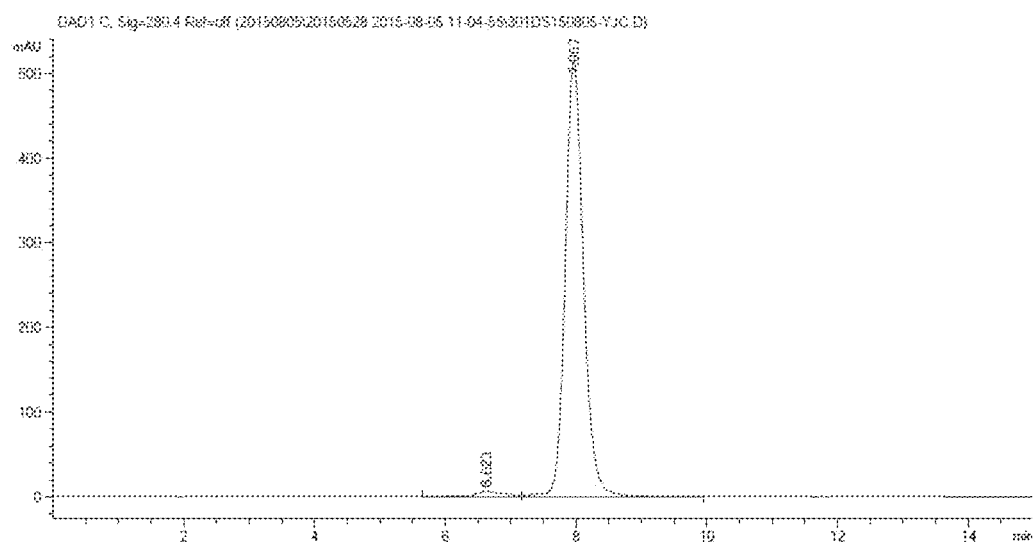
FIG. 5 shows 98% purity of the fully human 40409 (hIgG4) as measured by HPLC-SEC.

Fully human antibody 18.156.8 (hIgG4) migrates with the apparent molecular mass of 25 kDa and 55 kDa in SDS-PAGE under reducing conditions corresponding to light chain and heavy chain (see FIG. 4). The main band under non-reducing condition is the whole IgG with M.W. of ~150 KD. The purity is 98% as determined by HPLC-SEC (see FIG. 5). Endotoxin is <0.5 EU/mg.

3.4.3 15.14.2-uAb-IgG4L

Figure 6:
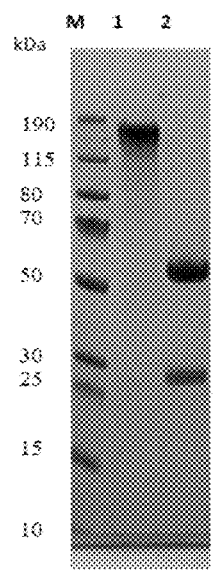
FIG. 6 shows the staining of fully human antibody 15.14.2-uAb-IgG4L in SDS-PAGE gel. M: Protein Marker; Lane1: 15.14.2-uAb-IgG4L, Reduced; Lane2: 15.14.2-uAb-IgG4L, Non-reduced.
Figure 7:
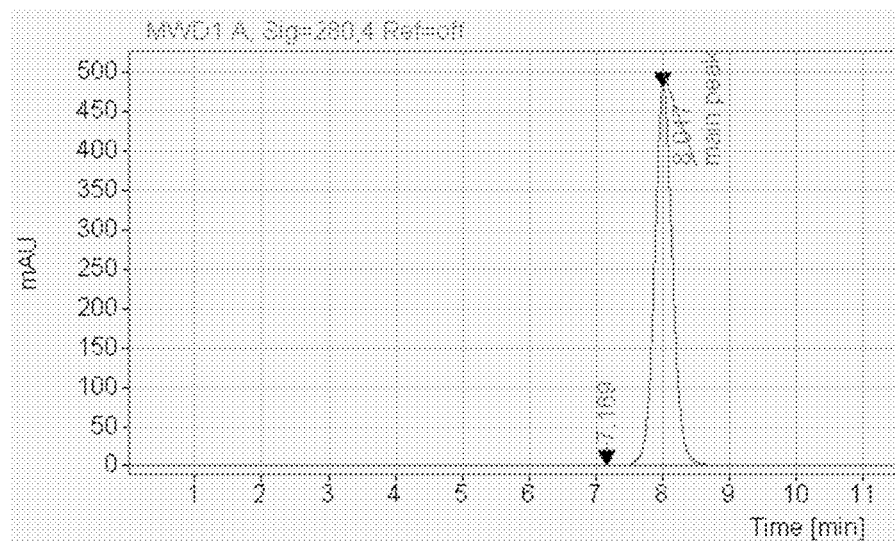
FIG. 7 shows 99.8% purity of the fully human 15.14.2-uAb-IgG4L as measured by HPLC-SEC.

Fully human antibody 15.14.2-uAb-IgG4L migrates with the apparent molecular mass of 25 kDa and 55 kDa in SDS-PAGE under reducing conditions corresponding to light chain and heavy chain (see FIG. 6). The main band under non-reducing condition is the whole IgG with M.W. of ~150 KD. The purity is 99.8% as determined by HPLC-SEC (see FIG. 7). Endotoxin is <0.5 EU/mg.

3.4.4 17.72.3-uAb2-IgG4K

Figure 8:
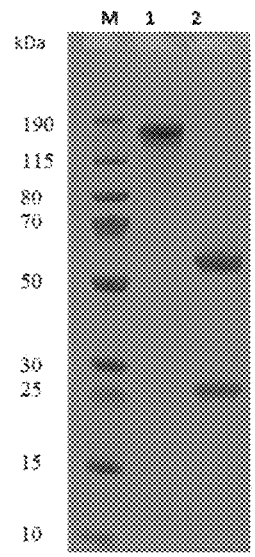
FIG. 8 shows the staining of fully human antibody 17.72.3-uAb2-IgG4K in SDS-PAGE gel. M: Protein Marker; Lane1: 17.72.3-uAb2-IgG4K, Reduced; Lane2: 17.72.3-uAb2-IgG4K, Non-reduced.
Figure 9:
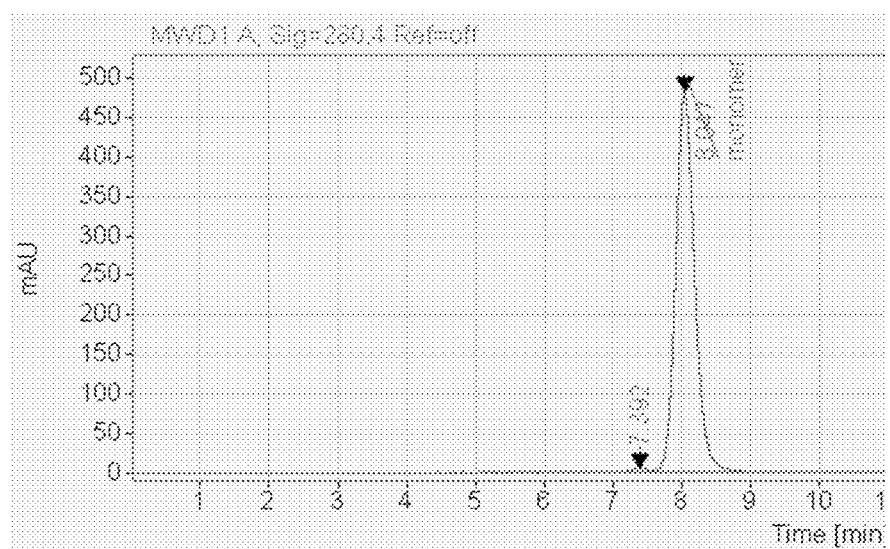
FIG. 9 shows 98.9% purity of the fully human 17.72.3-uAb2-IgG4K as measured by HPLC-SEC.

Fully human antibody 17.72.3-uAb2-IgG4K migrates with the apparent molecular mass of 25 kDa and 55 kDa in SDS-PAGE under reducing conditions corresponding to light chain and heavy chain (see FIG. 8). The main band under non-reducing condition is the whole IgG with M.W. of ~150 KD. The purity is 98.9% as determined by HPLC-SEC (see FIG. 9). Endotoxin is <0.5 EU/mg.

3.4.5 18.136.7-IgG4K

Figure 10:
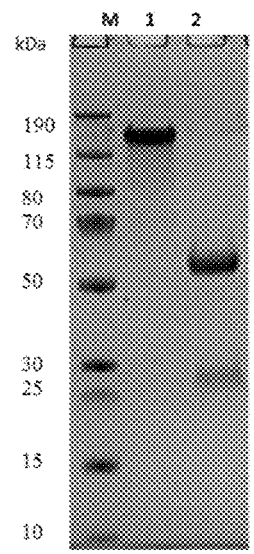
FIG. 10 shows the staining of fully human antibody 18.136.7-IgG4K in SDS-PAGE gel. M: Protein Marker; Lane1: 18.136.7-IgG4K, Reduced; Lane2: 18.136.7-IgG4K, Non-reduced.
Figure 11:
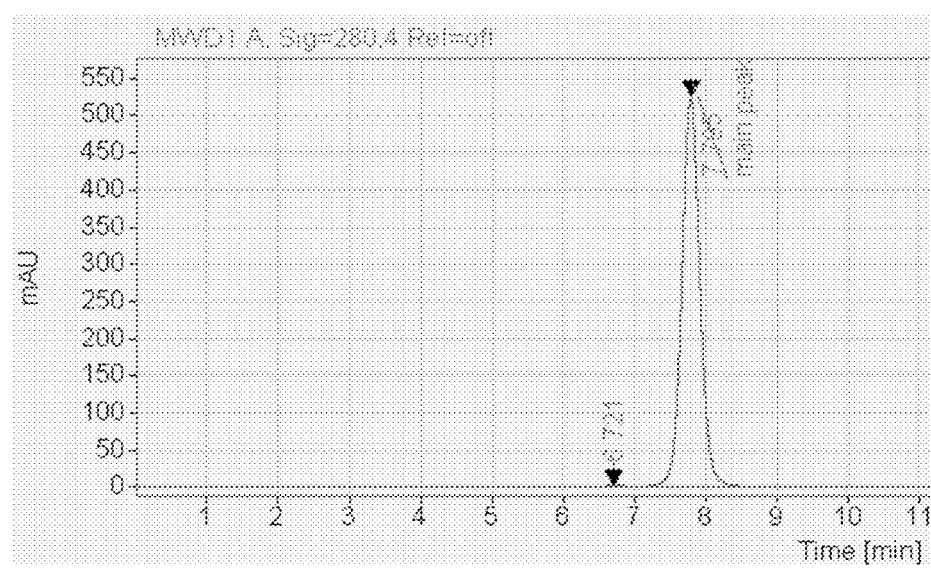
FIG. 11 shows 99.2% purity of the fully human 18.136.7-IgG4K as measured by HPLC-SEC.

Fully human antibody 18.136.7-IgG4K migrates with the apparent molecular mass of 25 kDa and 55 kDa in SDS-PAGE under reducing conditions corresponding to light chain and heavy chain (see FIG. 10). The main band under non-reducing condition is the whole IgG with M.W. of ~150 KD. The purity is 99.2% as determined by HPLC-SEC (see FIG. 11). Endotoxin is <0.5 EU/mg.

3.4.6 19.3 0.8-uAb 1-IgG4L

Figure 12:
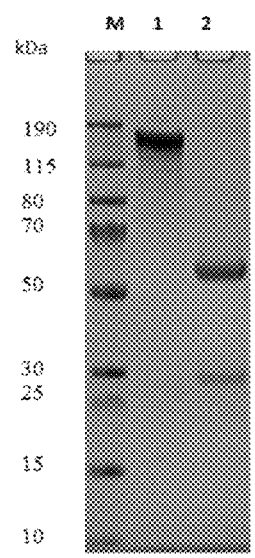
FIG. 12 shows the staining of fully human antibody 19.3.8-uAb1-IgG4L in SDS-PAGE gel. M: Protein Marker; Lane1: 19.3.8-uAb1-IgG4L, Reduced; Lane2: 19.3.8-uAb1-IgG4L, Non-reduced.
Figure 13:
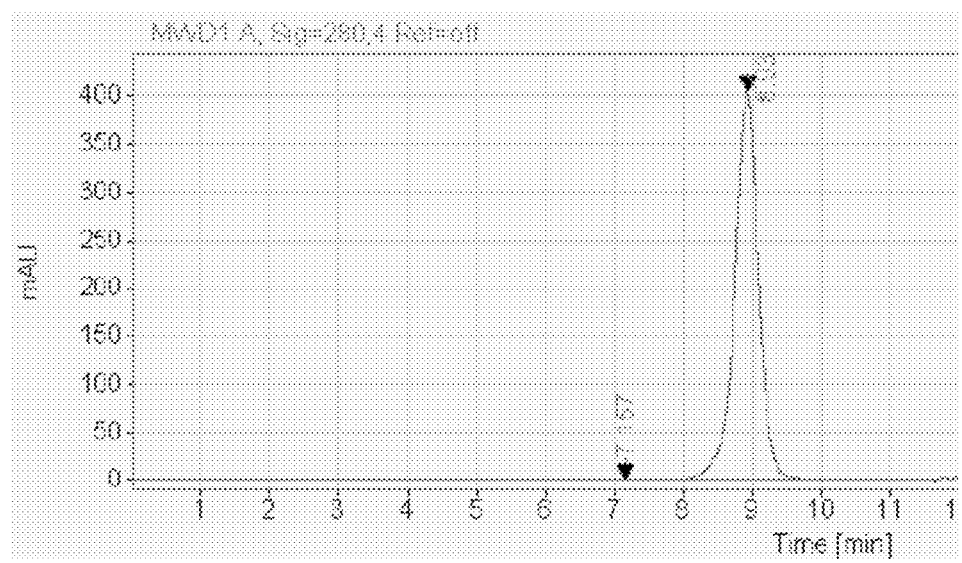
FIG. 13 shows 99.9% purity of the fully human 19.3.8-uAb1-IgG4L as measured by HPLC-SEC.

Fully human antibody 19.3.8-uAb1-IgG4L migrates with the apparent molecular mass of 25 kDa and 55 kDa in SDS-PAGE under reducing conditions corresponding to light chain and heavy chain (see FIG. 12). The main band under non-reducing condition is the whole IgG with M.W. of ~150 KD. The purity is 99.9% as determined by HPLC-SEC (see FIG. 13). Endotoxin is <0.5 EU/mg.

Figure 14:
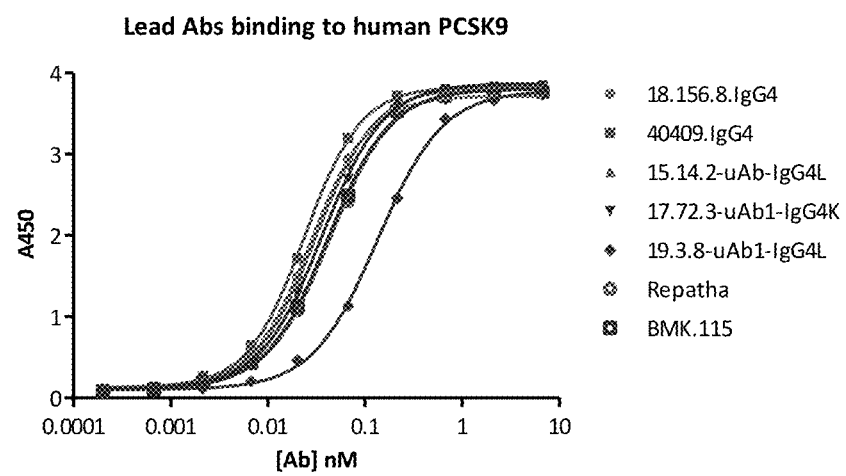
FIG. 14 presents the binding of fully human anti-PCSK9 antibodies to human PCSK9 as measured by ELISA.
Figure 15:
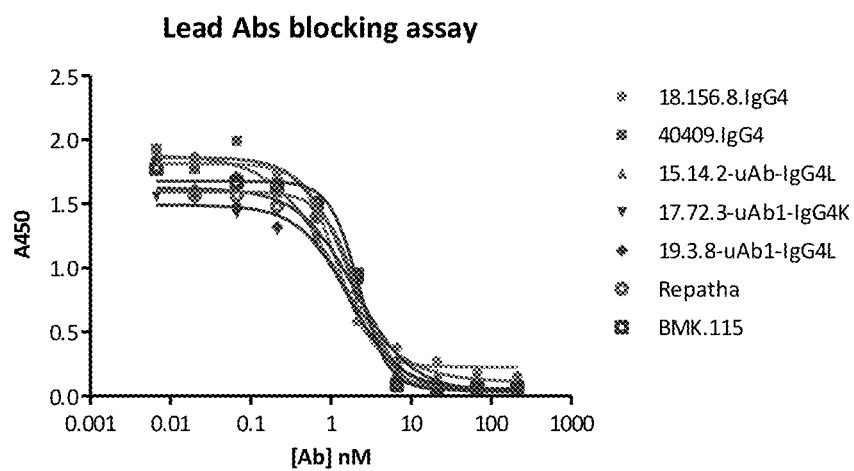
FIG. 15 presents the blocking of fully human anti-PCSK9 antibodies to the binding of PCSK9 to LDL receptor (LDL-R) as measured by ELISA.
Figure 16A:
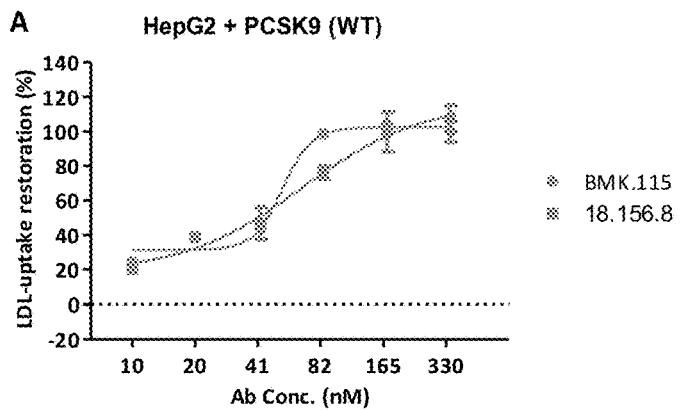
FIG. 16 shows the results of restoring the low-density lipoprotein (LDL)-uptake assay of the fully human anti-PCSK9 antibody 18.156.8 in liver hepatocellular carcinoma (HepG2) cell and in Huh-7 cell by binding wild type (FIGS. 16A and 16B) and mutant PCSK9 (D374Y) (FIGS. 16C and 16D), respectively.
Figure 16B:
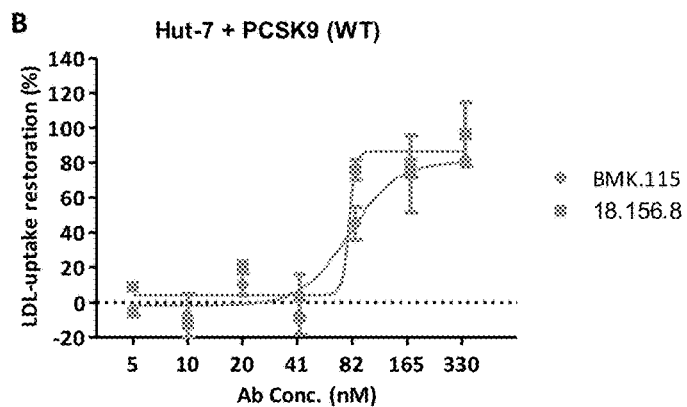
Figure 16C:
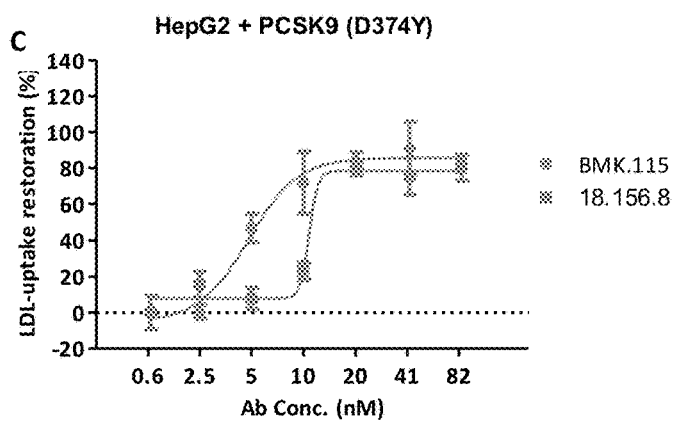
Figure 16D:
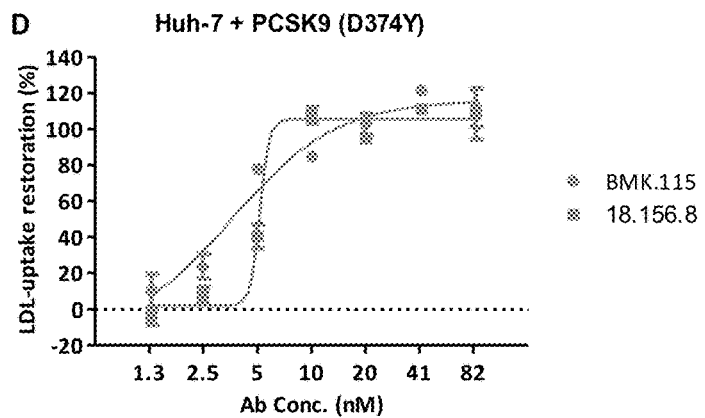
Figure 17A:
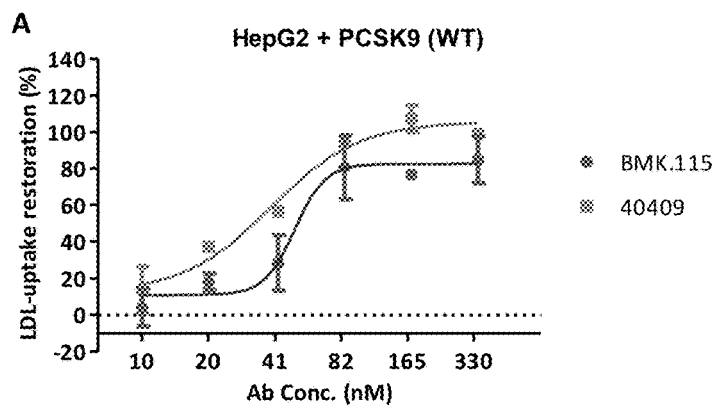
FIG. 17 shows the results of restoring the low-density lipoprotein (LDL)-uptake assay of the fully human anti-PCSK9 antibody 40409 in HepG2 cell and in Huh-7 cell using both wild type (FIGS. 17A and 17B) and mutant PCSK9 (D374Y) (FIGS. 17C and 17D).
Figure 17B:
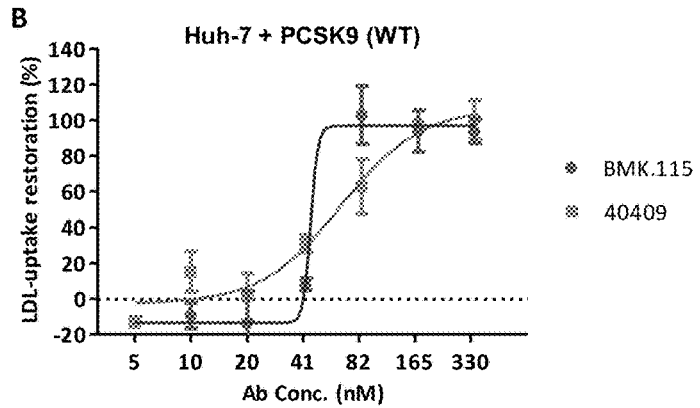
Figure 17C:
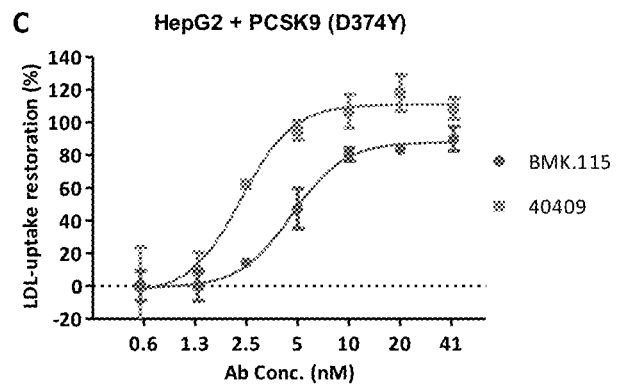
Figure 17D:
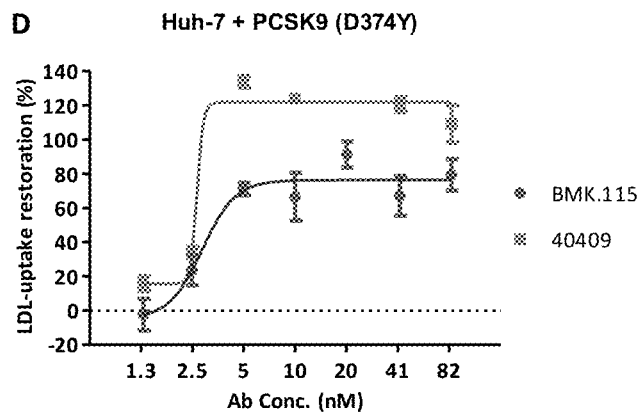

EXAMPLE 4: LEAD ANTIBODY CHARACTERIZATION 4.1 Binding and Blocking Activities of Fully Human Antibodies The activities of fully human antibodies binding to PCSK9 were confirmed by ELISA. (FIG. 14). The activities of fully human antibodies to blocking the binding of PCSK9 to LDL-R were confirmed by competitive ELISA (FIG. 15). The binding EC50 and blocking IC50 values were summarized in Tables 5 and 6. The lead antibodies 18.156.8 (hIgG4), 40409 (hIgG4), 15.14.2-uAb-IgG4L and 17.72.3-uAb2-IgG4K exhibited comparable binding and blocking activities with BMK.115 and REPATHA™.

TABLE 5

Summary of binding activity

| Antibody | Binding EC50 (nM) |
|---|---|
| 18.156.8 (hIgG4) | 0.028 |
| 40409 (hIgG4) | 0.024 |
| 15.14.2-IgG4L | 0.031 |
| 17.72.3-IgG4K | 0.036 |
| 19.3.8-IgG4L | 0.13 |
| Repatha | 0.044 |
| BMK.115 | 0.041 |

TABLE 6

Summary of blocking activity

| Antibody | Blocking IC50 (nM) |
|---|---|
| 18.156.8 (hIgG4) | 1.22 |
| 40409 (hIgG4) | 1.75 |
| 15.14.2-IgG4L | 1.121 |
| 17.72.3-IgG4K | 1.673 |
| 19.3.8-IgG4L | 2.004 |
| Repatha | 2.207 |
| BMK.115 | 2.233 |

4.2 LDL Uptake Assay of Fully Human Antibodies

HepG2 or Huh-7 cells were seeded in a 96-well plate at a density of $1\times10^5$ cells/well in DMEM medium containing 10% FBS. The plate was kept in a 37° C. incubator overnight. The medium was replaced with DMEM without FBS. Mixture of human PCSK9 and various concentrations of antibodies were added to the cells. The final concentration of wild type PCSK9 and mutant PCSK9 (D374Y) was 20 μg/ml and 1.3 μg/ml, respectively. After 1 hour, Bodipy FL-labeled LDL (Invitrogen L-3483) was added to the cells to make a final concentration of 1.5 μg/ml. After incubation in a 37° C. incubator for 3 hours, medium containing LDL in the plate was discarded. The cells were trypsinized and washed twice. LDL-uptake was characterized by the fluorescence of Bodipy FL-labeled LDL in the cells determined by FACS. LDL-uptake restoration rate was calculated following the formula: LDL-uptake restoration (%)= $(\text{MFI}_{sample}-\text{MFI}_{LDL+Ag1H})/(\text{MFI}_{LDL\ only}-\text{MFI}_{LDL+Ag1H})\times 100\%$.

Figure 18:
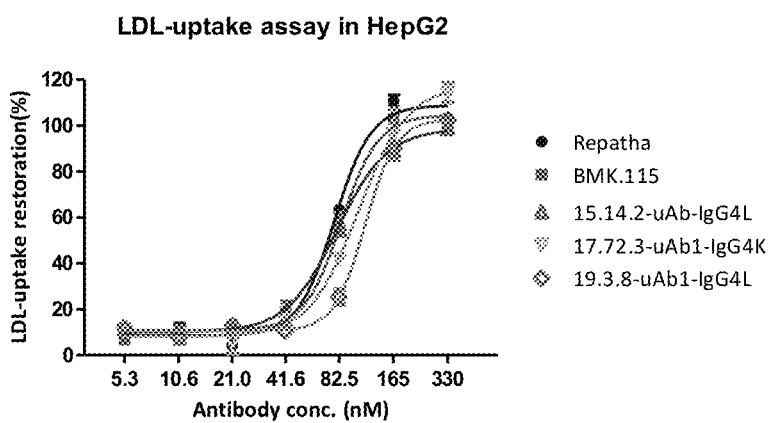
FIG. 18 shows the results of restoring the low-density lipoprotein (LDL)-uptake assay of the fully human anti-PCSK9 antibody 15.14.2-uAb1-IgG4L, 17.72.3-uAb1-IgG4K and 19.3.8-uAb1-IgG4L in HepG2 cell.

The final lead antibodies 18.156.8 and 40409 were evaluated in LDL-uptake assay in HepG2 and Huh-7 cells (see FIGS. 16 and 17) using both of wild type and mutant PCSK9. The result demonstrates that 18.156.8 and 40409 can efficiently restore the cellular LDL-uptake when WT PCSK9 or mutant PCSK9 exist. The ability of antibody 15.14.2, 17.72.3 and 19.3.8 to restore cellular LDL-uptake was evaluated using HepG2 cell with wild type PCSK9 (see FIG. 18). The result demonstrates that 15.14.2, 17.72.3 and 19.3.8 can efficiently restore the cellular LDL-uptake when WT PCSK9 exists. The IC50 value of each antibody was summarized in Table 7 and 8.

TABLE 7

IC50 of antibody in LDL-uptake restoration assay

| IC50 (nM) | HepG2 | | Huh-7 | |
| --- | --- | --- | --- | --- |
| | PCSK9 (WT) | PCSK9 (D374Y) | PCSK9 (WT) | PCSK9 (D374Y) |
| BMK.115 | 52.3 | 4.8 | 76.8 | 3.6 |
| 18.156.8 (hIgG4) | 65.1 | 10.8 | 76.1 | 5.2 |
| BMK.115 | 48.9 | 4.6 | 43.7 | 2.9 |
| 40409 (hIgG2) | 38.3 | 2.3 | 63.7 | 2.7 |

TABLE 8

LDL-uptake assay in HepG2

| Antibody | IC50 (nM) |
| --- | --- |
| 15.14.2-IgG4L | 80 |
| 17.72.3-IgG4K | 106 |
| 19.3.8-IgG4L | 115 |
| Repatha | 77.6 |
| BMK.115 | 84.7 |

4.3 Kinetic Affinity 4.3.1 Binding Kinetics by SPR

Antibody binding affinity to human and rhesus PCSK9 was detected by SPR assay using BIACORE™ T200. Each antibody was captured on a Protein A or or anti-human IgG Fc antibody immobilized CM5 sensor chip (GE). Human or rhesus PCSK9 at different concentrations were injected over the sensor chip at a flow rate of 30 µL/min for an association phase of 180 s, followed by 1200 s dissociation. The chip was regenerated by 2 M $MgCl_2$ after each binding cycle.

The sensorgrams for blank surface and buffer channel were subtracted from the test sensorgrams. The experimental data was fitted by 1:1 model using Langmiur analysis. Molecular weight of 85 KDa was used to calculate the molar concentration of analyte.

4.3.2 Cross-Reactivity to Rhesus PCSK9 by ELISA

ELISA plates (Nunc) were coated with anti-His Ab (Genscript) at 1 µg/ml overnight at 4° C. After blocking and washing, 1 µg/ml rhesus PCSK9-His (Sino Biological) was added and incubated for 1 h. The antibody samples were added to the plates and incubate at room temperature for 1 h. The plates were then washed and subsequently incubated with secondary antibody goat anti rat IgG1 HRP (Bethyl) and goat anti rat IgG2b HRP (Bethyl) for 45 min. After washing, TMB substrate was added and the interaction was stopped by 2M HCl. The absorbance at 450 nm was read using a microplate reader (Molecular Device).

Kinetic affinities of antibody leads were measured by SPR assay. The affinities to human and monkey PCSK9 are summarized in Table 9.

TABLE 9

Kinetic affinity to human and monkey PCSK9

| | Kinetic affinity to human PCSK9 | | |
| --- | --- | --- | --- |
| Antibody | ka (1/Ms) | kd (1/s) | KD (M) |
| 18.156.8 | 2.48E+05 | 1.46E-04 | 5.89E-10 |
| 40409 | 1.73E+06 | 9.05E-05 | 5.23E-11 |
| 15.14.2 | 3.24E+05 | 8.09E-05 | 2.50E-10 |
| 17.72.3 | 1.37E+04 | 4.68E-05 | 3.42E-09 |
| 19.3.8 | 1.54E+04 | 2.71E-04 | 1.75E-08 |
| BMK.115 | 1.48E+05 | 1.86E-05 | 1.25E-10 |

TABLE 9-continued

Kinetic affinity to human and monkey PCSK9

| | Kinetic affinity to monkey PCSK9 | | |
| --- | --- | --- | --- |
| Antibody | ka (1/Ms) | kd (1/s) | KD (M) |
| 18.156.8 | 8.61E+05 | 3.19E-05 | 3.71E-11 |
| 40409 | 2.27E+06 | 9.39E-04 | 4.13E-10 |
| 15.14.2 | 4.52E+05 | 3.10E-04 | 6.87E-10 |
| 17.72.3 | 1.10E+05 | 0.002256 | 2.05E-08 |
| 19.3.8 | 6.16E+05 | 4.41E-03 | 7.16E-09 |
| BMK.115 | 1.15E+06 | 6.62E-05 | 5.75E-11 |

4.4 Serum Stability

Antibodies were incubated in freshly isolated human serum (serum content>95%) at 37° C. for 0, 1, 3, 7, 14 days, respectively. After incubation at 37° C., samples were rapidly frozen in dry-ice-ethanol bath and kept at −80° C. The samples were rapidly thawed before stability test. The plates were coated with streptavidin in $Na_2CO_3/NaHCO_3$(pH 9.2) buffer at 4° C. overnight. The plates were washed with 0.1% TWEEN™-PBS once before being blocked with 2% BSA/PBS. Biotin-labeled PCSK9 was added and incubated for 1 hr. After washing, then diluted serum samples were transferred to the plates and incubated for 1 hr at room temperature. Goat anti-human-HRP antibody were added to the wells and incubated for 1 hr. After washing, TMB substrate was added and the interaction was stopped by 2 M HCl. The absorbance at 450 nm was read using a microplate reader (Molecular Device).

Figure 19:
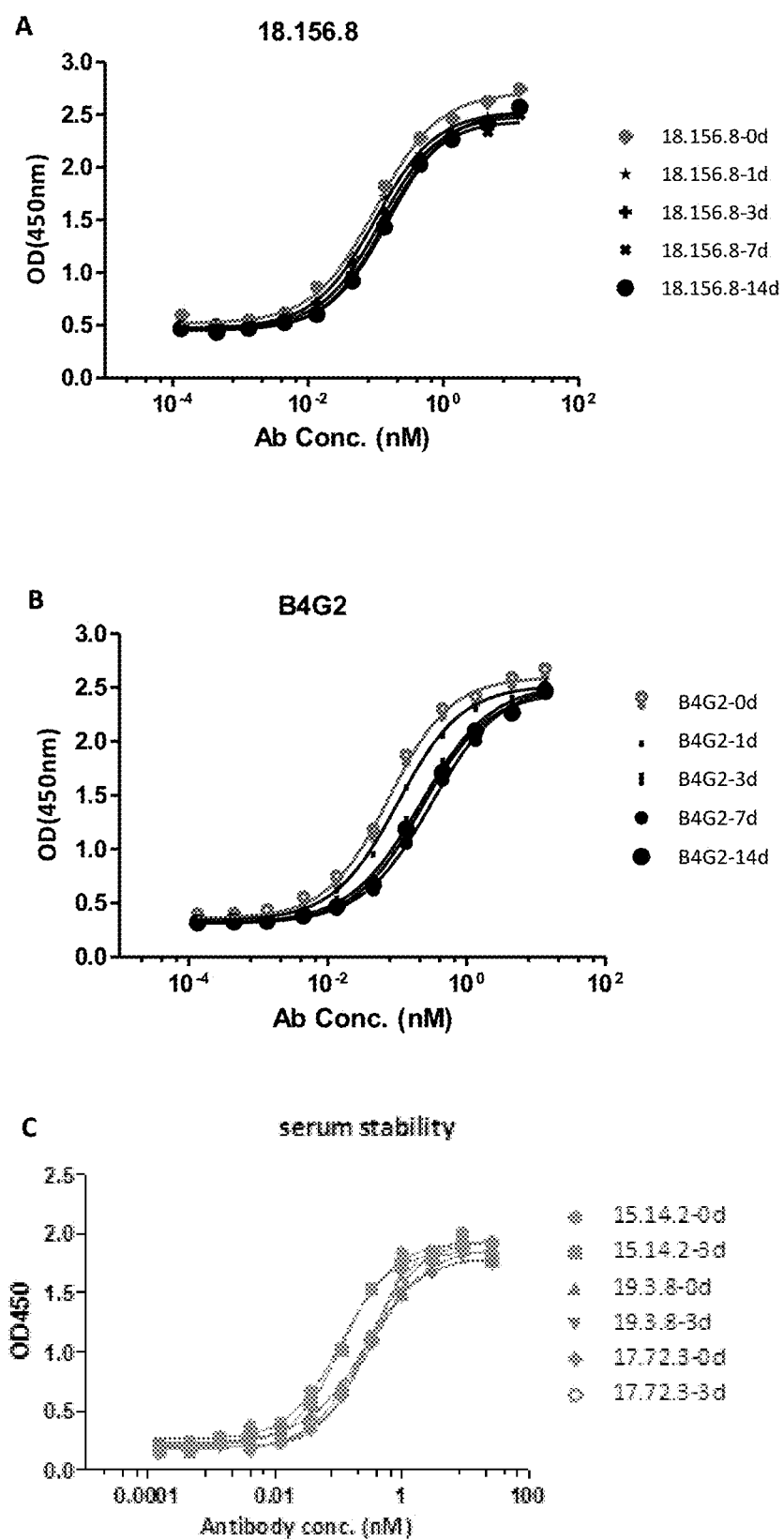
FIG. 19 illustrates the stability of fully human PCSK9 antibodies (FIG. 19A: 18.156.8; 19B: B4G2; 19C: 15.14.2, 19.3.8 and 17.72.3) incubated with human serum as indicated by the concentration measured by ELISA binding assay.

The antibody binding to human PCSK9 was tested by ELISA after incubation in human serum at 37° C. (FIG. 19). The binding of antibody 18.156.8 and B4G2 after incubation of 1, 3, 7 and 14 days did not show significant difference from the pre-incubation sample. Therefore, antibody 18.156.8 and B4G2 are both stable in human serum for 14 days at 37° C. The binding of antibody 15.14.2, 17.72.3 and 19.3.8 after incubation of 3 days did not show significant difference from the pre-incubation sample.

EXAMPLE 5: ANIMAL STUDY 5.1 Single-Dose Efficacy in Non-Human Primates

LDL-C and HDL-C concentration in monkey serum was tested on Roche/Hitachi cobas c systems using LDLC and HDLC3 kits (Roche). Total cholesterol (TCHO) was tested by cholesterol FS kit (DiaSys).

5.1.1 Study 1: A total of 6 female cynomolgus monkeys, approximately 3 to 4 years old and weighing 2.6 to 2.9 kg, at dosing initiation. Six female monkeys were randomly assigned to 6 groups of 1 female/group. Six groups of 1 female monkey each received 10 or 30 mg/kg of BMK.115, 18.156.8 (hIgG4) or 40409 (hIgG4) by a single dose intravenous injection. The first dosing day was defined as Day 1. The animals of each group were observed for 36 days following dosing:

| Group/ Label color | Test Article | Dose[a] Dose (mg/kg) | Volume (mL/kg) | Numbering of Animals Female |
| --- | --- | --- | --- | --- |
| 1/Green | BMK.115 | 10 mg/kg | 1.39 | 1501 |
| 2/Yellow | BMK.115 | 30 mg/kg | 4.17 | 2501 |
| 3/Red | 18.156.8 (hIgG4) | 10 mg/kg | 2.60 | 3501 |

-continued

| Group/<br>Label color | Test Article | Dose[a]<br>Dose<br>(mg/kg) | Volume<br>(mL/kg) | Numbering<br>of Animals<br>Female |
|---|---|---|---|---|
| 4/Cyan | 18.156.8 (hIgG4) | 30 mg/kg | 7.80 | 4501 |
| 5/Magenta | 40409 (hIgG4) | 10 mg/kg | 1.04 | 5501 |
| 6/Blue | 40409 (hIgG4) | 30 mg/kg | 3.13 | 6501 |

Note:
In this report, "dose level" and "dosage" are used interchangeably.
[a]Doses represent active ingredient.

LDL-C lowering effect of antibody 18.156.8 and 40409 in cynomolgus monkey. Administration of BMK.115 and 18.156.8 (hIgG4) resulted in a rapid and sustained reduction in LDL-C and total cholesterol (TCHO) at 10 mg/kg and 30 mg/kg in cynomolgus monkeys.

Figure 20:
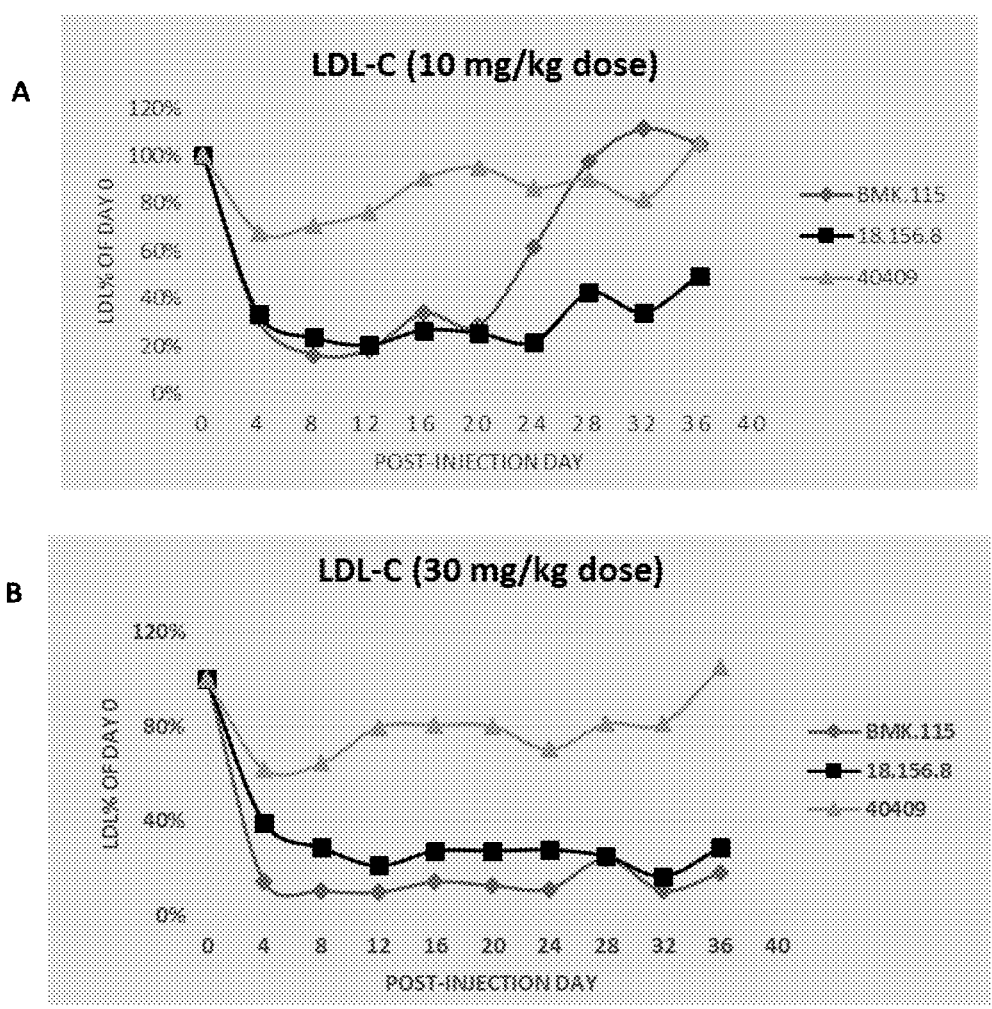
FIG. 20 shows LDL-C change percentage of antibody 18, 156.8, 40409 and BMK.115 treated cynomolgus monkeys.

Percentage reduction of LDL was up to 83.4% and 89.6% in the BMK.115 10 mg/kg and 30 mg/kg dose groups, respectively, compared with predose value. 18.156.8 (hIgG4) yielded significant reductions in LDL-C up to 79.5% and 83.5% in 10 mg/kg and 30 mg/kg dose groups, respectively. The maximum reduction was reached on day 8. Reductions in LDL-C were sustained throughout the in-life phase for 18.156.8 (hIgG4) treated animals in both 10 mg/kg and 30 mg/kg dose groups. Reductions in LDL-C were sustained throughout the in-life phase for BMK.115 treated animals in 30 mg/kg dose group, but the LDL-C of 10 mg/kg group started to restore from day 24 and returned to predose level on day 28 (FIGS. 20A and 20B). Therefore, reduction in LDL-C was sustained longer period in 18.156.8 treated animal at 10 mg/kg dose compared with REPATHA™ treated group.

40409 (hIgG4) reduced LDL-C up to 32.2% and 38.1% in 10 mg/kg and 30 mg/kg dose groups, respectively (see FIGS. 20A and 20B).

Figure 21A:
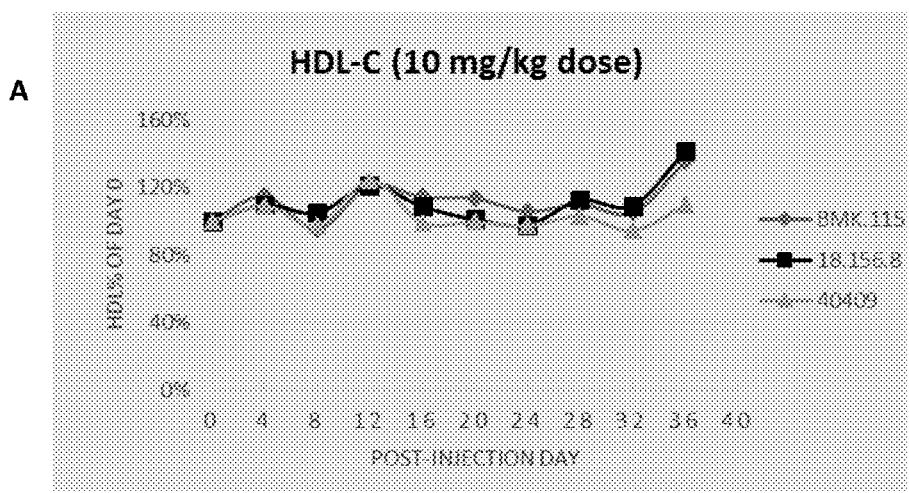
FIG. 21A shows the result of a single dose of 10 mg/kg injection.

High Density Lipoprotein cholesterol (HDL-C) was generally well maintained in the monkeys given 18.156.8 (hIgG4) or 40409 (hIgG4) at 10 mg/kg and 30 mg/kg. HDL-C was generally maintained in the monkey given BMK.115 at 10 mg/kg dose, but decrease of HDL-C(up to 30.4%) was noted in BMK.115 30 mg/kg group compared to the predose value (FIGS. 21A and 21B).

5.1.2 Study 2: A total of 10 female cynomolgus monkeys, approximately 3 to 4 years old and weighing 2.5 to 3.5 kg, at dosing initiation. 10 female monkeys were randomly assigned to 8 groups of 1 female/group. 10 groups of 1 female monkey each received 3 mg/kg or 10 mg/kg of REPATHA™, 15.14.2, 17.72.3, 18.136.7 or 19.3.8 by a single dose intravenous injection. The first dosing day was defined as Day 1. The animals of each group were observed for 36 days following dosing:

| Group/Label<br>color | Test Article | Dose[a]<br>Dose<br>(mg/kg) | Volume<br>(mL/kg) | Numbering of<br>Animals<br>Female |
|---|---|---|---|---|
| 1/White | Repatha | 3 | 0.06 | 1501 |
| 2/Green | Repatha | 10 | 0.2 | 2501 |
| 3/Yellow | 15.14.2 | 3 | 0.5 | 3501 |
| 4/Red | 15.14.2 | 10 | 1.67 | 4501 |
| 5/Cyan | 19.3.8 | 3 | 0.6 | 5501 |
| 6/Magenta | 19.3.8 | 10 | 2 | 6501 |
| 7/Blue | 17.72.3 | 3 | 0.57 | 7501 |
| 8/Cyan | 17.72.3 | 10 | 1.89 | 8501 |
| 9/White | 18.136.7 | 3 | 0.59 | 9501 |
| 10/Green | 18.136.7 | 10 | 1.98 | 10501 |

Note:
In this report, "dose level" and "dosage" are used interchangeably.
[a]Doses represent active ingredient.

LDL-C lowering effect of antibody 15.14.2, 17.72.3, 18.136.7 and 19.3.8 in cynomolgus monkey.

Administration of REPATHA™ and 15.14.2 resulted in a rapid and sustained reduction of LDL-C and total cholesterol (TCHO) at 3 mg/kg and 10 mg/kg in cynomolgus monkeys (FIGS. 22A and 22B). 18.136.7 also showed significant reduction of LDL-C up to ~50% at 3 mg/kg and 10 mg/kg. 17.72.3 and 19.3.8 showed moderate reduction of LDL-C at 10 mg/kg.

Percentage reduction of LDL was up to 80% and 77% in REPATHA™ 3 mg/kg and 10 mg/kg dose groups, respectively, compared with predose value. In 15.14.2 yielded significant reductions in LDL-C up to 77% in both 3 mg/kg and 10 mg/kg dose groups, respectively. The maximum reduction was reached on day 8-16. In the 10 mg/kg dose groups, reduction of LDL-C was sustained throughout the in-life phase for 15.14.2 treated animal, but the LDL-C level started to restore from day 24 and returned to predose level till day 36 for REPATHA™ treated animal (FIGS. 22A and 22B). In the 10 mg/kg dose groups, the LDL-C level of REPATHA™ treated monkey restored to 80% of predose level on day 12 and completely returned to predose level on day 20. The reduction of LDL-C for 3 mg/kg 15.14.2 treated monkey retained lower than 50% till day 28. Therefore, reductions in LDL-C were sustained longer period in 15.14.2 treated animals in both 3 mg/kg and 10 mg/kg dose groups compared with REPATHA™ treated groups.

Figure 23:
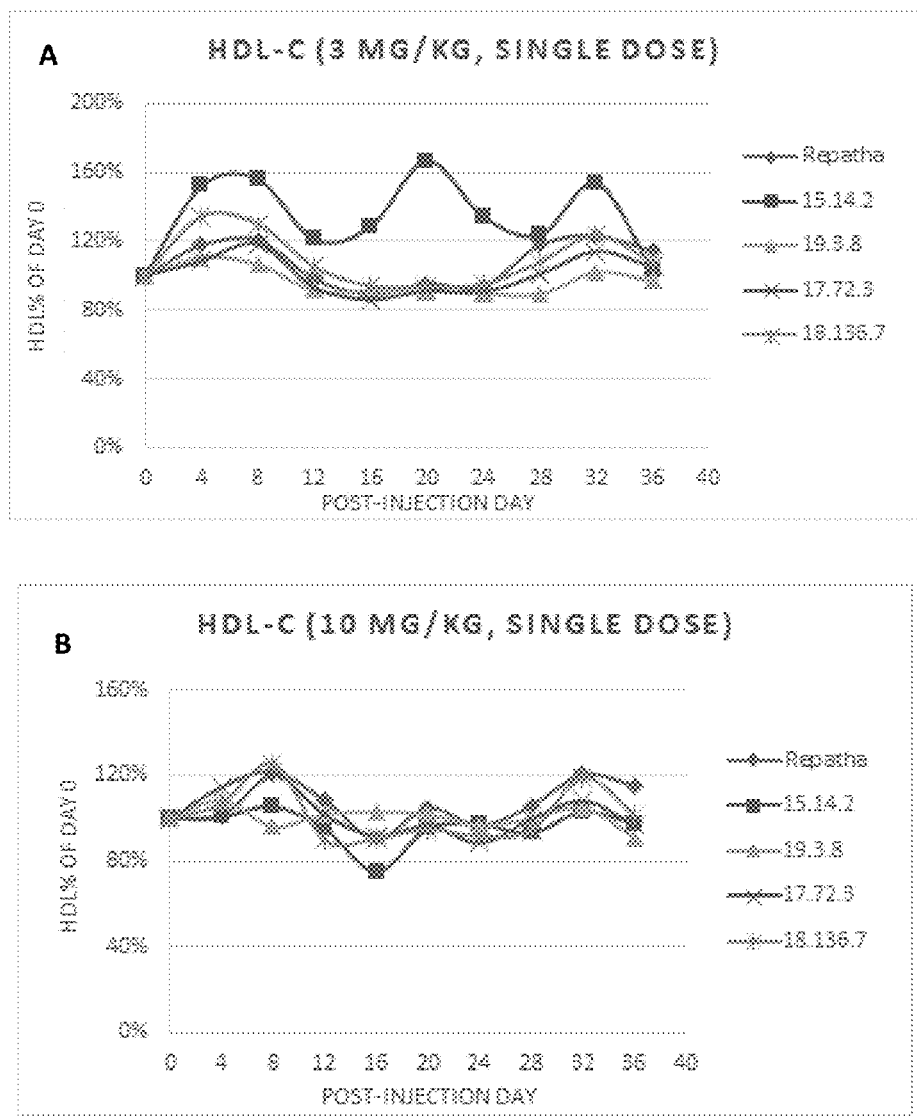
FIG. 23 shows High Density Lipoprotein cholesterol (HDL-C) change percentage of antibody 15.14.2, 19.3.8, 17.72.3, 18.136.7 and REPATHA™ treated cynomolgus monkeys.

High Density Lipoprotein cholesterol (HDL-C) was generally well maintained in the monkeys treated with all the tested antibodies at 3 mg/kg and 10 mg/kg (FIGS. 23A and 23B).

5.2 Pharmacokinetics (PK) Study

To determine systemic exposure (TK), serum concentrations of BMK.115, 18.156.8-hIgG4, 40409-hIgG4, 15.14.2, 17.72.3, 18.136.7 and 19.3.8 were determined. Blood samples were collected from all available monkeys at 0 (predose), 0.5, 1, 2, 4, 24, 48, 96, 168, 336, 504, 672, 744, and 840 hours postdose.

Approximately 2 mL of blood was collected from the animals via a cephalic or a femoral vein. Blood was collected into appropriately labeled tubes without anticoagulant. The tubes were placed at room temperature for at least 30 min, and serum was obtained within 2 hour of collection by centrifugation at 2000×g and ~4° C. for 10 minutes. Serum was transferred into uniquely labeled polypropylene tubes and frozen in the upright position immediately over dry ice and stored in a freezer set to maintain ≤−60° C.

The serum samples were rapidly thawed before PK test. The plates were coated with polyclonal goat anti-human antibody in $Na_2CO_3/NaHCO_3$ buffer at 4° C. overnight. The plates were washed with 0.1% TWEEN™-PBS once before being blocked with 2% BSA/PBS. Diluted cynomolgus serum samples were transferred to the plates and incubated for 1 hr at room temperature. Biotin-labeled goat anti-human IgG antibody and streptavidin-HRP were added to the wells and incubated for 1 hr respectively. The OD value at 450 nm of each well was read after the addition of the substrate and stop solution. The concentrations of antibodies in serum samples were determined by the standard curves.

TK parameter values, including (where data allows), but not necessarily limited to, the initial serum concentrations ($C_0$), and the area under the serum concentration vs time curve (AUC) from time zero to 840 hours postdose $AUC_{0-840h}$, were determined using a validated WINNONLIN™ program (Pharsight, Version 6.2.1). $AUC_{0-840h}$ was calculated using the linear up/log down trapezoidal rule by noncompartmental methods from drug treated animals only. Serum concentrations below the lower limit of quantification (BLQ) were set to zero for TK parameters calculations.

Figure 24A:
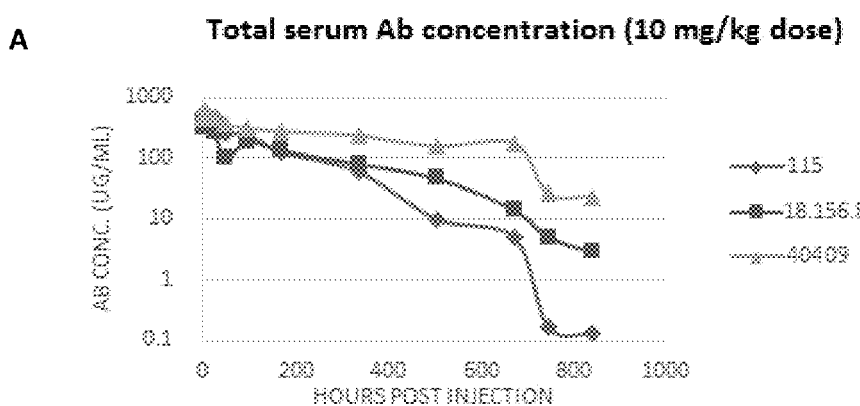
FIG. 24A shows the result of a single dose of 10 mg/kg injection.

The antibody concentration in monkey serum was tested by ELISA (FIGS. 24 and 25). The $C_0$ and $AUC_{0-840h}$ for BMK.115, 18.156.8 (hIgG4), 40409 (hIgG4) following once single IV injection of BMK.115, 18.156.8 (hIgG4), 40409 (hIgG4) at 10 or 30 mg/kg to female monkeys are presented below. The half-life of each antibody was also listed in Table 10.

As the dosage increased from 10 mg/kg to 30 mg/kg, the systemic exposure ($AUC_{0-840h}$ and/or $C_0$) to 18.156.8 and 40409 increased dose-proportionally, but increased more than dose-proportionally to BMK.115.

TABLE 10

Summary of PK data I

| Analyte | Dose (mg/kg) | $C_0$ (ug/mL) | $AUC_{0-840\,h}$ (h * ug/mL) | $T_{1/2}$ (h) |
|---|---|---|---|---|
| BMK.115 | 10 | 643 | 25700 | 57.9 |
|  | 30 | 1970 | 156000 | 112.2 |
| 18.156.8 | 10 | 405 | 25300 | 128.8 |
|  | 30 | 1960 | 89800 | 162.8 |
| 40409 | 10 | 282 | 46200 | 186.8 |
|  | 30 | 2030 | 218000 | 135.0 |

The $C_0$ and $AUC_{0-840h}$ for REPATHA™, 15.14.2, 17.72.3, 18.136.7 and 19.3.8 following once single IV injection at 3 or 10 mg/kg to female monkeys are presented below (see Table 11). The half-life of each antibody was also listed in Table 11. 15.14.2, 17.72.3, 18.136.7 and 19.3.8 all exhibited longer than REPATHA™ in both doses.

As the dosage increased from 3 mg/kg to 10 mg/kg, the systemic exposure ($AUC_{0-840h}$ and/or $C_0$) to REPATHA™, 15.14.2, 17.72.3, 18.136.7 and 19.3.8 increased dose-proportionally.

TABLE 11

Summary of PK data II

| Analyte | Dose (mg/kg) | $C_0$ (ug/mL) | $AUC_{0-840\,h}$ (h * ug/mL) | $T_{1/2}$ (h) |
|---|---|---|---|---|
| Repatha | 3 | 30 | 14000 | 62 |
|  | 10 | 802 | 88900 | 145.2 |
| 15.14.2 | 3 | 240 | 39800 | 177.7 |
|  | 10 | 600 | 181000 | 385.6 |
| 19.3.8 | 3 | 140 | 38700 | 270.9 |
|  | 10 | 360 | 99100 | 446.8 |
| 17.72.3 | 3 | 232 | 25700 | 154.1 |
|  | 10 | 725 | 117000 | 353 |
| 18.136.7 | 3 | 235 | 12600 | 122 |
|  | 10 | 520 | 46100 | 240.7 |

5.3 Immunogenicity

Blood was collected from the animals at 0 (predose), 336, 672 and 840 hours postdose via a cephalic or a femoral vein. The plates were coated with BMK.115, 18.156.8, 40409, 15.14.2, 17.72.3, 18.136.7 or 19.3.8 in $Na_2CO_3$/$NaHCO_3$ buffer at 4° C. overnight. The plates were washed with 0.1% TWEEN™-PBS once before being blocked with 2% BSA/PBS. PBS-diluted cynomolgus serum samples were transferred to the plates and incubated for 1 hr at room temperature. After washing, goat anti-cynomolgus IgG-HRP antibody (no cross-interaction with human IgG) was added. The OD value at 450 nm of each well was read after the addition of the substrate and stop solution.

Figure 26:
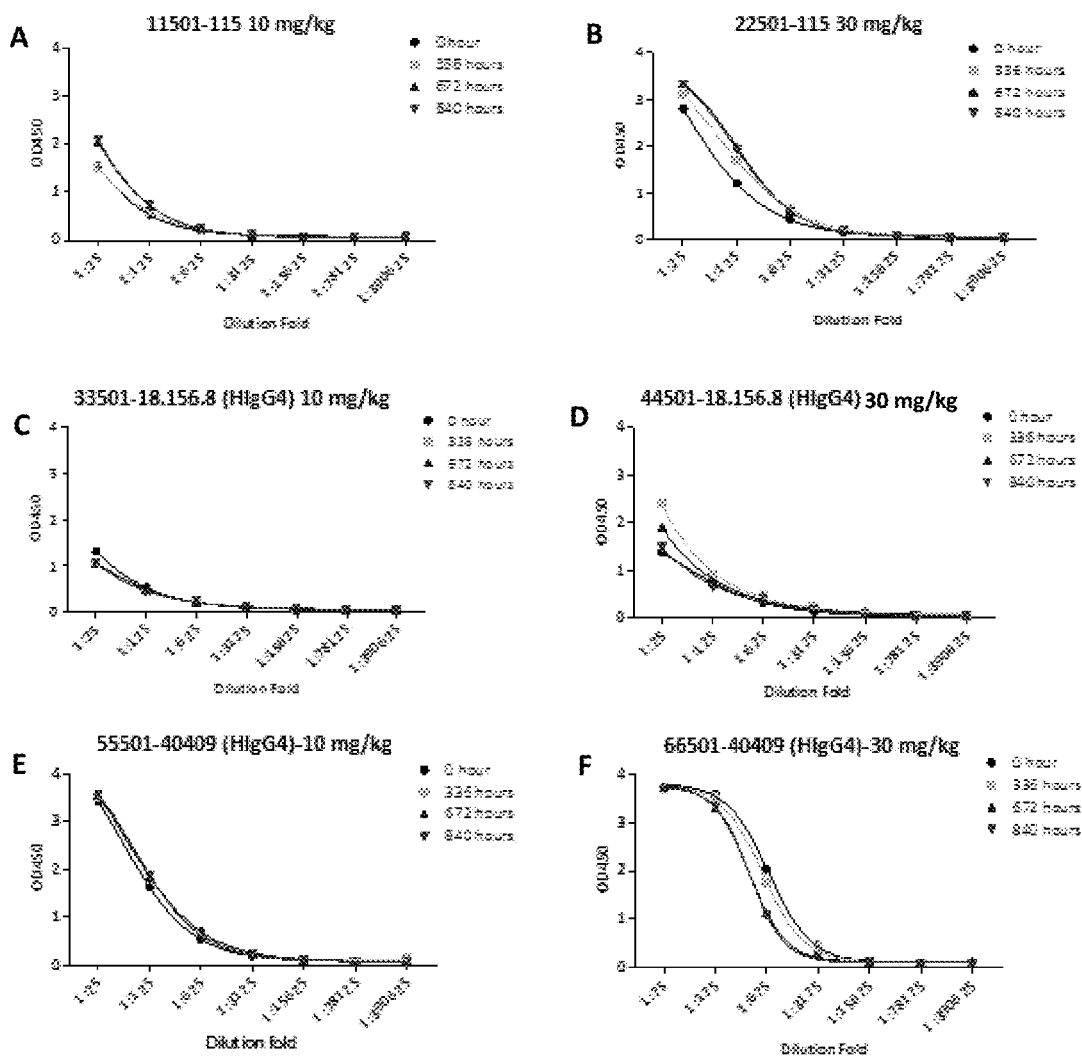
FIG. 26 shows anti-drug antibody (ADA) against 18.156.8(hIgG4), 40409(hIgG4) or BMK.115 in cynomolgus monkey serum samples of predose and postdose.

The immunogenicity test results of BMK.115, 18.156.8 (hIgG4), 40409 (hIgG4) are shown in FIG. 26. The titers of anti-drug antibody (ADA) against BMK.115, 18.156.8 (hIgG4), 40409 (hIgG4) in monkey serum at 336, 672, 840 hours post dose have no significant difference from predose. Therefore, after single IV injection of BMK.115, 18.156.8 (hIgG4), 40409 (hIgG4) at 10 or 30 mg/kg to female monkeys, the results show that BMK.115, 18.156.8 (hIgG4), 40409 (hIgG4) induced low immunogenicity in serum.

The immunogenicity test results of REPATHA™, 15.14.2, 17.72.3, 18.136.7 and 19.3.8 are shown in FIG. 27. The titers of anti-drug antibody (ADA) against REPATHA™, 15.14.2, 17.72.3, 18.136.7 and 19.3.8 in monkey serum at 336, 672, 840 hours post dose have no significant difference from predose. Therefore, after single IV injection of the antibodies at 3 or 10 mg/kg to female monkeys, the results show that REPATHA™, 15.14.2, 17.72.3, 18.136.7 and 19.3.8 induced low immunogenicity in serum.

5.4 Toxicity

Mortality/Moribundity: The health status of each animal was reported twice a day during the study, once in the morning and once in the afternoon, except on animal release and the day of in-life completion where animals were examined once.

There were no unscheduled deaths during the course of the study.

Detailed observations: Detailed observations were conducted once during pretest for all animals (including spare animals), once on dosing day (2±0.5 hours post dose), and once weekly thereafter during the study for all study animals.

There were no test article-related clinical signs observed during the in-life phase.

Cage side observations: Cage side observation was conducted daily during pretest from Day −2 for all animals (including spare animals), once predose on Day 1, and twice daily during the dosing day (within 30 minutes, and at approximately 6±0.5 hours post dose) and once daily during the recovery phase. Cage side observation was not conducted if a detailed observation was scheduled at the same time slot.

Body weights: Each animal was weighed once during pretest for all animals, once on Day 1 prior to dosing, and once weekly thereafter for study animals.

No test article-related findings were observed on body weight, and all changes were considered within biological variation.

Food consumption: Food consumption was estimated daily for all animals 2 days prior to dose initiation and throughout the dosing day and observation period. Daily food evaluation was assessed by visual inspection for overall appetite (the documentation was consist of whether the animal was eating or not).

There were no test article-related changes in food consumption.

EXAMPLE 6: ACTIVITY COMPARISON BETWEEN ANTIBODY 18.156.8 AND REFERENCE ANTIBODIES

1. Reference Antibody Generation

Reference antibody 12H11.1.uIgG4K and 24B9.1.uIgG4L were generated based on the sequence of 12H11.1 and 24B9.1 in Patent CN101932607 using methods described in EXAMPLE 1 and EXAMPLE 2.

Figure 28C:
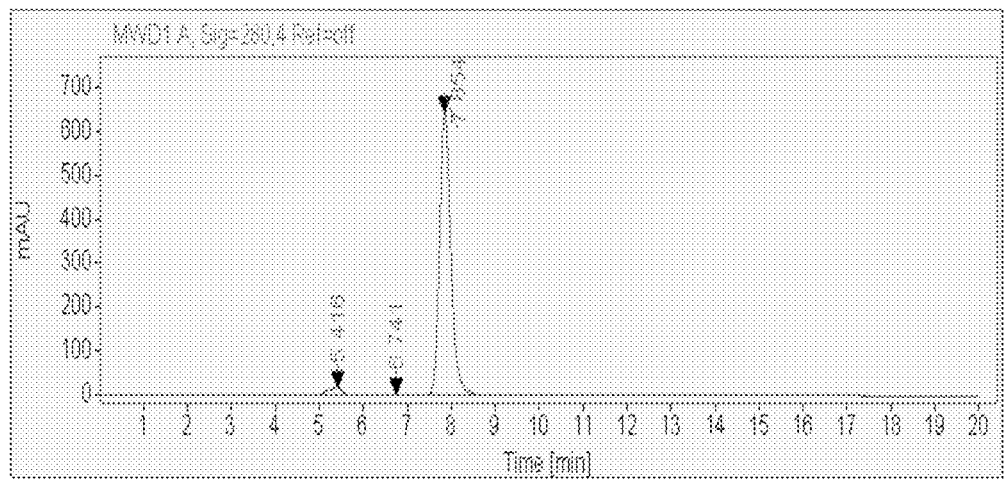

Antibodies 12H11.1.uIgG4K and 24B9.1.uIgG4L migrate with the apparent molecular mass of 25 kDa and 55 kDa in SDS-PAGE under reducing conditions corresponding to light chain and heavy chain (FIG. 28A). The main band under non-reducing condition is the whole IgG with M.W. of ~150 KD. The purity of 24B9.1.uIgG4L is 96.8% as determined by HPLC-SEC (FIG. 28B). The purity of 12H11.1.uIgG4K is 95.3% as determined by HPLC-SEC (FIG. 28C).

2. Binding to Human PCSK9 by ELISA

Figure 29:
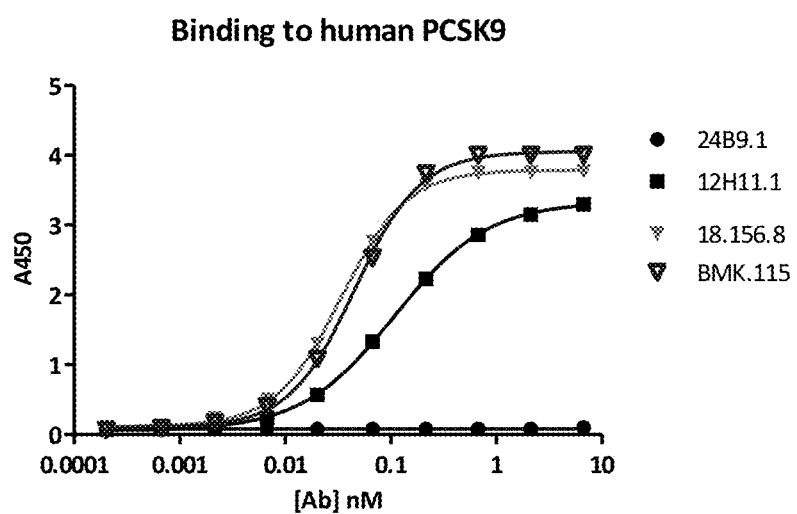
FIG. 29 indicates the comparison of binding to human PCSK9 of antibody 18.156.8 and reference antibodies 24B9.1, 12H11.1 and BMK.115, as measured by ELISA.

The activities of reference antibodies 12H11.1.uIgG4K and 24B9.1.uIgG4L binding to human PCSK9 were confirmed by ELISA (FIG. 29), according to the method described in Section 2.4 Hybridoma screening of EXAMPLE 2. The binding EC50 values were summarized in Table 12. The reference antibodies 12H11.1.uIgG4K showed lower binding activity than 18.156.8 and BMK.115. The reference antibody 24B9.1.uIgG4L does not bind to human PCSK9.

TABLE 12

Binding activity

| Antibody | Binding EC50 (nM) |
|---|---|
| 24B9.1.uIgG4L | No binding |
| 12H11.1.uIgG4K | 0.11 |
| 18.156.8 | 0.034 |
| BMK.115 | 0.046 |

3. Blocking Assay by ELISA

Figure 30:
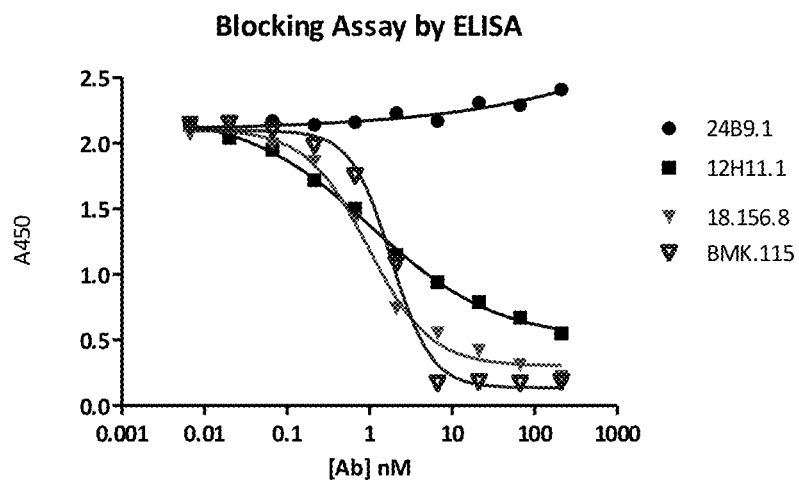
FIG. 30 shows the results of comparison of antibody 18.156.8 and reference antibodies 24B9.1, 12H11.1 and BMK.115 in blocking the binding of PCSK9 to LDLR, as measured by ELISA.

The activities of reference antibodies 12H11.1.uIgG4K and 24B9.1.uIgG4L to blocking the binding of PCSK9 to LDLR were evaluated by competitive ELISA (FIG. 30) according to the methods described in Section 2.4 Hybridoma screening of EXAMPLE 2. The IC50 values were summarized in Table 13. The antibody 24B9.1.uIgG4L showed no blocking activity. The antibody 12H11.1.uIgG4K showed similar IC50 to 18.156.8, but it cannot completely block the binding of PCSK9 and LDLR.

TABLE 13

Blocking activity

| Antibody | Blocking IC50 (nM) |
|---|---|
| 24B9.1.uIgG4L | No blocking |
| 12H11.1.uIgG4K | 1.0 |
| 18.156.8 | 0.97 |
| BMK.115 | 1.8 |

4. Affinity by SPR

The kinetic affinity of antibody 12H11.1.uIgG4K is much lower than 18.156.8, as tested using the same method described in Section 4.3.1 Binding kinetics by SPR of EXAMPLE 4. The results are shown in Table 14.

TABLE 14

Kinetic affinity to human PCSK9

| Antibody | ka (1/Ms) | kd (1/s) | KD (M) |
|---|---|---|---|
| 18.156.8 | 6.49E+05 | 4.47E−05 | 6.88E−11 |
| 12H11.1.uIgG4K | 5.89E+05 | 1.34E−03 | 2.27E−09 |

5. LDL-Uptake Assay

Figure 31:
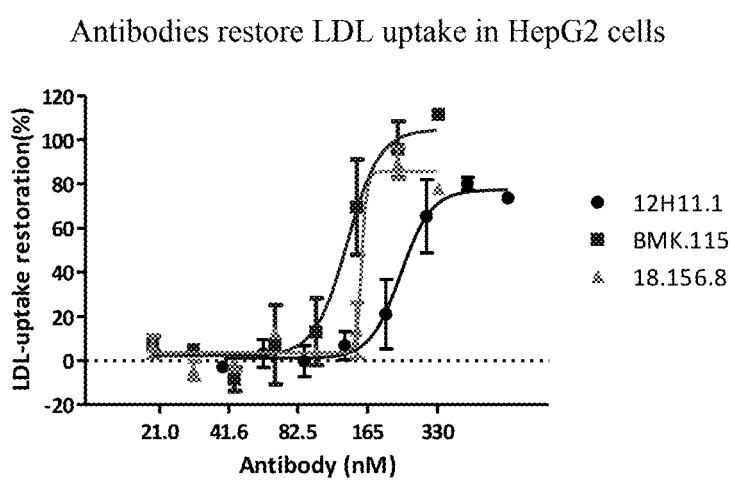
FIG. 31 reveals ability of restoration of LDL-uptake in HepG2 cells for the antibody 18.156.8 and reference antibodies 12H11.1 and BMK.115.

The antibodies 18.156.8 and 12H11.1.uIgG4K were evaluated in LDL-uptake assay in HepG2 cells (see Table 15 and FIG. 31), according to the method described in Section 4.2 LDL uptake assay of fully human antibodies of EXAMPLE 4. 12H11.1.uIgG4K showed slightly lower activity to restore cellular LDL-uptake in HepG2 cell.

TABLE 15

LDL-uptake assay

| Antibody | EC50 (nM) |
|---|---|
| 12H11.1.uIgG4K | 229.7 |
| BMK.115 | 134.9 |
| 18.156.8 | 155.7 |

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. An isolated antibody or an antigen binding fragment thereof, comprising: a heavy chain variable region comprising an HCDR1 comprising SEQ ID NO: 13, an HCDR2 comprising SEQ ID NO: 15, and an HCDR3 comprising SEQ ID NO: 17; and a light chain variable region comprising an LCDR1 comprising SEQ ID NO: 19, an LCDR2 comprising SEQ ID NO: 21, and an LCDR3 comprising SEQ ID NO: 23, wherein the isolated antibody or an antigen binding fragment thereof specifically binds to Proprotein Convertase Subtilisin/Kexin type 9 (PCSK9).

2. The antibody or an antigen binding fragment thereof of claim 1, comprising:
a heavy chain variable region comprising SEQ ID NO: 77 and a light chain variable region comprising SEQ ID NO: 79.

3. The antibody or an antigen binding fragment thereof of claim 1, which is a fully human monoclonal antibody.

4. The antibody or antigen-binding fragment thereof of claim 1, which is a camelized single domain antibody, a diabody, a scFv, an scFv dimer, a BsFv, a dsFv, a (dsFv)2, a dsFv-dsFv', an Fv fragment, a Fab, a Fab', a F(ab')2, a disulfide stabilized diabody (ds diabody), a nanobody, a domain antibody, or a bivalent domain antibody.

5. The antibody or antigen-binding fragment thereof of claim 1, further comprising an immunoglobulin constant region.

6. The antibody or antigen-binding fragment thereof of claim 1, further comprising a conjugate.

7. A pharmaceutical composition comprising the antibody or antigen-binding fragment thereof of claim 1 and one or more pharmaceutically acceptable carriers.

8. A kit comprising the antibody or antigen-binding fragment thereof of claim 1.

9. An isolated polynucleotide encoding the antibody or an antigen binding fragment thereof of claim 1.

10. A vector comprising the isolated polynucleotide of claim 9.

11. An isolated host cell comprising the vector of claim 10.

12. A method of expressing an antibody or antigen-binding fragment thereof, comprising culturing the host cell of claim 11 under conditions at which the polynucleotide is expressed.

* * * * *